US010703798B2

(12) United States Patent
Tanaka et al.

(10) Patent No.: US 10,703,798 B2
(45) Date of Patent: Jul. 7, 2020

(54) METHODS OF CANCER THERAPY BY INHIBITING FUSION POLYPEPTIDES COMPRISING FIBROBLAST GROWTH FACTOR RECEPTOR 2 (FGFR2) AND VINCULIN (VCL)

(71) Applicant: DEBIOPHARM INTERNATIONAL SA, Lausanne (CH)

(72) Inventors: Hiroaki Tanaka, Lausanne (CH); Corinne Moulon, Saint-Légier (CH); Anne Vaslin Chessex, Prilly (CH); Jérôme Wojcik, Divonne-les-Bains (FR); Claudia Armenise, Eloise (FR)

(73) Assignee: DEBIOPHARM INTERNATIONAL SA, Lausanne (CH)

(*) Notice: Subject to any disclaimer, the term of this patent is extended or adjusted under 35 U.S.C. 154(b) by 59 days.

(21) Appl. No.: 15/301,217

(22) PCT Filed: Mar. 31, 2015

(86) PCT No.: PCT/IB2015/000429
§ 371 (c)(1),
(2) Date: Sep. 30, 2016

(87) PCT Pub. No.: WO2015/150900
PCT Pub. Date: Oct. 8, 2015

(65) Prior Publication Data

US 2017/0107271 A1 Apr. 20, 2017

(30) Foreign Application Priority Data

Mar. 31, 2014 (WO) .................. PCT/IB2014/000467
Mar. 6, 2015 (WO) .................. PCT/IB2015/000288

(51) Int. Cl.

| | |
|---|---|
| ***C07K 14/47*** | (2006.01) |
| ***C07K 14/71*** | (2006.01) |
| ***C07K 16/18*** | (2006.01) |
| ***C07K 16/28*** | (2006.01) |
| ***C07K 16/40*** | (2006.01) |
| ***G01N 33/574*** | (2006.01) |
| ***A61K 31/4184*** | (2006.01) |
| ***G01N 33/50*** | (2006.01) |
| ***C12N 9/12*** | (2006.01) |
| ***C12N 15/113*** | (2010.01) |
| ***C12Q 1/6886*** | (2018.01) |

(52) U.S. Cl.

CPC .......... *C07K 14/71* (2013.01); *A61K 31/4184* (2013.01); *C07K 14/47* (2013.01); *C07K 16/18* (2013.01); *C07K 16/2863* (2013.01); *C07K 16/40* (2013.01); *C12N 9/12* (2013.01); *C12N 15/1138* (2013.01); *C12Q 1/6886* (2013.01); *C12Y 207/10001* (2013.01); *G01N 33/5011* (2013.01); *G01N 33/57407* (2013.01); *G01N 33/57492* (2013.01); *C07K 2319/00* (2013.01); *C12N 2310/11* (2013.01); *C12N 2310/14* (2013.01); *C12Q 2600/136* (2013.01); *C12Q 2600/158* (2013.01); *G01N 2333/47* (2013.01); *G01N 2333/71* (2013.01); *G01N 2333/912* (2013.01)

(58) Field of Classification Search

CPC ........ C07K 14/47; C07K 14/71; C07K 16/18; C07K 16/2863; C07K 16/40; C07K 2319/00; C12N 15/1138; C12N 9/12; C12N 2310/11; C12N 2310/14; A61K 31/4184; C12Q 1/6886; C12Q 2600/158; C12Q 2600/136; C12Y 207/10001; G01N 33/5011; G01N 33/57407; G01N 33/57492; G01N 2333/47; G01N 2333/71; G01N 2333/912

See application file for complete search history.

(56) References Cited

U.S. PATENT DOCUMENTS

| | | | |
|---|---|---|---|
| 9,102,692 | B2 | 8/2015 | Taka et al. |
| 2012/0208811 | A1 | 8/2012 | Taka et al. |

FOREIGN PATENT DOCUMENTS

| | | | |
|---|---|---|---|
| EP | 2695950 | A1 | 2/2014 |
| JP | 2012-180344 | A | 9/2012 |
| WO | 2011/016528 | A1 | 2/2011 |
| WO | 2014/018673 | A2 | 1/2014 |

OTHER PUBLICATIONS

Mitelman et al; “The impact of translocations and gene fusions on cancer causation;” Nature Reviews Cancer; 2007; pp. 233-245.

Annala et al; “Fusion genes and their discovery using high throughput sequencing;” Cancer Letters; 2013; vol. 340; pp. 192-200.

Shaw et al; “Tyrosine kinase gene rearrangements in epithelial malignancies;” Nature Reviews Cancer; 2013; vol. 13; pp. 772-787.

Parker et al; “The tumorigenic FGFR3-TACC3 gene fusion escapes miR-99a regulation in glioblastoma;” The Journal of Clinical Investigation; 2013; vol. 123; pp. 855-865.

Kopitz et al; “Abstract DDT02-01: In vitro and in vivo characterization of a novel anti-fibroblast growth factor receptor (FGFR) 2 antibody (BAY 1179470) for the treatment of gastric cancer;” Cancer Research; 2014.

Gemo et al; Abstract 5446: FPA144: A therapeutic antibody for treating patients with gastric cancers bearing FGFR2 gene amplification: Cancer Research; 2014; 4 pp.

Sommer et a; “Abstract 4491: FGFR2-ADC potently and selectively inhibits growth of gastric and breast cancer xenograft models;” Cancer Research; 2014; 4 pp.

(Continued)

*Primary Examiner* — Robert S Landsman
(74) *Attorney, Agent, or Firm* — Oliff PLC

(57) ABSTRACT

Fusion polypeptides have an FGFR2 polypeptide and cDNAs encode such fusion polypeptides. Methods of diagnosing the presence of the fusion polypeptides or of a gene or RNA sequence coding therefore in a sample from a subject as well as methods of treatment of a tumor instructed by the latter diagnosis.

22 Claims, 10 Drawing Sheets

Specification includes a Sequence Listing.

(56) References Cited

OTHER PUBLICATIONS

Mohammadi et al; "Crystal structure of an angiogenesis inhibitor bound to the FGF receptor tyrosine kinase domain;" The EMBO Journal; 1998; vol. 17; No. 20; pp. 5896-5904.
Harris et al; "Discovery of 5-[[4-[2,3-Dimethyl-2H-indazol-6-yl)methylamino]-2-pyrimidinyl]amino]-2-methyl-benzenesulfonamide (Pazopanib), a Novel and Potent Vascular Endothelial Growth Factor Receptor Inhibitor;" J. Med. Chem.; 2008; vol. 57; pp. 4632-4640.
Keisner et al; "Pazopanib: The Newest Tyrosine Kinase Inhibitor for the Treatment of Advanced or Metastatic Renal Cell Carcinoma;" Drugs; 2001; vol. 71; No. 4; pp. 443-454.
Gavine et al; "AZD4547: An Orally Bioavailable, Potent, and Selective Inhibitor of the Fibroblast Growth Factor Receptor Tyrosine Kinase Family;" Cancer Research; vol. 72; pp. 2045-2056, 2012.
Huang et al; "Discovery of 3-[2-(Imidazo[1,2-b]pyridazin-3-yl)ethynyl]-4-methyl-N-{4-[(4-methylpiperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T3151 Gatekeeper Mutant;" J. Med. Chem.; 2010; vol. 53; pp. 4701-4719.
Trudel et al; "CHIR-258, a novel, multitargeted tyrosine kinase inhibitor for the potential treatment of t(4;14) multiple myeloma;" 2005; Blood; vol. 105; pp. 2941-2948.
Man et al; "Dovitinib induces miotic defects and activates the G2 DNA damage checkpoint;" J. Cell. Mol. Med.; 2014; vol. 18; No. 1; pp. 143-155.
Guagnano et al; "Disovery of 3-2,6-Dichloro-3,5-dimethoxy-phenyl)-1-[6-|4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase;" J. Med. Chem.; 2011; vol. 54; pp. 7066-7083.
Bello et al; "E-3810 is a Potent Dual Inhibitor of VEGFR and FGFR that Exerts Antitumor Activity in Multiple Preclinical Models;" Cancer Research; 2011; vol. 71; pp. 1396-1405.
Squires et al; "Development of inhibitors of the fibroblast growth factor receptor (FGFR) kinase using a fragment based approach;" Cancer Research; 2008; 4 pp.
Yu et al; Abstract 3571: Exploratory biomaker discovery for clinical development of ARQ 087, a potent pan-FGFR kinase inhibitor, Cancer Research; 2011; vol. 71; 4 pp.
Zhao et al; "A Novel, Selective Inhibitor of Fibroblast Growth Factor Receptors That Shows a Potent Broad Spectrum of Antitumor Activity in Several Tumor Xenograft Models;" Molecular Cancer Therapeutics; 2011; vol. 10; No. 11; pp. 2200-2210.
Heroult et al: "Abstract 1739: Preclinical profile of BAY 1163877—a selective pan-FGFR inhibitor in phase 1 clinical trial;" Cancer Research; 2014; vol. 74; 4 pp.
"ASP5878;" 73rd Annual Meeting of the Japanese Cancer Association; Sep. 25, 2014; 3 pp.
Miyano et al; "Abstract 770: E7090: A potent and selective FGFR inhibitor with activity in multiple FGFR-driven cancer models with distinct mechanisms of activitation;" Cancer Research; 2015; 4 pp.
Holström et al; "ODM-203, a novel, selective and balanced FGFR and VEGFR inhibitor with strong anti-tumor activity in FGFR- and VEGFR-dependent cancer models;" European Journal of Cancer; Nov. 2014; vol. 50: Supplement 6; 3 pp.
Roth et al; "Nintedanib: From Discovery to the Clinic;" Journal of Medicinal Chemistry; 2015; vol. 58; pp. 1053-1063.
Ochiiwa et al; "Abstract A270: TAS-120, a highly potent and selective irreversible FGFR inhibitor, is effective in tumors harboring various FGFR gene abnormalities;" Molecular Cancer Therapeutics; vol. 12; Supplement 11: 4 pp, 2013.
Phan et al; "Irreversible covalent pan-FGFR inhibitors are highly efficacious against FGFR-dependent cancers;" European Journal of Cancer: Nov. 2014; vol. 50; Supplement 6; 3 pp.
Debelenko et al; "Renal cell carcinoma with novel VCL-ALK fusion: new representative of ALK-associated tumor spectrum;" Modern Pathology; 2011; vol. 24; pp. 430-442.
Arai et al; "Fibroblast Growth Factor Receptor 2 Tyrosine Kinase Fusions Define a Unique Molecular Subtype of cholangiocarcinoma;" Heptaology; 2014; vol. 59; No. 4; pp. 1428-1434.
Oct. 2, 2015 Search Report issued in International Patent Application No. PCT/IB2015/000429.
Oct. 2, 2015 Written Opinion issued in International Patent Application No. PCT/IB2015/000429.
Rakitina, T. et al., "Panel Tyrosine Kinase as a Tool for the Development of Anticancer Drugs", (2009), Acta Naturae, vol. 1, No. 3: pp. 93-97.
Nov. 28, 2018 Office Action issued in Russian Patent Application No. 2016137179/10.
Aug. 4, 2017 Office Action issued in European Patent Application No. 15722580.6.
Aug. 11, 2017 Search Report issued in Singaporean Patent Application No. 11201607772W.
Wu, Yi-Mi et al., "Identification of Targetable FGFR Gene Fusions in Diverse Cancers", (2013), Cancer Discovery, vol. 3, No. 6: pp. 636-647.
Rakitina, T. et al., "Panel Tirozinovykh Kinaz Kak Instriment Dlya Razrabotki Protovorakovykh Preparatov", (2009), Acta Naturae, vol. 1, No. 3: pp. 93-97.
Reynolds, Vincent L. et al., "Inherent Tumorigenic and Metastatic Properties of Rat-1 and Rat-2 Cells", (1987), Cancer Research, vol. 47, No. 23: pp. 6384-6387.
Keath, Elizabeth J. et al., "Fibroblast Lines Expressing Activated C-Myc Oncogenes are Tumorigenic in Nude Mice and Syngeneic Animals", (1984), vol. 39, No. 2: pp. 339-348.
Borad, Mitesh J. et al., "Integrated Genomic Characterization Reveals Novel, Therapeutically Relevant Drug Targets in FGFR and EGFR Pathways in Sporadic Intrahepatic Cholangiocarcinoma", (2014), PLOS Genetics, vol. 10, No. 2, e1004135: pp. 1-21.
Wolf, Jurgen et al. "A Phase I Dose Escalation Study of NVP-BGJ398, a Selective Pan FGFR Inhibitor in Genetically Preselected Advanced Solid Tumors", (2012), http://cancerres.aacrjournals.org/content/72/8_Supplement/LB-122.

A (VCL)

B (CCDC147)

| Cell line / IC50 (nM) | Rat2_parental | Rat2_FGFR2-VCL | Rat2_FGFR2-CCDC147 |
|---|---|---|---|
| Compound A | >1024 | 227 | 14.7 |
| Ponatinib | 731 | 14.4 | 5.3 |
| AZD4547 | >1024 | 32 | 4.1 |
| BGJ-398 | >1024 | 28.1 | 0.2 |

| Cell line / IC50 (nM) | Rat2_parental | Rat2_FGFR2-VCL | Rat2_FGFR2-CCDC147 |
|---|---|---|---|
| Compound A | >3000 | 0.53 | 73.4 |
| Ponatinib | 770 | 99.9 | 144.8 |
| AZD4547 | >3000 | 27.1 | 11.9 |
| BGJ-398 | >3000 | 35.1 | 8.3 |

A

B

C

METHODS OF CANCER THERAPY BY INHIBITING FUSION POLYPEPTIDES COMPRISING FIBROBLAST GROWTH FACTOR RECEPTOR 2 (FGFR2) AND VINCULIN (VCL)

FIELD OF THE INVENTION

The present invention relates to fusion genes that comprise a polypeptide-coding sequence from a fibroblast growth factor receptor and another polypeptide-coding sequence. It further relates to the fusion polypeptides encoded by the genes as well as to DNA copies of the fusion polypeptide-coding sequences. The invention also encompasses diagnostic and therapeutic applications that are based on the latter fusion genes and polypeptides.

BACKGROUND OF THE INVENTION

Certain somatic fusion genes have been known to be drivers of cancer initiation and progression. Mittelman, F., et al. (2007) Nature Reviews Cancer 7: 233-245. The first, now classic, example of a cancer-promoting fusion gene is the BCR-ABL1 fusion gene that is found in over 95% of chronic myelogenous leukemia (chronic-phase CML) patients. The BCR-ABL1 gene encodes a constitutively active form of ABL kinase. The optimal frontline treatment for patients with chronic-phase CML is the subject of active clinical evaluation but involves relatively specific inhibitors of the BCR/ABL tyrosine kinase. Currently marketed inhibitors include first generation drug imatinib (current first line treatment) and second generation drugs nilotinib, dasatinib, bosutinib and ponatinib. Fusion genes were also found to occur with high frequencies in other hematological cancers. Annala, M. J., et al. (2013) Cancer Lett. 340: 192-200. The ETV6-RUNX1 and BCR-ABL1 fusions appear in 25% and 14%, respectively, of acute lymphocytic leukemias, the RUNX1-ETO and CBFB-MYH11 fusions in 10-15% of acute myeloid leukemias, the IG@-MYC fusion in 90-100% of Burkitt's lymphomas, the PML-RARA fusion in 95% of acute promyelocytic leukemias, and the NPM1-ALK and TPM-ALK fusions in 75% and 15%, respectively, of anaplastic large cell lymphomas. While fusion genes historically were detected with relatively high frequencies in hematological cancers, they were only found in a small fraction of solid tumors. More recently, however, it became clear that fusion genes could also occur with elevated frequencies in solid tumors. Annala et al. (2013). Fusions of TMPRSS2 and members of the ETS family of transcription factors were found in about 70% of prostate cancer patients. EML4-ALK fusions can be present in non-small cell lung cancers, KIAA1549-BRAF fusions in pediatric glioma and FGFR3-TACC3 fusions in glioblastoma. Comprehensive listings of known fusion genes are found, e.g., in Annala et al. or in Shaw, A. T. et al. (2013) Nature Reviews Cancer 13: 772-787. It is noted that some fusions can occur in different cancers. As an example, TPM3-ALK fusions were identified in anaplastic large cell lymphoma and in inflammatory myofibroblastic tumors. Other ALK fusions occur in non-small lung cell cancers as well as in anaplastic large cell lymphoma.

Fusions can be cancer-promoting by different mechanisms. In the case of BCR-ABL, for example, the BCR partner provides dimerization domains, causing constitutive dimerization of the ABL domain, which results in constitutive ABL kinase activity and, consequently, uncontrolled cell division. An alternative mechanism is at play in the case of the TMPRSS2-ETS fusions found in prostate cancer. In these fusion genes, a sequence coding for an ETS transcription factor is brought under the control of the androgen-regulated TMPRSS2 promoter, causing the transcription factor to be overexpressed. Overexpressed ETS dysregulates the expression of genes associated with normal prostate epithelial differentiation and causes uncontrolled cell proliferation. In yet another mechanism, up-regulation of the expression of the FGFR polypeptide can result from the loss of a miRNA regulation site in the 3'UTR of the FGFR mRNA, which loss occurs when the FGFR gene fuses with another gene. Parker, B. C. et al. (2013) J. Clin. Invest. 123: 855-865.

Discovery and characterization of fusion genes advance cancer therapy in multiple ways. Taking as examples fusion genes encoding activated tyrosine kinases, e.g., ABL1, ALK, ROS1, RET and FGFR1-3, identification of such fusion genes in cancerous tissue from patients motivates the discovery and development of selective or specific inhibitors directed against the relevant kinases. The presence of fusion kinase genes also informs the choice of therapeutic approach. For example, the first line treatment for chronic-phase CML patients expressing BCR-ABL1 fusion kinase is a regimen comprising BCR-ABL kinase inhibitor imatinib. Discovery of fusion kinase genes provides a basis for devising diagnostic assays that are capable of discovering the presence of such genes or the expression of the products of such genes in tissues from a cancer patient. As discussed for chronic-phase CML, a positive diagnosis of the presence of a fusion kinase gene or of gene products thereof in a tumor tissue of a patient will allow a physician to decide on the most appropriate therapy regimen. Typically, such a regimen will include administration of a composition that inhibits the expression or the activity of the fusion kinase in question.

There is no reason to believe that all fusion genes relevant to cancer (or other diseases) are now known. The discovery and characterization of additional fusion genes is expected to increase the specificity of cancer treatment subsequent to the development of diagnostic methods for the newly discovered fusion genes or polypeptides and the development or identification of specific inhibitors of the newly discovered fusion genes or polypeptides or of other agents directed to the fusion genes or polypeptides. In fact, there is an increasing need for identifying specific subpopulations, for example, among cancer patients who would benefit the most from a given treatment such as a therapy involving a particular kinase inhibitor.

SUMMARY OF THE INVENTION

The present invention relates to a cDNA encoding a fusion polypeptide comprising an FGFR2 polypeptide and a CCDC147 polypeptide or a VCL polypeptide, wherein the FGFR2 polypeptide is the whole or a part of a wildtype FGFR2 polypeptide, or the whole or a part of a mutant FGFR2 polypeptide having one or more amino acid substitutions, deletions, or insertions with respect to the wildtype polypeptide; the CCDC147 polypeptide is the whole or a part of a wildtype CCDC147 polypeptide, or the whole or a part of a mutant CCDC147 polypeptide having one or more amino acid substitutions, deletions, or insertions with respect to the wildtype polypeptide; and the VCL polypeptide is the whole or a part of a wildtype VCL polypeptide, or the whole or a part of a mutant VCL polypeptide having one or more amino acid substitutions, deletions, or insertions with respect to the wildtype polypeptide. The FGFR2 polypeptide in a fusion polypeptide can be the whole or a part of a wildtype polypeptide having the amino acid sequence of either of SEQ ID NOs: 17, 25, 27, 29, 39, 41, 43, 45, 47, 49, 51, 53, 55, 57 and 59, or the whole or a part of a mutant polypeptide that differs by one or more amino acid substitutions, deletions, or insertions from the respective wildtype polypeptide which is a polypeptide according to either of SEQ ID NOs: 17, 25, 27, 29, 39, 41, 43, 45, 47, 49, 51, 53, 55, 57 and 59. The CCDC147 polypeptide in a fusion polypeptide can be the whole or a part of a wildtype polypeptide having the amino acid sequence of either of SEQ ID NOs: 21 and 63, or the whole or a part of a mutant polypeptide with one or more amino acid substitutions, deletions, or insertions in the wildtype polypeptide. The VCL polypeptide in a fusion polypeptide can be the whole or a part of a wildtype polypeptide having the amino acid sequence of either of SEQ ID NOs: 19, 33, 35 and 61, or the whole or a part of a mutant polypeptide with one or more amino acid substitutions, deletions, or insertions in the wildtype polypeptide.

The cDNA encoding a fusion polypeptide comprising an FGFR2 polypeptide and a CCDC147 polypeptide or a VCL polypeptide combines a first and a second polynucleotide. The first polynucleotide encodes the whole or a part of a wildtype FGFR2 polypeptide or a mutant polynucleotide derived therefrom by substitution, deletion or insertion of one or more codons; and the second polynucleotide encodes the whole or a part of a wildtype CCDC147 polypeptide or VCL polypeptide or a mutant polynucleotide derived therefrom by substitution, deletion or insertion of one or more codons. In a particular embodiment, the first polynucleotide encodes the whole or a part of a wildtype FGFR2 polypeptide and includes all or part of the nucleotide sequence of either of SEQ ID NOs: 16, 22, 24, 26, 28, 38, 40, 42, 44, 46, 48, 50, 52, 54, 56 and 58, or a nucleotide sequence derived therefrom by substitution, deletion or insertion of one or more codons. The second polynucleotide encodes the whole or a part of a wildtype CCDC147 polypeptide or a wildtype VCL polypeptide and includes all or part of the nucleotide sequence of either of SEQ ID NOs: 20, 36 and 62 (CCDC147) or either of SEQ ID NOs: 18, 30, 32, 34 and 60 (VCL), or a nucleotide sequence derived from any of the latter nucleotide sequences (i.e., SEQ ID NOs: 20, 36 or 62 (CCDC147), or SEQ ID NOs: 18, 30, 32, 34 or 60 (VCL)) by substitution, deletion or insertion of one or more codons (amino acid-coding nucleotide triplets).

In a more particular embodiment, the cDNA encoding a fusion polypeptide comprises an FGFR2 polypeptide including a complete tyrosine kinase domain and a CCDC147 polypeptide or a VCL polypeptide. A tyrosine kinase domain is considered complete, if it enables the fusion polypeptide to exhibit a detectable tyrosine kinase activity. In this embodiment, the first of the two polynucleotides of the cDNA encoding a fusion polypeptide comprising an FGFR2 polypeptide and a CCDC147 polypeptide or a VCL polypeptide encodes an FGFR2 polypeptide fragment that is sufficiently long to include a complete tyrosine kinase domain.

In an even more particular embodiment, the first of the two polynucleotides of the cDNA encoding a fusion polypeptide comprising an FGFR2 polypeptide and a CCDC147 polypeptide or a VCL polypeptide contains FGFR2 exons 1-16 and part or all of FGFR2 exon 17, and the second of the two polynucleotides contains either CCDC147-coding sequences that lack CCDC147 exon 1 (or that start from exon 2) or VCL-coding sequences that lack VCL exons 1-14 (or that start from exon 15). In the present invention, the exon annotation is performed on the basis of the longest coding transcript found in Ensembl v42 assembly for each part of a fusion gene, i.e. SEQ ID NO: 16 for FGFR2, SEQ ID NO: 18 for VCL and SEQ ID NO: 20 for CCDC147.

The cDNAs of the afore-mentioned embodiments can be derived from a gene transcript isolated from a human cholangiocarcinoma.

More specific embodiments concern the polynucleotide (cDNA) sequences of SEQ ID NO: 1 and SEQ ID NO: 2.

The present invention also encompasses vectors carrying a cDNA of the invention, whereby such vectors can be expression vectors that support the expression of the fusion polypeptide encoded in the cDNA in the cell type for which the vectors are adapted. The invention also relates to any cell (e.g. prokaryotic or eukaryotic) that contains a vector carrying a cDNA of the invention. This cell can be an *E. coli* or a mammalian cell.

Other embodiments of the invention relate to fusion polypeptides comprising an FGFR2 polypeptide and a CCDC147 polypeptide or a VCL polypeptide, which fusion polypeptides are either recombinant polypeptides, polypeptides isolated from cancer cells propagated in vitro or as xenografts, or polypeptides isolated (purified) from human cholangiocarcinomas. The FGFR2 polypeptide comprised in the fusion polypeptide is the whole or a part of a wildtype FGFR2 polypeptide, or the whole or a part of a mutant. FGFR2 polypeptide having one or more amino acid substitutions, deletions, or insertions with respect to the wildtype polypeptide; the CCDC147 polypeptide is the whole or a part of a wildtype CCDC147 polypeptide, or the whole or a part of a mutant CCDC147 polypeptide having one or more amino acid substitutions, deletions, or insertions with respect to the wildtype polypeptide; and the VCL polypeptide is the whole or a part of a wildtype VCL polypeptide, or a part of a mutant VCL polypeptide having one or more amino acid substitutions, deletions, or insertions with respect to the wildtype polypeptide.

In a particular embodiment, the FGFR2 polypeptide comprised in the fusion polypeptide is the whole or a part of a wildtype polypeptide having the amino acid sequence of either of SEQ ID NOs: 17, 25, 27, 29, 39, 41, 43, 45, 47, 49, 51, 53, 55, 57 and 59, or the whole or a part of a mutant polypeptide having one or more amino acid substitutions, deletions, or insertions with respect to the wildtype polypeptide. The CCDC147 polypeptide comprised in the fusion polypeptide is the whole or a part of a wildtype polypeptide having the amino acid sequence of either of SEQ ID NOs: 21 and 63, or the whole or a part of a mutant polypeptide having one or more amino acid substitutions, deletions, or insertions with respect to the wildtype polypeptide. The VCL polypeptide comprised in the fusion polypeptide is the whole or a part of a wildtype polypeptide having the amino acid sequence of either of SEQ ID NOs: 19, 33, 35 and 61, or the whole or a part of a mutant polypeptide having one or more amino acid substitutions, deletions, or insertions with respect to the wildtype polypeptide.

A further embodiment relates to an antibody or antigen-binding fragment that binds a fusion polypeptide of the invention. The antibody or antigen-binding fragment can recognize any sequence of the fusion polypeptide. In a specific embodiment, the antibody or antigen-binding fragment recognizes an epitope that is composed of sequences from both fusion partners, i.e., from FGFR2 and from CCDC147 or VCL.

The invention also relates to oligonucleotides that can specifically hybridize to a gene for a fusion polypeptide of the invention, an RNA transcript of such a gene or a cDNA of the invention. A particular embodiment concerns a primer pair consisting of a sense and an antisense primer, which primers are capable of specifically hybridizing to a cDNA of the invention and of directing replication of the cDNA or parts thereof. The same primers can also be used to amplify genomic sequences encoding a fusion polypeptide of the invention or RNA transcripts thereof. Another embodiment relates to an oligonucleotide probe capable of specifically hybridizing to a cDNA of the invention, a gene encoding a fusion polypeptide of the invention or an RNA transcript of such a gene. In another embodiment, the oligonucleotide is an antisense oligonucleotide capable of hybridization in a life cell to a messenger RNA encoding a fusion polypeptide of the invention. Such hybridization prevents or reduces translation of the messenger RNA. Alternatively, the oligonucleotide can be a siRNA directed to a messenger RNA encoding a fusion polypeptide of the invention.

The present invention also encompasses kits for detecting either a fusion polypeptide of the invention or a gene encoding such a fusion polypeptide or its RNA transcripts. A kit for detecting a fusion polypeptide can comprise one or more antibodies or antigen-binding fragments capable of binding the fusion polypeptide. A kit for detecting a gene or a transcript of a gene encoding a fusion polypeptide can comprise the above-described primer pair or oligonucleotide probe.

Also within the scope of the present invention are inhibitors of FGFR kinase activity for use in a therapeutic regimen in a subject suffering from cancer, wherein said subject contains or expresses a gene encoding a fusion polypeptide of the invention or expresses such a fusion polypeptide. The FGFR kinase inhibitor can be selected from the group consisting of 5-amino-1-(2-methyl-1H-benzimidazol-5-yl)-1H-pyrazol-4-yl]-(1H-indol-2-yl)-methanone, PD173074, Pazopanib, AZD4547, Ponatinib, Dovitinib, BGJ398, E-3810, JNJ-42756493, ARQ 087, LY2874455, BAY1163877, ASP5878, E7090, ODM-203, Nintedanib, TAS-120, PRN 1109 and PRN 1371. More specifically, the FGFR kinase inhibitor can be 5-amino-1-(2-methyl-1H-benzimidazol-5-yl)-1H-pyrazol-4-yl]-(1H-indol-2-yl)-methanone.

The present invention also concerns a method of personalized cancer therapy, comprising subjecting a subject containing or expressing a gene for a fusion polypeptide of the invention or expressing such a fusion polypeptide to a therapeutic regimen that comprises administration of a pharmaceutical composition comprising (1) an inhibitor of FGFR kinase activity, (2) an antibody or antigen-binding fragment that recognizes the fusion polypeptide, (3) an antisense oligonucleotide capable of hybridization to a messenger RNA encoding a fusion polypeptide of the invention or (4) an siRNA directed to a messenger RNA encoding a fusion polypeptide of the invention.

A method of therapy that also concerns aspects of diagnosis comprises the steps of (a) taking a biopsy or fluid sample containing cancer cells or tumor circulating DNA from a subject suffering from cancer; (b) determining whether the cells in the biopsy or fluid sample contain or express a gene encoding a fusion polypeptide of the invention or express such a fusion polypeptide; (c) selecting the subject containing or expressing the gene for the fusion polypeptide or expressing the fusion polypeptide for the treatment of step d; and (d) subjecting the selected subject to a therapeutic regimen that comprises administration of a pharmaceutical composition comprising (1) an inhibitor of FGFR kinase activity, (2) an antibody or antigen-binding fragment that recognizes the fusion polypeptide, (3) an antisense oligonucleotide capable of hybridization to a messenger RNA encoding a fusion polypeptide of the invention or (4) an siRNA directed to a messenger RNA encoding a fusion polypeptide of the invention.

The FGFR kinase inhibitor used in the afore-mentioned therapy methods can be selected from the group consisting of 5-amino-1-(2-methyl-1H-benzimidazol-5-yl)-1H-pyrazol-4-yl]-(1H-indol-2-yl)-methanone, PD173074, Pazopanib, AZD4547, Ponatinib, Dovitinib, BGJ398, E-3810, JNJ-42756493, ARQ 087, LY2874455, BAY1163877, ASP5878, E7090, ODM-203, Nintedanib, TAS-120, PRN 1109 and PRN 1371. More specifically, the FGFR kinase inhibitor can be 5-amino-1-(2-methyl-1H-benzimidazol-5-yl)-1H-pyrazol-4-yl]-(1H-indol-2-yl)-methanone.

The present invention also concerns a method of characterizing a tumor in a human subject suffering from cancer, comprising assaying protein or nucleic acids of a biopsy or fluid sample containing cancer cells or tumor circulating DNA from the subject to identify the presence or absence of a gene encoding a fusion polypeptide of the invention or an expressed fusion polypeptide of the invention. In a particular embodiment, the cancer is cholangiocarcinoma.

Finally, the invention also relates to screening methods for identifying a compound having FGFR inhibitory activity. Such a method comprises (a) culturing a cell that expresses a fusion polypeptide of the invention and whose growth is dependent on this expression in the presence or absence of a test compound and determining the level of cell proliferation; (b) comparing the proliferation level of the cultured cell in the presence and absence of the test compound; and (c) judging that the test compound has FGFR inhibitory activity when the proliferation level of the cell cultured in the presence of the test compound is lower than that of the cell cultured in the absence of the test compound. The cell utilized in the method can be a cancer cell and, more specifically, a cholangiocarcinoma cell.

BRIEF DESCRIPTION OF FIGURES

FIG. 4 also shows a table summarizing IC50s obtained with the different inhibitors (D).

FIG. 5 also shows a table summarizing IC50s obtained with the different inhibitors (D).

DETAILED DESCRIPTION OF THE INVENTION

Definitions

Figure 1:
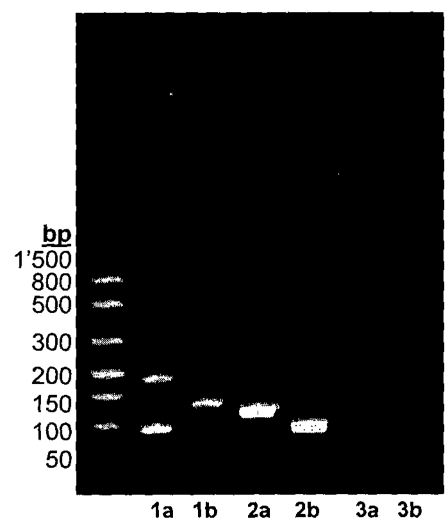
FIG. 1 shows PCR fragments amplified from cDNA from samples of two different patients, of which one has an FGFR2-VCL fusion gene (A) and the other an FGFR2-CCDC147 fusion gene (B), and visualized after agarose gel electrophoresis. Primer pairs used for amplification listed in Table 1 and in SEQ ID NOs: 8, 9-12, 14-15): 1a: primer pair 16/17, 1b: primer pair 16/18, 2a: primer pair 16/19, 2b: primer pair 16/20, 3a: primer pair 16/21, and 3b: primer pair 16/22. Fragment size standards are shown to the left of the experimental lanes.
Figure 1:
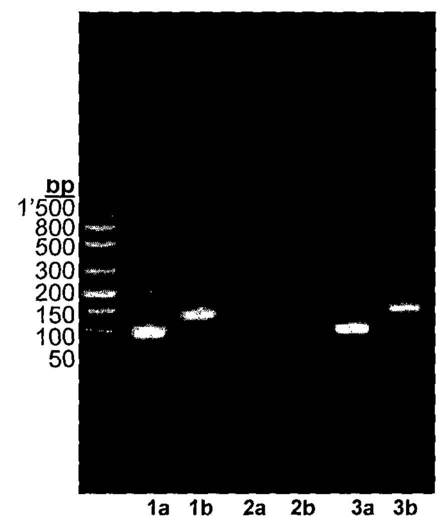

In the present application, the references used for all genomic sequences or annotation of sequences are: the Genome Reference Consortium Human Build 37 (GRCh37) and Ensembl v42 assembly (Flicek, P. et al. (2014) Nucleic Acids. Res. 42; D749-55, Database issue).

"FGFR" refers to any member of the family of fibroblast growth factor receptors. The FGFR family is a member of the receptor tyrosine kinase family. Four members of the FGFR family are known, i.e., FGFR1, FGFR2, FGFR3 and FGFR4. The FGFR as referred to in the present invention may be from any origin, but preferably from a mammal and, more preferably, from a human. The most preferred FGFR is FGFR2. The chromosomal location of the human FGFR2 gene is 10q26.

"CCDC147" refers to a polypeptide known as "coiled-coil domain containing 147". The CCDC147 gene or polypeptide as referred to in the present invention may be from any origin, but preferably from a mammal and, more preferably, from a human. Expression of the polypeptide has been observed in kidney, liver, lung and blood (platelets). The chromosomal location of the human CCDC147 gene is 10q25.1. It is noted that CCDC147 now appears on Ensembl under the name CFAP58 (cilia and flagella associated protein 58).

"VCL" refers to vinculin. Vinculin is a cytoskeletal polypeptide associated with cell-cell and cell-matrix junctions. The VCL gene or polypeptide as referred to in the present invention may be from any origin, but preferably from a mammal and, more preferably, from a human. The tail of vinculin containing a five-helix bundle is known to self-associate. See Campbell, S. (2006) Abstract: P26.00007: The chromosomal location of the human VCL gene is 10q22.2.

"Wild-type" as applied to FGFR2 nucleotide sequences (i.e., nucleotide sequences encoding a wildtype FGFR2 polypeptide) refers to any known FGFR2 nucleotide sequence capable of translation into a full-length polypeptide, in particular to any of SEQ ID NOs: 16, 22, 24, 26, 28, 38, 40, 42, 44, 46, 48, 50, 52, 54, 56, or 58 (ENST00000358487, '357555, '351936, '360144, '457416, '346997, '369056, '369058, '369061, '369059, '369060, '356226, '336553, '478859, '429361). "Wild-type" as applied to FGFR2 amino acid sequences refers to any known full-length FGFR2 polypeptide sequence, in particular to any of SEQ ID NOs: 17 (or 23), 25, 27, 29, 39, 41, 43, 45, 47, 49, 51, 53, 55, 57 or 59 (ENSP00000351276, '350166, '309878, '353262, '410294, '263451, '358052, '358054, '358057, '358055, '358056, '348559, '337665, '474011, '404219), respectively. "Wild-type" as applied to VCL nucleotide sequences (i.e., nucleotide sequences encoding a wildtype VCL polypeptide) refers to any known VCL nucleotide sequence capable of translation into a full-length polypeptide, in particular to any of SEQ ID NOs: 18, 30, 32, 34 or 60 (ENST00000211998, '372755, '417648, '436396). "Wild-type" as applied to VCL amino acid sequences refers to any known full-length VCL polypeptide sequence, in particular to any SEQ ID NOs: 19 (or 31), 33, 35 or 61 (ENSP00000211998, '361841, '411887, '415489), respectively. "Wild-type" as applied to CCDC147 nucleotide sequences (i.e., nucleotide sequences encoding a wildtype CCDC147 polypeptide) refers to any known CCDC147 nucleotide sequence capable of translation into a full-length polypeptide, in particular to SEQ ID NOs: 20, 36 or 62 (ENST00000369704, '369703). "Wild-type" as applied to CCDC147 amino acid sequences refers to any known full-length CCDC147 polypeptide sequence, in particular to SEQ ID NOs: 21 (or 37) or 63 (ENSP00000358718, '358717), respectively. In the same contexts, "mutant" refers to a sequence that differs by at least one nucleotide or one amino acid from one of the sequences of SEQ ID NOs: 16, 18, 20, 22, 24, 26, 28, 30, 32, 34, 36, 38, 40, 42, 44, 46, 48, 50, 52, 54, 56, 58, 60 or 62, or SEQ ID NOs: 17, 19, 21, 23, 25, 27, 29, 31, 33, 35, 37, 39, 41, 43, 45, 47, 49, 51, 53, 55, 57, 59, 61 or 63, respectively.

"Part of a polypeptide" refers to a polypeptide consisting of an arbitrary portion of the amino acid sequence of a full-length polypeptide.

"Fusion polypeptide" refers to a polypeptide in which the whole or a part of a wildtype or mutant FGFR polypeptide is fused to all or a part of a different polypeptide, at a location called a "fusion point". In the specific context of the present invention the term refers to a polypeptide in which the whole or a part of a wild-type or mutant FGFR2 polypeptide is fused to the whole or a part of a wild-type or mutant CCDC147 polypeptide or the whole or a part of a wild-type or mutant VCL polypeptide.

"Fusion gene" refers to a gene encoding a fusion polypeptide. A fusion gene also comprises a fusion point, also called genomic breakpoint.

"Cancer" generally refers to malignant neoplasm, which may be metastatic or non-metastatic. For instance, non-limiting examples of cancer that develops from epithelial tissues such as gastrointestinal tract and skin include brain tumor, skin cancer, head and neck cancer, esophageal cancer, lung cancer, stomach cancer, duodenal cancer, breast cancer, prostate cancer, cervical cancer, cancer of uterine body, pancreatic cancer, liver cancer, cholangiocarcinoma, gallbladder cancer, colorectal cancer, colon cancer, bladder cancer, and ovarian cancer. Non-limiting examples of sarcoma that develops from non-epithelial tissues (stroma) such as muscles include osteosarcoma, chondrosarcoma, rhabdomyosarcoma, leiomyosarcoma, liposarcoma, and angiosarcoma. Furthermore, non-limiting examples of hematological cancer derived from hematopoietic organs include malignant lymphoma including Hodgkin's lymphoma and non-Hodgkin's lymphoma, leukemia including acute myelocytic leukemia, chronic myelocytic leukemia, acute lymphatic leukemia, chronic lymphatic leukemia, and multiple myeloma.

By a "therapeutically effective amount" of an active agent, e.g., a drug substance, is meant an amount of the compound which, subsequent to single or multiple administration, confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). However, it is understood that effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific active agent employed; the specific composition employed; the age, body weight, general health, sex and diet of the patient; the time of administration, route of administration, and rate of excretion of the specific active agent employed; the duration of the treatment; drugs used in combination or contemporaneously with the specific active agent employed; and like factors well known in the medical arts.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and non-aqueous vehicles. Standard pharmaceutical carriers and their formulations are described in Remington's Pharmaceutical Sciences, Mack Publishing Co., Easton, Pa., 19th ed. 1995.

"Specifically binding to" or "specifically hybridizing to" means that two oligo- or polynucleotides interact with one another but not detectably with any different oligo- or polynucleotide under the given conditions, or, if conditions are not given, under adequate conditions that can be identified based on knowledge in the art.

An exon is any nucleotide sequence encoded by a gene that remains present within the final mature RNA product of that gene after introns have been removed by RNA splicing. The term "exon" refers to both the DNA sequence within a gene and to the corresponding sequence in RNA transcripts and cDNAs derived therefrom. For the purposes of the present application, the numbering of exons starts with exon number 1 which contains 5' untranslated sequences. It is noted that the cDNAs of SEQ ID NOs: 16, 18 and 20 include untranslated sequences, whereas SEQ ID NOs: 22, 24, 26, 28, 30, 32, 34, 36, 38, 40, 42, 44, 46, 48, 50, 52, 54, 56, 58, 60, 62 as well as the subsequences of SEQ ID NOs: 64-72 only contain polypeptide-coding sequences. It is further noted that the exon annotation is performed on the basis of the longest coding transcript found in Ensembl v42 assembly for each part of a fusion gene, i.e. SEQ ID NO: 16 for FGFR2, SEQ ID NO: 18 for VCL and SEQ ID NO: 20 for CCDC147.

As used herein, "cDNA" refers to a partial or complete copy of a gene transcript. The term is meant to encompass the latter copy, its complement as well as the double-stranded DNA consisting of both copy and complement.

The present invention relates to novel fusion polypeptides that are expressed in certain human cancer cells but not in normal cells. More specifically, it relates to fusion polypeptides comprising an FGFR2 polypeptide and a CCDC147 polypeptide or a VCL polypeptide, wherein the FGFR2 polypeptide is the whole or a part of a wildtype FGFR2 polypeptide, or the whole or a part of a mutant FGFR2 polypeptide having one or more amino acid substitutions, deletions, or insertions with respect to the wildtype polypeptide; the CCDC147 polypeptide is the whole or a part of a wildtype CCDC147 polypeptide, or the whole or a part of a mutant CCDC147 polypeptide having one or more amino acid substitutions, deletions, or insertions with respect to the wildtype polypeptide; and the VCL polypeptide is the whole or a part of a wildtype VCL polypeptide, or a part of a mutant VCL polypeptide having one or more amino acid substitutions, deletions, or insertions with respect to the wildtype polypeptide, wherein claimed fusion polypeptides are recombinant polypeptide, are isolated from cancer cells that are propagated in vitro or as xenografts, or are isolated from human cholangiocarcinomas. Taking into account SEQ ID NOs, the invention relates to novel fusion polypeptides comprising an FGFR2 polypeptide and a CCDC147 polypeptide or a VCL polypeptide, whereby the FGFR2 polypeptide is the whole or a part of a wildtype polypeptide having the amino acid sequence of any of SEQ ID NOs: 17, 25, 27, 29, 39, 41, 43, 45, 47, 49, 51, 53, 55, 57 or 59, or the whole or a part of a mutant polypeptide having one or more amino acid substitutions, deletions, or insertions with respect to the wildtype polypeptide; the CCDC147 polypeptide is the whole or a part of a wildtype polypeptide having the amino acid sequence of SEQ ID NOs: 21 or 63, or the whole or a part of a mutant polypeptide having one or more amino acid substitutions, deletions, or insertions with respect to the wildtype polypeptide; and the VCL polypeptide is the whole or a part of a wildtype polypeptide having the amino acid sequence of any of SEQ ID NOs: 19, 33, 35 or 61, or the whole or a part of a mutant polypeptide having one or more amino acid substitutions, deletions, or insertions with respect to the wildtype polypeptide. Preferably, the latter amino acid substitutions, deletions, or insertions affect (i.e. substitute, add or delete) 1-10 amino acids, more preferably 1-5 amino acids and most preferably 1-2 amino acids, in a polypeptide sequence or a fragment of a polypeptide sequence present in the fusion polypeptide. Mutant FGFR2, CCDC147 or VCL polypeptides also encompass FGFR2, CCDC147 or VCL polypeptides having 70% or more identity, preferably 80% or more identity, more preferably 90% or more identity and even more preferably 95% or more identity with the respective wild-type polypeptides or fragments thereof. Most preferably, mutant polypeptides have at least 97%, at least 98% or at least 99% identity with the respective wild-type polypeptides or fragments thereof.

The identity of an amino acid sequence (or a nucleotide sequence) relative to another can be determined using the algorithm BLAST. Karin and Altschul (1993) Proc. Natl. Acad. Sci. USA 90: 5873-7. Programs such as BLASTN and BLASTX were developed based on this algorithm. Altschul. Et al. (1990) J. Mol. Biol. 215: 403-10. To analyze nucleotide sequences according to BLASTN, parameters for score can be set at 100, and wordlength at 12. When analyzing amino acid sequences using BLASTX, score can be at 50 and wordlength at 3. Default parameters can be used when using the BLAST and Gapped BLAST programs. Specific techniques for such analyses are known in the art. Reference is made to the information on the website of the National Center for Biotechnology Information (NCBI), Basic Local Alignment Search Tool (BLAST).

The present invention also encompasses fusion polypeptides comprising an FGFR2 polypeptide and a CCDC147 polypeptide or a VCL polypeptide, wherein the FGFR2 polypeptide is the whole or a part of an FGFR2 polypeptide identifiable in a mammalian animal proteome, or the whole or a part of a mutant polypeptide that differs from the latter polypeptide by one or more amino acid substitutions, deletions, or insertions; the CCDC147 polypeptide is the whole or a part of a CCDC147 polypeptide identifiable in a mammalian animal proteome, or the whole or a part of a mutant polypeptide that differs from the latter polypeptide by one or more amino acid substitutions, deletions, or insertions; and the VCL polypeptide is the whole or a part of a VCL polypeptide identifiable in a mammalian animal proteome, or the whole or a part of a mutant polypeptide that differs from the latter polypeptide by one or more amino acid substitutions, deletions, or insertions.

The present invention further relates to polynucleotides encoding fusion polypeptides. More specifically, it relates to a polynucleotide, such as a cDNA, encoding a fusion polypeptide comprising an FGFR2 polypeptide and a CCDC147 polypeptide or a VCL polypeptide, wherein the polynucleotide combines a first polynucleotide encoding the whole or a part of a wildtype FGFR2 polypeptide or a mutant polynucleotide derived therefrom by substitution, deletion or insertion of one or more codons; and a second polynucleotide encoding the whole or a part of a wildtype CCDC147 polypeptide or VCL polypeptide or a mutant polynucleotide derived therefrom by substitution, deletion or insertion of one or more codons. Taking into account SEQ ID NOs, the present invention relates to a polynucleotide (cDNA) encoding a fusion polypeptide comprising an FGFR2 polypeptide and a CCDC147 polypeptide or a VCL polypeptide, wherein the polynucleotide combines a first polynucleotide encoding the whole or a part of a wildtype FGFR2 polypeptide, the first polynucleotide encompassing all or part of the nucleotide sequence of any of SEQ ID NOs: 16, 22, 24, 26, 28, 38, 40, 42, 44, 46, 48, 50, 52, 54, 56 or 58, or a nucleotide sequence derived from any of SEQ ID NOs: 16, 22, 24, 26, 28, 38, 40, 42, 44, 46, 48, 50, 52, 54, 56 or 58 by substitution, deletion or insertion of one or more codons; and a second polynucleotide encoding the whole or a part of a wildtype CCDC147 polypeptide or VCL polypeptide, the second polynucleotide encompassing all or part of the nucleotide sequence of any of SEQ ID NOs: 20, 36 or 62, or any of SEQ ID NOs: 18, 30, 32, 34 or 60, or a nucleotide sequence derived from the nucleotide sequence of any of SEQ ID NOs: 20, 36 or 62, or any of SEQ ID NOs: 18, 30, 32, 34 or 60 by substitution, deletion or insertion of one or more codons. Preferably, the latter substitutions, deletions, or insertions of codons in the nucleotide sequences encoding FGFR2, CCDC147 or VCL affect (i.e. substitute, add or delete) 1-10 amino acids, more preferably 1-5 amino acids and most preferably 1-2 amino acids in the encoded polypeptide or the fragment of the polypeptide present in the fusion polypeptide. The polynucleotides of the invention also include polynucleotides that encode FGFR2, CCDC147 or VCL polypeptides independently having 70% or more identity, preferably 80% or more identity, more preferably 90% or more identity and even more preferably 95% or more identity with the respective wild-type polypeptides or fragments thereof. Most preferably, the derived polynucleotides encode polypeptides or fragments thereof that have at least 97%, at least 98% or at least 99% identity with the respective wildtype polypeptides or fragments thereof.

Polynucleotides of the present invention can be obtained by any method. They include, e.g., all cDNAs prepared from messenger RNAs (mRNAs), DNAs derivatized from genomic DNAs, DNAs prepared by chemical synthesis, DNAs obtained by polymerase chain reaction (PCR) amplification from RNA or DNA templates as well as DNAs prepared by a combination of the latter methods. Non-genomic-type polynucleotides encoding fusion polypeptides of the present invention can be obtained by synthesis of cDNA from mRNA encoding a fusion polypeptide, by isolation of a genomic DNA fragment followed by removal of intervening sequences from the fusion polypeptide-coding region, or by chemical synthesis using a method known in the art.

To provide an example, total RNA may be prepared from cells or tissues expressing a fusion polypeptide of the invention. Total RNA may be obtained, e.g., by the guanidine-isothiocyanate method, the hot phenol method or the acid guanidinium thiocyanate-phenol-chloroform method. Messenger RNA may be selected by affinity chromatography on oligo(dT) cellulose, polyU Sepharose or the like. Using such mRNA as a template, cDNA synthesis can be carried out using a known method, e.g., using the reverse transcriptase reaction. Mol. Cell. Biol. 2: 161 (1982); Mol. Cell. Biol. 3: 280 (1983); Gene 25: 263 (1983). Subsequent to second strand synthesis, the double-stranded cDNA is inserted into a vector such as a plasmid, a phage, a cosmid or the like. The resulting library is then introduced into appropriate host cells, e.g., *E. coli*, and screened for the presence in a host cell of a vector carrying a cDNA for a fusion polypeptide of the invention using methods known in the art, e.g., colony hybridization.

The present invention also encompasses vectors carrying a polynucleotide encoding a fusion polypeptide of the invention. The vectors are not particularly limited, provided they replicate or amplify autonomously in a prokaryotic or eukaryotic host cell. Polynucleotides of the invention may be introduced into vectors using standard molecular biology techniques. Vectors include *E. coli*-derived plasmids such as pBR322, pBR325, pUC12. pUC13, pUC19, yeast (e.g., *S. cerevisiae*)-derived plasmids such as the pYC vectors or pRS shuttle vectors, and *Bacillus subtilis*-derived plasmids such as pUB110, pTP5 or pC194. Viral vectors include bacteriophage vectors such as λgt10 and λgt11, and insect or animal virus vectors derived from nuclear polyhedrosis virus, retroviruses including lentiviruses, vaccinia virus, etc.

The invention also relates to expression vectors that allow for insertion of a polynucleotide of the invention and expression of a fusion polypeptide of the invention in a prokaryotic or eukaryotic host. Suitable expression vectors include pEF-BOS (Nucleic Acids Res. 18: 5322 (1990)) and pME18S-FL (Addgene plasmid repository database, www.addgcnc.org, Mar. 7, 2014). Fusion polypeptides of the present invention can also be expressed as (further) fusions with other polypeptides. Plasmid pGEX4T1 is suitable for production of a fusion polypeptide as a fusion with glutathione S-transferase sequences. Using an appropriate vector, a fusion polypeptide of the invention can also be expressed, e.g., as fusion with influenza hemagglutinin, immunoglobulin constant region, β-galactosidase, or maltose-binding protein (e.g. using a pMAL C2 vector). Fusions with various peptides are also encompassed, such as fusions with FLAG (Hopp, T. P. et al. (1988) BioTechnology 6: 1204-10), 6×His consisting of 6 histidine residues, 10×His, influenza hemagglutinin fragments, fragments of human c-myc, fragments of VSV-GP, fragments of p18 HIV, T7-tag, HSV-tag, E-tag, fragments of SV40 T antigen, Ick tag, fragments of α-tubulin, B-tag, fragments of Protein C, Stag, StrepTag and HaloTag.

It is understood that expression vectors contain all elements required for efficient transcription and translation of a cDNA gene for a fusion polypeptide of the invention, including elements such as promoters, transcriptional and translational enhancers, start/stop codons for translation, ribosome binding site signal, transcription termination signal, polyadenylation site, signal for secretion of fusion polypeptide into the medium (or periplasmic space), etc., as well as for replication. Furthermore, vectors may contain marker genes (genes for amplification, drug resistance genes, etc.) that enable selection of transformed hosts or hosts with gene amplification. Example promoters include the *E. coli* Trp, lac, recA, IPL, Ipp and tac promoters, the yeast PH05, PGK, GAP and ADH promoters, the *B. subtilis* SL01, SP02 and penP promoters and the mammalian SV40, retroviral and heat shock promoters. Example marker genes include the dihydrofolate reductase gene, thymidine kinase gene, neomycin resistance gene, glutamate synthase gene, adenosine deaminase gene, ornithine decarboxylase gene, hygromycin-B-phosphotransferase gene, and aspartate transcarbamylase gene. A polynucleotide of the invention may be introduced into an expression vector using standard molecular biology techniques.

The present invention further relates to recombinant cells transformed with vectors including expression vectors carrying a polynucleotide of the invention. There is no particular limitation as to cell types that may be so transformed. Preferred are *E. coli* and animal, including in particular mammalian, cells. Examples of *E. coli* cells are DH5a, TB1 and HB101, of mouse cells are COP, L, C127, Sp2/0, NS-1 and NIH3T3 cells, of rat cells are PC12 and PC12h, of hamster cells are BHK and CHO, of monkey cells are COS1. COS3, COS7, CV1 and Vero, and of human cells are HeLa cells, diploid fibroblast-derived cells, myeloma cells and HepG2 cells. Methods for introducing vectors into host cells were described in Proc. Natl. Acad. Sci. USA 69: 2110 (1972); Mol. Gen. Genet. 168: 111 (1979); J. Mol. Biol. 56: 209 (1971); Proc. Natl. Acad. Sci. USA 75: 1927 (1978); J. Bacteriol. 153: 163 (1983); Virology 52: 456 (1973); Mol. Cell. Biol. 3: 2156 (1983).

Fusion polypeptide of the invention can be produced by culturing recombinant cells as described immediately before, preferably animal including mammalian animal or human cells, and, provided that the cells are capable of secreting the polypeptide, thereafter collecting the culture medium from which cells and cell debris are removed by filtration or centrifugation. Fusion polypeptide can then be purified by conventional methods such as methods based on solubility, e.g., salting out and solvent precipitation, methods based on molecular size, e.g., dialysis, ultrafiltration, gel filtration, and native and SDS-PAGE, methods based on charge, e.g., ion exchange chromatography and hydroxyapatite chromatography, affinity-based methods, e.g., affinity column chromatography, methods exploiting hydrophobicity, e.g., reverse phase high performance liquid chromatography, and methods based on isoelectric differences between polypeptides, e.g., isoelectric focusing.

When fusion polypeptide produced in the recombinant cells is accumulating in the cytoplasm/nucleoplasm or in the periplasm of walled recombinant cells, cells are collected by methods such as filtration or centrifugation. After suspension of the cells in an appropriate buffer, the cell wall or cell membrane, respectively, is disrupted by methods such as sonication, lysozyme treatment or cryolysis, and a membrane or cytoplasmic/nucleoplasmic fraction is obtained after centrifugation or filtration. Fusion polypeptide is then purified by the biochemical methods described immediately before.

The present invention also encompasses oligonucleotides that hybridize to polynucleotides of the invention. Pairs of sense and antisense oligonucleotides that are complementary to sequences within a polynucleotide of the invention are useful as primers for the amplification of the polynucleotide or parts thereof by PCR. Oligonucleotide primers that are complementary to a polynucleotide of the invention can be of any length. Preferably, they contain a sequence of at least 12 consecutive nucleotides, more preferably 12-50 consecutive nucleotides and most preferably 18-30 consecutive nucleotides. Typically, such oligonucleotides have no internal secondary structure, have a G/C content of between 40 and 60% and have a balanced distribution of G/C and NT rich domains. When oligonucleotides are used in hybridization procedures, preference increases with the length of their sequence. Hence, oligonucleotides of >300 consecutive nucleotides are preferred over those of >200 consecutive nucleotides, which are preferred over oligonucleotides of >100 consecutive nucleotides. Oligonucleotides of >100 consecutive nucleotides are preferred over those of >50 consecutive nucleotides which are preferred over oligonucleotides of 20 to 50 consecutive nucleotides.

Also encompassed are oligonucleotides that are complementary to a portion of an mRNA sequence encoding a fusion polypeptide of the invention. Such oligonucleotides can function as antisense oligonucleotides, ribozymes or small interfering RNAs (siRNAs). Antisense oligonucleotides bind target mRNAs or genomic DNA and inhibit their translation or transcription, respectively. Antisense oligonucleotides containing a sequence of 5-70 consecutive nucleotides are preferred over those containing 5-100 consecutive nucleotides: More preferred are oligonucleotides containing 5-50 consecutive nucleotides. Even more preferred are antisense oligonucleotides that contain 5-30 consecutive nucleotides. Antisense oligonucleotides can be modified to enhance their stability in blood, resistance to degradation or absorption in the digestive tract, or membrane permeability. Modifications of phosphate bonds include conversion of one or more bonds to phosphodiester, phosphorothioate, phosphorodithioate, methyl phosphonate, phosphoroamidate, non-phosphate bonds or phosphonothionate bonds. Ribose may be converted to 2'-fluororibose or 2'-O-methylribose. Modified nucleotide bases include 5-propynyluracil and 2-aminoadenine. siRNAs typically are double-stranded RNAs (dsRNAs) of 10-25 nucleotides in length that are capable of RNA interference. Bass (2001) Nature 411: 428-429; Elbashir et al. (2001) Nature 411: 494-98. Like antisense oligonucleotides, siRNAs can also comprise chemically modified nucleotides and non-nucleotides. The more recently described single-stranded siRNAs are also encompassed herein. Lima, W. F. et al. (2012) Cell 150: 883-894; Yu, D. et al. (2012) Cell 150: 895-908.

In a specific embodiment, an oligonucleotide of the present invention used in hybridization procedures (i.e., as oligonucleotide probe) is complementary to a region that is composed of sequences from both fusion partners, i.e., from FGFR2 and from CCDC147 or VCL. In a more specific embodiment, it is complementary to a region comprising the fusion point. In another specific embodiment, one primer of a primer pair used for amplification of a polynucleotide of the invention or a part thereof is identical or complementary to FGFR2 sequences, whereas the other primer is identical or complementary to VCL or CCDC147 sequences.

The present invention also relates to antibodies and antigen-binding fragments that bind to any part of a fusion polypeptide of the invention. The invention is not limited to any particular type of antibody. Antibodies of the invention may be any antibody, from any mammalian source, and either polyclonal or monoclonal. Methods for the production of mammalian monoclonal antibodies, e.g., mouse monoclonal antibodies, have long been established and are widely practiced by persons skilled in the art. Kohler and Milstein (1981) Meth. Enzymol. 73: 3-46. Preferred antibodies for administration to human subjects are chimeric antibodies, humanized antibodies and human antibodies. They are preferred because they do not provoke, or provoke less, human host immune responses as opposed to, e.g., antibodies from a mammalian animal such as a mouse. Methods for preparing chimeric antibodies containing human constant regions and variable regions from a mammalian animal are well known in the art. Carl, A. K. et al. “Therapeutic monoclonal antibody”, published in the U.K. by McMillan Publishers LTD., 1990. The same is true for humanized antibodies. Patent publications EP 125023; WO 96/02576; WO 98/13388; EP 239400; WO 96/02576. Techniques for directly producing humanized antibodies by introducing complementarity-determining regions (CDR) sequences from an animal antibody gene into a human antibody template gene have also been described. There exist several well-known approaches for obtaining human antibodies.

Human monoclonal antibodies can be produced by immunization of human lymphocytes in vitro followed by fusion to a human lymphoblastoid cell line. Antibodies can then be produced from the resulting fusion cells by biotechnological methods. Borrebaek et al. (1988) Proc Natl. Acad. Sci. USA 85: 3995-9. A human antibody can also be obtained from immunization of a transgenic animal carrying an entire repertoire of human antibody genes. International publications nos. WO 2003/12227; WO 92/03918; WO 94/02602; WO 94/25585; WO 96/34096 and WO 96/33735. In another approach, human B cells expressing an antibody against a fusion polypeptide of the invention can be selected using a suitable approach such as flow cytometry. The nucleotide sequence of the antibody can then be determined. Jin et al. (2009) Nat. Med. 15: 1088-92; Scheid et al. (2009) Nature 458: 636-40; Wrammert et al. (2008) Nature 453: 667-72; Tiller et al. (2008) J. Immunol. Meth. 329: 112-24. This information is subsequently used to obtain DNA sequences encoding the antibody, construct an appropriate expression vector and produce the antibody by biotechnological methods. International publications nos. WO 92/01047; WO 92/20791; WO 93/06213; WO 93/11236; WO 93/19172; WO 95/01438 and WO 95/15388. Another approach involves panning of a human antibody phage display library, in which single chain human antibodies (human scFv) are displayed on the surfaces of bacteriophages. Subsequent to determination of the nucleotide sequence encoding a selected scFv, a complete antibody gene can be constructed and expressed in a suitable producer cell. International publications nos. WO 92/01047; WO 92/20791; WO 93/06213; WO 93/11236; WO 93/19172; WO 95/01438 and WO 95/15388.

The antibodies of the invention include divalent antibodies as represented by IgG as well as monovalent antibodies as represented by IgM. Bi-specific antibodies binding to two different antigens are also encompassed. Also encompassed are chimeras of an antibody and a toxic product or polypeptide. Antibodies of the invention also include antigen-binding fragments such as minibodies. Minibodies comprise only a portion of an antibody, typically including six CDR sequences. Specific examples of minibodies include Fab, Fab', F(ab')2, Fv, scFv (single chain Fv), diabodies, and sc(Fv)2 (single chain (Fv)2), and multimers thereof. For the production of antigen-binding molecule fragments, see Co et al., (1994) J. Immunol. 152: 2968-76; Better and Horwitz (1989) Meth. Enzymol. 178: 476-96; Plueckthun and Skerra (1989) Meth. Enzymol. 178: 476-96; Lamoyi (1989) Meth. Enzymol. 121: 652-63; Rousseaux et al. (1989) Meth. Enzymol. 121: 663-69; Bird et al. (1991) TIBTECH 9: 132-7. For diabodies see Holliger et al. (1993) Proc. Natl. Acad. Sci. USA 90: 6444-8; patent publications EP 404,097 and WO 93/11161. For scFv antibodies, see Huston et al., (1988) Proc. Natl. Acad. Sci. U.S.A. 85, 5879-83; Plickthun “The Pharmacology of Monoclonal Antibodies” Vol. 113, eds., Resenburg and Moore, Springer Verlag, New York, pp. 35 269-315 (1994). sc(Fv)2 is a single-chain minibody produced by linking two VHs and two VLs using linkers and such (Hudson et al. (1999) J Immunol. Methods 231: 177-89). Also encompassed are antibody-drug conjugates (ADC), wherein the antibodies of the present invention are linked to cytotoxic agents, e.g. via linkers.

In specific embodiments, the antibodies and antigen-binding fragments of the present invention bind to an epitope that is composed of sequences from both fusion partners, i.e., from FGFR2 and from CCDC147 or VCL. In further specific embodiments, they bind to an epitope that comprises the fusion point.

The present invention further relates to the treatment of diseases or conditions, notably including cancer, in which affected tissues express a fusion polypeptide of the invention. Treatment can involve a regimen of administration of a therapeutically effective amount of an active agent. An active agent can be an antibody or antigen-binding fragment that binds to a fusion polypeptide of the invention, an antisense RNA or siRNA molecule directed towards fusion polypeptide mRNA (or gene) or an inhibitor of the kinase activity of the fusion polypeptide.

The present invention also concerns pharmaceutical compositions comprising an antibody or antigen-binding fragment that binds to a fusion polypeptide of the invention. For example, anti-FGFR2 antibodies include BAY1179470 (Kopitz C. et al. (2014) Cancer Res 74 (Suppl. 19) 7445—Abstract DDT02-01) and FPA144 (Gemo A T. et al. (2014) Cancer Res 74 (Suppl. 19)—Abstract 5446). ADC directed against FGFR2 includes BAY1187982 (Sommer A. et al. (2014) Cancer Res. 74 (Suppl. 19)—Abstract 4491). The latter compositions will be preferentially administered parenterally, but transnasal, transpulmonary or transdermal delivery is also envisaged. The pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated agent or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

The dose of a pharmaceutical composition containing an antigen-binding molecule may be, for example, from 0.01 to 30 mg/kg for each administration. Alternatively, the cumulative dose may be, for example, from 0.001 to 100,000 mg per subject. However, the present invention is not limited by the numeric values described above. The doses and administration methods vary depending on the subject's weight, age, symptoms, and such. Those skilled in the art can set appropriate doses and administration methods in consideration of the factors described above.

The present invention also relates to pharmaceutical compositions comprising an antisense RNA or siRNA molecule directed towards an mRNA encoding a fusion polypeptide of the invention. In specific embodiments, the antisense RNA or siRNA molecule is directed towards a sequence that is composed of sequences from both fusion partners, i.e., from FGFR2 and from CCDC147 or VCL, or even more specifically to a sequence encompassing the fusion point. Pharmaceutical compositions containing dsRNAs were described, e.g., in EP patent nos. 1144623 and 1214945, and US patent no. 8'546'143. The same principles are taken to also relate to antisense RNA or to the more recently discovered single stranded siRNAs (ss siRNAs). Juliano, R. et al. (2008) Nucleic Acids Res. 36: 4158-71; Lima et al. (2012); Yu et al. (2012).

Pharmaceutical compositions containing dsRNAs may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the pharmaceutical compositions containing dsRNAs will generally be in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions containing dsRNAs will generally be in the form of sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Although microinjection, lipofection, viruses, viroids, capsids, capsoids, or other auxiliary agents may be required to efficiently introduce dsRNA into cell cultures, these methods and agents are not required for uptake of dsRNA in vivo. It is observed that the same is true for antisense RNAs and ss siRNAs. Juliano et al. (2008); Davidson, B. L. & Monteys, A. M. (2012) Cell 150: 873-5.

Pharmaceutical compositions containing dsRNAs in the form of aqueous suspensions may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The pharmaceutical compositions containing dsRNAs also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

Methods for preparation of such formulations will be apparent to those skilled in the art. Suitable polymer materials can be obtained, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811; international patent publication WO 91/06309; and European patent publication EP-A-43075, all of which are incorporated by reference herein.

The present invention further relates to pharmaceutical compositions comprising an inhibitor of the FGFR tyrosine kinase activity of a fusion polypeptide of the invention. Any inhibitor of FGFR kinase activity may be employed. Inhibitors include the inhibitory aminopyrazole derivatives and their pharmaceutically acceptable salts described in international patent publication WO 2011/016528, in particular 5-amino-1-(2-methyl-1H-benzimidazol-5-yl)-1H-pyrazol-4-yl]-(1H-indol-2-yl)-methanone (CAS 1265229-25-1, herein referred to as Compound A). They further include inhibitors PD173074 (Mohammadi et al. (1998) EMBO J. 17: 5896-904), Pazopanib (Harris et al. (2009) J. Med. Chem. 51: 4632-40; Keisner and Shah (2011) Drugs 71: 443-54), AZD4547 (Gavine et al. (2012) Cancer Res. 72: 2045-56), Ponatinib (or AP24534) (Huang et al. (2010) J. Med. Chem. 53: 4701-19), Dovitinib (Trudel et al. (2005) Blood 105: 2941-8; Man et al. (2014) J. Cell. Mol. Med. 18: 143-55), BGJ398 (Guagnano et al. (2011) J. Med. Chem. 54:

7066-83), E-3810 also known as Lucitanib (Bello et al. (2011) Cancer Res. 71: 1396-405), JNJ-42756493 (Squires et al. (2008) AACR Abstract 1545), ARQ 087 (Yu et al. (2011) Cancer Res. 71 (Suppl. 1) 3671), LY2874455 (Zhao G et al. Mol Cancer Ther. (2011) November; 10(11):2200-10), BAY1163877 (Heroult et al. (2014) Cancer Res. 74 (Suppl. 19)—Abstract 1739), ASP5878 (73rd Annual Meeting of the Japanese Cancer Association (2014)—Abstract/Poster 1411), E7090 (Saori Watanabe Miyano et al. (2015) AACR Abstract 770), ODM-203 (Holmstrom T. et al. 26th ENA Symposium (2014) Eur. J. Cancer 50(S6):142—Abstract 432), Nintedanib (Roth G J et al. J Med Chem. (2015) February 12; 58(3):1053-63), TAS-120 (Ochiiwa, H. et al. (2013) AACR; Mol. Cancer Ther. 12(11 Suppl) Abstract A270), PRN 1109 and PRN 1371 (both in: Phan V T. et al. 26th ENA Symposium (2014) Eur. J. Cancer 50(S6):157—Abstract 483).

A particularly preferred inhibitor is Compound A.

The pharmaceutical compositions of this invention comprising an inhibitor of the FGFR tyrosine kinase activity (also referred to below as "drug substance") may be administered orally, parenterally, by inhalation spray, topically, rectally, nasally, buccally, vaginally or via an implanted reservoir, preferably by oral administration or administration by injection. The pharmaceutical compositions may contain any conventional non-toxic pharmaceutically acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to drug substance, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating a drug substance in the form of a sterile solid composition which can be dissolved or dispersed in sterile water or other sterile injectable medium prior to use.

In order to prolong the effect of a drug substance, it is often desirable to slow the absorption of the drug substance from subcutaneous or intramuscular injection. This may be accomplished by the use of a liquid suspension of crystalline or amorphous material with poor water solubility. The rate of absorption of the drug substance then depends upon its rate of dissolution, which, in turn, may depend upon crystal size and crystalline form. Alternatively, delayed absorption of a parenterally administered drug form is accomplished by dissolving or suspending the drug substance in an oil vehicle. Injectable depot forms are made by forming microencapsule matrices of the drug substance in biodegradable polymers such as polylactide-polyglycolide. Depending upon the ratio of drug substance to polymer and the nature of the particular polymer employed, the rate of drug release can be controlled. Examples of other biodegradable polymers include poly(orthoesters) and poly(anhydrides). Depot injectable formulations are also prepared by entrapping the drug substance in liposomes or microemulsions that are compatible with body tissues.

Compositions for rectal or vaginal administration are preferably suppositories which can be prepared by mixing drug substance with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders and granules. In such solid dosage forms, drug substance is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of drug substance include ointments, pastes, creams, lotions, gels, powders, solutions, sprays, inhalants or patches. Drug substance is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to drug substance, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the drug substance, excipients such as lactose, talc, silicic acid, aluminum hydroxide, calcium silicates and polyamide powder, or mixtures of these substances. Sprays can additionally contain customary propellants such as chlorofluorohydrocarbons or environmentally friendlier propellents such as hydrofluoroalkane, C3-C6 light saturated hydrocarbons, dimethyl ether, and the like.

Transdermal patches have the added advantage of providing controlled delivery of drug substance to the body. Such dosage forms can be made by dissolving or dispensing the drug substance in the proper medium. Absorption enhancers can also be used to increase the flux of the drug substance across the skin. The rate can be controlled by either providing a rate-controlling membrane or by dispersing the compound in a polymer matrix or gel.

For pulmonary delivery, a pharmaceutical composition of the invention is formulated and administered to the patient in solid or liquid particulate form by direct administration e.g., inhalation into the respiratory system. Solid or liquid particulate forms of the drug substance prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al, and international patent publication WO 98/43650, all of which are incorporated herein by reference). A discussion of pulmonary delivery of antibiotics is also found in U.S. Pat. No. 6,014,969, incorporated herein by reference.

In general, treatment regimens according to the present invention comprise administration to a human subject in need of such treatment from 0.1 mg to 1000 mg of drug substance (i.e., an inhibitor of FGFR tyrosine kinase activity) per day in single or multiple doses. Single dose compositions may contain such amounts or submultiples thereof to make up the daily dose.

The drug substance can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, every 4 to 120 hours, or according to the requirements of the particular drug substance. The methods herein contemplate administration of an effective amount of drug substance or pharmaceutical composition comprising the drug substance to achieve the desired or stated effect. Typically, the pharmaceutical compositions will be administered from 1 to 6 times per day or alternatively, as a continuous infusion. Such administration can be used as a chronic or acute therapy. The amount of drug substance that may be combined with pharmaceutically acceptable excipients or carriers to produce a single dosage form will vary depending on the particular mode of administration and, possibly, on the subject treated. A typical preparation will contain from 5% to 95% drug substance (w/w). Alternatively, such preparations may contain from 20% to 80% drug substance. Lower or higher doses than those recited above may be required. Specific dosage and treatment regimens for any particular subject will depend upon a variety of factors, including the activity of the specific drug substance employed, the age, body weight, general health status, sex, diet, time of administration, rate of excretion, drug combination, the severity and course of the disease, condition or symptoms, the subject's disposition to the disease, condition or symptoms, and the judgment of the treating physician.

The present invention also relates to methods for detecting a fusion polypeptide of the invention or a polynucleotide encoding the fusion polypeptide in a sample from a human or animal subject, e.g., tumor tissue, normal tissue, and various body fluid specimens containing cancer or normal cells or tumor circulating DNA (blood, serum, urine, saliva, etc.).

Fusion polypeptides of the invention typically can be detected by contacting a sample from the subject with one of the above-described antibodies or antigen-binding fragments and then detecting the presence or absence of a reaction product. The step of detecting the reaction product may be carried out with any suitable immunoassay.

Immunoassays carried out in accordance with the present invention may be homogeneous assays or heterogeneous assays. In a homogeneous assay, the immunological reaction usually involves the specific fusion polypeptide antibody or antigen-binding fragment, a labeled analyte, and the sample of interest. The signal arising from the label is modified, directly or indirectly, upon the binding of the antibody/antigen-binding fragment to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody/antigen-binding fragment, and means for producing a detectable signal. Samples as described above may be used. The antibody/antigen-binding fragment can be immobilized on a support, such as a bead (such as protein A agarose, protein G agarose, latex, polystyrene, magnetic or paramagnetic beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are immunoblotting, immunoprecipitation, immunofluorescence methods, chemiluminescence methods, electrochemiluminescence or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No.

4,727,022 to Skold et al. titled "Methods for Modulating Ligand-Receptor Interactions and their Application", U.S. Pat. No. 4,659,678 to Forrest et al. titled "Immunoassay of Antigens", U.S. Pat. No. 4,376,110 to David et al., titled "Immunometric Assays Using Monoclonal Antibodies", U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling" and U.S. Pat. No. 4,230,797 to Boguslaski et al., titled "Heterogenous Specific Binding Assay Employing a Coenzyme as Label".

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein) in accordance with known techniques.

The presence or absence of a gene or mRNA encoding a fusion polypeptide of the present invention in a sample from a subject can be tested and determined, for example, by conventional methods using the above-described various oligonucleotides (a pair of oligonucleotide primers, oligonucleotide probes, etc.) of the present invention and mRNA, cDNA prepared using mRNA as a template, genomic DNA, or such in a sample (tumor tissue, normal tissue, and various body fluid specimens containing cancer or normal cells or circulating nucleic acids (blood, serum, urine, saliva, etc.)) collected from a subject. Such gene analysis methods include, for example, Northern blotting as well as numerous techniques enumerated below:

(1) Polynucleotide-based detection methods (i.e., see U.S. Pat. Nos. 5,310,625, 5,322,770, 5,561,058, 5,641,864, and 5,693,517; see also Myers and Sigua, Amplification of RNA: High-temperature reverse transcription and DNA amplification with *Thermus thermophilus* DNA polymerase. In: M. A. Innis, D. H. Gelfand and J. J. Sninsky, Eds., PCR Strategies, Academic Press, San Diego (1995), pp. 58-68, DNA sequencing methods (i.e., Sequencing methods by PE Biosystems (Foster City, Calif.); see Sanger et al. (1977) Proc. Natl. Acad. Sci. USA 74: 5463-5467).

(2) Amplification-based identification methods (i.e., U.S. Pat. Nos. 4,683,195, 4,683,202 and 4,965,188; see PCR Applications (1999) Innis et al., eds., Academic Press, San Diego; PCR Strategies (1995) Innis et al., eds, Academic Press, San Diego; PCR Protocols (1990) Innis et al., eds., Academic Press, San Diego; and PCR Technology (1989) Erlich, ed., Stockton Press, New York, N.Y.).

(3) Ligase chain reaction (Wu and Wallace (1988) Genomics 4: 560-569); the strand displacement assay (Walker et al. (1992) Proc. Natl. Acad. Sci. USA 89: 392-396 and Nucleic Acids Res. 20: 1691-1696; and U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al. (1989) Proc. Natl. Acad. Sci USA 86: 1173-1177); and self-sustained sequence replication (3SR) (Guetelli et al. (1990) Proc. Natl. Acad. Sci USA 87: 1874-1878 and WO 1992/08800).

(4) Sequence-specific amplification or primer extension methods (i.e., U.S. Pat. Nos. 5,137,806; 5,595,890; 5,639,611 and 4,851,331).

(5) Kinetic PCR methods (i.e., Higuchi et al. (1992) Bio/Technology 10: 413-417; Higuchi et al. (1993) Bio/Technology 11: 1026-1030; Higuchi and Watson, in PCR Applications, supra, chapter 16; U.S. Pat. No. 5,994,056; EP patent publications 487,218 and 512,334).

(6) Probe-based methods that rely on the difference in stability of hybridization duplexes formed between the probe and the nucleic acid sequences in the fusion area between wild-type genes or transcripts and fusion genes or transcripts that differ in the degree of complementarity (i.e., Conner et al. (1983) Proc. Natl. Acad. Sci. USA 80: 278-282 and U.S. Pat. Nos. 5,468,613; 5,604,099; 5,310,893; 5,451,512; 5,468,613 and 5,604,099).

(7) Methods based on massive parallel sequencing of cDNA libraries. An example method is disclosed under Example 3.

Preferably, levels of expression of the fusion genes of the present invention are detected by real-time PCR, as described further in international patent publication WO 03/048377.

The present invention also encompasses kits for detecting the presence of fusion polypeptides of the invention or of genes and transcripts encoding such fusion polypeptides. Detection kits of the present invention may contain above-described antibodies or antigen-binding fragments that bind to a fusion polypeptide of the present invention. The kits may also contain, depending on the purpose of each immunoassay described above, various detection reagents (enzymes, substrates, etc.) and instruction manuals. Other detection kits of the present invention may contain above-described various oligonucleotides of the present invention (a pair of oligonucleotide primers, oligonucleotide probes, etc.) that hybridize to mRNA encoding a fusion polypeptide of the present invention, cDNA prepared using the mRNA as a template, or genomic DNA. The kits may further contain, depending on the exact method of gene analysis employed), various reagents (enzymes, other oligonucleotides, nucleic acid, reaction buffer, etc.) and instruction manuals.

The discovery of the fusion polypeptides of the invention provides the basis for new diagnostic and therapeutic methods. The fusion polypeptides of the invention are likely to function as drivers of cancer growth. Therefore, the presence of a fusion polypeptide of the invention or the presence of a gene encoding a fusion polypeptide of the invention or its transcript in biopsied or fluid material obtained from a subject is taken to be indicative of an increased susceptibility of the subject to develop a cancerous growth or to the undetected presence in the subject of a cancerous growth. Therefore, the invention also encompasses a method for determining the susceptibility of a subject to cancer or the presence of a previously undetected cancer comprising the steps of (a) obtaining a tissue sample or a fluid sample (blood, serum, urine, saliva, etc.) from a subject to be tested, (b) determining the presence of a fusion polypeptide of the invention or of a polynucleotide sequence encoding such polypeptide in the subject's tissue or fluid sample using the methods and kits described supra, and (c) making a determination of increased susceptibility to cancer or of the likely presence of a cancer based on the positive identification of the fusion polypeptide or of the nucleotide sequence coding for the fusion polypeptide.

The presence of a fusion polypeptide of the invention or of a gene encoding a fusion polypeptide of the invention or its transcript in a tumor sample from a subject is taken to indicate that the growth of the patient's tumor would be inhibited by a therapy that results in an effective inhibition of the FGFR kinase activity of the fusion polypeptide or elimination of the fusion polypeptide. Therefore, the invention also relates to a method of personalized cancer therapy, comprising the steps of (a) taking a biopsy containing cancer cells from a subject suffering from cancer or exhibiting a potentially cancerous tumor, (b) determining, using the methods and kits being described herein, whether the cells in the biopsy contain a gene encoding a fusion polypeptide of the invention or a transcript of such a gene, or express the fusion polypeptide, (c) selecting the subject whose biopsy could be determined to contain the gene for or express the fusion polypeptide for the treatment of step d; and (d) subjecting the selected subject to a therapeutic regimen that comprises administration of a pharmaceutical composition comprising an FGFR kinase inhibitor. Alternatively, the pharmaceutical composition can contain an antibody or antigen-binding fragment that binds to the fusion polypeptide and disrupts its biochemical function or results in its elimination (or immune system-mediated elimination of entire target cells). In yet other related methods (that share steps a-c), step (d) involves administration of a pharmaceutical composition comprising an antisense oligonucleotide that targets mRNA encoding the fusion polypeptide, inhibiting or impairing its translation, or a pharmaceutical composition comprising an siRNA directed towards mRNA encoding the fusion polypeptide, causing cleavage of the mRNA and its subsequent elimination. In specific embodiments of such methods, the antibody or antigen-binding fragment is directed to a sequence of the fusion polypeptide that comprises sequences from both fusion partners, i.e., from FGFR2 and from CCDC147 or VCL, or even more specifically to a sequence that comprises the fusion point. In other specific embodiments of such methods, the RNA or siRNA is directed to a sequence of the fusion gene comprising sequences from both fusion partners, i.e., from FGFR2 and from CCDC147 or VCL, or even more specifically to a sequence that comprises the fusion point.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein is intended merely to better illuminate the invention and does not pose a limitation on the scope of the invention unless otherwise indicated.

The citation and incorporation of patent documents herein is done for convenience only and does not reflect any view of the validity, patentability and/or enforceability of such patent documents. The description herein of any aspect or embodiment of the invention using terms such as reference to an element or elements is intended to provide support for a similar aspect or embodiment of the invention that "consists of"," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent documents cited in this specification are herein incorporated by reference in their entireties as if each individual publication or patent document were specifically and individually indicated to be incorporated by reference.

Although the present invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example 1: Identification of Fusion Genes of the Invention (1) Total RNA Extraction Total RNA was extracted from two macro-dissected 10 μm thick sections from formalin-fixed, paraffin-embedded tissue obtained from biopsies of human cholangiocarcinomas, using the High Pure FFPET RNA Isolation Kit of Roche (product no. 06650775001) according to the manufacturer's instructions. The procedure involved lysis of the deparaffinized tissue using the Roche proprietary RNA tissue lysis buffer supplemented with SDS and incubation with Proteinase K. In the presence of chaotropic salts, the RNA was specifically bound to the glass fibers of the High Pure Filter Tube. Bound RNA was incubated with DNase and purified in a series of rapid wash-and-spin steps and then eluted in water. RNA concentration was determined by absorbance using a NanoDrop spectrophotometer (Thermo Fischer Scientific, 81 Wyman Street, Waltham, Mass. 02454 USA).

(2) DNA Library Preparation

DNA libraries were prepared starting from 500 ng input RNA using an FGFR Fusion Detection kit for Illumina® assembled by ArcherDx (now Enzymatics Inc., Beverly, Mass.). This detection kit is similar to the Archer™ ALK, RET, ROS1 Fusion Detection v1 for Illumine Platform marketed by Enzymatics (product no. AK0001-8) except that ALK-, RET- and ROS1-specific primers are replaced with primers specific for human FGFR1, FGFR2 and FGFR3. The ArcherDx fusion detection kits use anchored multiplex PCR (AMP™) and temperature-stable reagents in order to create libraries for targeted sequencing on the Illumina® MiSeq instrument (Illumina, 5200 Illumina Way, San Diego, Calif. 92122 USA). Libraries were prepared following the manufacturer's instructions.

The concentration of each bar-coded library was determined by PCR using Kapa Biosystems Library Quantification Kit for Illumina no. KK4824 (Kapa Biosystems, Inc., Wilmington, Mass.) according to the manufacturer's instructions. Bar-coded libraries were pooled at equimolar concentrations, loaded on an Illumina® MiSeq desktop sequencer at 10 pM each and sequenced using the Illumina MiSeq v2 (300 cycles) reagent kit (MS-102-2002, Illumina Inc., San Diego, Calif.) and Nextera workflow chemistry. 15% PhiX control v3 of Illumina (FC-110-3001) was added at 10 pM to the library pool to serve as a sequencing control.

(3) Analysis of Sequencing Results

Sequence reads were stripped of the adapter sequences at the 3'-end using cutadapt (Martin, M. (2011) EMBnet.journal 17: 10-12). Read sequences exceeding 20 nucleotides in length were then mapped onto the human genome sequence (Genome Reference Consortium Human Build 37 (GRCh37) using bowtie (Langmead. B. et al. (2009). Genome Biology 10: R25) and tophat (Trapnell, C. et al. (2009) Bioinformatics 25: 1105-11). Reads mapping to more than two locations were discarded and the remainder were annotated to Ensembl genes (Flicek, P. et al. (2014) Nucleic Acids. Res. 42; D749-55, Database issue).

In a second step, not-mapped reads exceeding 75 nucleotides in length were split into three parts of equal length, and left and right extreme parts were mapped separately onto the genome using the same method as above, and then annotated to Ensembl genes.

Fusion sequences were identified as sequences with both reads (from paired-end sequencing) mapped onto two different genes (one being a FGFR gene) or with not-mapped read(s) annotated to two different genes after split (one being a FGFR gene). The consensus sequence of each fusion was generated from multiple alignment of all reads from fusion sequences with Clustal W (Larkin, M. A. et al. (2007) Bioinformatics, 23, 2947-2948). (See SEQ ID NOs: 1 and 2.)

All data processing steps were performed using R 3.0.2 (the R project) and Bioconductor packages (Gentleman, R. C. et al. (2004) Genome Biology 5: R80).

The fusion gene sequences in SEQ ID NOs: 1 and 2 and the derived polypeptide sequences in SEQ ID NOs: 3 and 4 resulted from the above-described effort. Based on the latter polynucleotide sequences, PCR primers were designed that were used in the characterization experiments described under Example 2.

Example 2: Characterization of Fusion Genes of the Invention

RNA samples (700 ng each) (prepared from two tumor biopsies as described in section (1) of Example 1) were denatured at 65° C. for 5 min and then reverse-transcribed with random hexamer primers in a final volume of 20 μL using the Roche Transcriptor First Strand cDNA synthesis kit (product no. 04 896 866 001; Roche Diagnostics AG, Rotkreuz, Switzerland). Reverse transcription was performed with the following cycling conditions: 25° C. for 10 min, 55° C. for 30 min and 85° C. for 5 min.

PCR amplifications were carried out in a 20 μL reaction volume containing 2 μL of ten-fold diluted cDNA, 0.3 μM of each forward and reverse primer (Table 1) and Roche FastStart PCR Master 1× (product no. 04 710 444 001; Roche Diagnostics AG). Cycling conditions were as follows: 1 cycle at 95° C. for 4 min followed by 40 cycles of 95° C. for 30 s, 50° C. for 30 s and 72° C. for 1 min, and 1 cycle at 72° C. for 7 min. PCR products were separated on Lonza FlashGel DNA Cassette 2.2% agarose gels (product no. 57031; Lonza Ltd., Basel, Switzerland).

TABLE 1

Forward and reverse primers used in PCR amplifications. Primers were designed based on the nucleotide sequences of SEQ ID NOs: 1-2 using Primer3 software (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, NJ, pp 365-386)

| Code | SEQ ID NO. | Primer Name | Sequence (5' to 3') |
|---|---|---|---|
| primer 16 | 8 | FGFR2_Forward | CAGAGACCAACGTTCAAGCA |
| primer 17 | 9 | FGFR2_Reverse1 | GGTTGGCTGAGGTCCAAGTA |
| primer 18 | 10 | FGFR2_Reverse2 | TCTTGTGTCAGGGTAACTAGGTGA |
| primer 19 | 11 | VCL_Reverse_1 | AGCTTGATTTCCAGGGTTCC |
| primer 20 | 12 | VCL_Reverse_2 | AAGATACGAGCAGCCGAGAC |
| primer 21 | 14 | CCDC147_Reverse1 | TTCCAGGACTTGCTTTCCAC |
| primer 22 | 15 | CCDC147_Reverse2 | TCCCTGAAAATCTCTTTCCATT |

The results of this analysis can be gleaned from the pre-stained gels shown in FIG. 1. Amplification of cDNA prepared from one of the two tumor biopsies yielded FGFR2-VCL amplification products with the predicted lengths of about 89 and 114 bp, respectively, depending on which of the two reverse primers was used for PCR. No FGFR2-CCDC147 amplification product was detected. Amplification of cDNA prepared from the other tumor biopsy resulted in FGFR2-CCDC147 amplification products with the predicted lengths of about 93 and 132 bp, respectively, depending on which of two reverse primers was used for PCR. No FGFR2-VCL amplification product was detected. Aliquots of amplification products were purified using QIAgen MinElute PCR Purification Kit (28004) according to the manufacturer's instructions and were sequenced using the Sanger method (Sanger et al. (1975) J. Mol. Biol. 94: 441-8). Results are represented in Table 2.

TABLE 2

Nucleotide sequence analysis of PCR amplification products. The 3 most nucleotides of the FGFR2-coding sequence are in bold and underlined.

| Sequencing Primer | Fusion | SEQ ID NO | Sequencing results (5' to 3') |
|---|---|---|---|
| 16 | FGFR2-VCL | 73 | CAACCAATGA**GG**TGGTCTCGGCTGCTCGTATCTTACTTAGGAACCCTGGAAATC AAGCTGA |
| 19 | FGFR2-VCL | 74 | TTGGTTGTGAGAGTGAGAATTCGATCCAAGTCTTCTACCAACTGCTTGAACGTTG GTCTCTGAAGNC |
| 16 | FGFR2-CCDC147 | 75 | CCAATGA**GG**AAAAGGGTGGAAAGCAAGTCCTGGAAGAATCTGCATTTGAAGAA ATGGAAAGAGATTTTCAGGGAAACT |
| 22 | FGFR2-CCDC147 | 76 | GTGAGAGTGAGANTTCGATCCAAGTCTTCTACCAACTGCTTGAACGTTGGTCTCT GAAGT |
| 16 | native FGFR2 | 77 | AATGA**GG**AATACTTGGACCTCAGCCAACCTCTCGAACAGTATTCACCTAGTTACC CTGACACAAGAAGAAN |
| 18 | native FGFR2 | 78 | TTCCTCATTGGTTGTGAGAGTGAGAATTCGATCCAAGTCTTCTACCAACTGCTTG AACGTTGGTCTCTGAACA |

Larger PCR amplification products (of about 400 and 300 bp, respectively) were obtained for the FGFR2-VCL fusion gene transcript using primer pairs 42a/20 and 16/29 (See Tables 1 and 3). These products were sequenced using the Sanger method. The nucleotide sequence determined is shown as SEQ ID NO: 5; the derived polypeptide fragment sequence is SEQ ID NO: 6.

TABLE 3

Additional forward and reverse primers used in PCR amplifications

| Code | SEQ ID NO | Primer Name | Sequence (5' to 3') |
|---|---|---|---|
| primer 42a | 7 | FGFR2 forward | GACTTTGGACTCGCCAGAGA |
| primer 29 | 13 | VCL_Reverse | CCAGCAACCAGCATCTGAG |

Example 3: Diagnostic Method for Detecting FGFR2-VCL and FGFR2-CCDC147 Fusions in Tumor Biopsies (1) Biopsy Samples and RNA Preparation Ten-micron slides are first prepared from formalin-fixed, paraffin-embedded clinical specimens of solid tumors using methods well known in the field. After hematoxylin and eosin staining, a tumoral portion of the tissue is macro-dissected and subjected to total RNA extraction using the High Pure FFPE RNA isolation kit (Roche, catalog number #06 650 775 001), following the manufacturer's instructions. RNA quantity is assessed using a NanoDrop spectrophotometer (Thermo Fischer Scientific, 81 Wyman Street, Waltham, Mass. 02454 USA).

(2) Sequencing

FGFR2-targeted cDNA libraries composed of 100-300 bp sequences are prepared from 500 ng of total RNA using an ArcherDx NGS library preparation kit (Enzymatics, Suite 407J, 100 Cummings Center, Beverly, Mass. 01910, USA), following the manufacturer's instructions. Basically, primers specific to wild type FGFR2 are used to select RNA sequences containing corresponding sequences. The libraries are subjected to paired-end sequencing of 50-150-bp fragments using an Illumine MiSeq instrument (Illumina, 5200 Illumina Way, San Diego, Calif. 92122 USA) as instructed by the manufacturer.

(3) Detection of FGFR2-VCL and FGFR2-CCDC147 Fusion Genes

Reads obtained are aligned with known subsequences of FGFR2 transcripts beginning at the 3' end of the tyrosine kinase domain and ending at the 3' end of the transcripts. Such subsequences are provided in SEQ ID NOs: 64-67 and 72. Sequence alignment software such as BLAST can be used. Alignment length should be equal to or greater than 18. In case an alignment obtained is with the complementary strand, the complementary sequence of the reads should be considered for further analysis instead of the initial reads.

Reads not matching the FGFR2 subsequences should be discarded. In a case in which no read matches any FGFR2 subsequence, fusion detection should be considered to be inconclusive.

For each alignment with an FGFR2 subsequence, the nucleotide position of the read corresponding to the 3' end of the alignment is named N. The read subsequence corresponding to positions N+1 to N+18 is then extracted. In the case that the read does not contain this subsequence, the alignment is discarded. The 18-base subsequence corresponding to positions N+1 to N+18 is then aligned with subsequences of VCL and CCDC147 transcripts beginning at the start codon and ending at the beginning of the sequences encoding the most distant oligomerization domain. Such subsequences are provided in SEQ ID NOs: 68-71.

A tumor specimen is considered to be positive for an FGFR2-VCL or an FGFR2-CCDC147 fusion gene if a read is identified that has no more than 5 mismatches, preferably no more than 3-4 mismatches, more preferably no more than 1-2 mismatches and most preferably no mismatches over the 18-base stretch corresponding to positions N+1 to N+18 with subsequences of VCL or CCDC147 transcripts, respectively. If no such alignment is observed for any read, the tumor specimen is considered to be negative for FGFR2-VCL and FGFR2-CCDC147 fusion genes.

Example 4: In Vitro Tumorigenicity (1) Establishment of Cell Pools Stably Expressing Fusion Polypeptides Stable Rat2 cell pools stably expressing FGFR2-CCDC147 or FGFR2-VCL fusions, respectively, were generated using pExoIN2-based expression plasmids ExoIN2-FGFR2_CCDC147 and pExoIN2-FGFR2_VCL. pExoIN2 was obtained from Trenzyme, (Germany). The latter expression plasmids were introduced into Rat2 cells by electroporation (LONZA Nucleofector II Device/program [X-005], Solution R). 24 h post-transduction, cells were subjected to 1.5 pg/mL puromycin to derive stable expressor cell pools. The FGFR2-CCDC147 sequence used in this example was composed of SEQ ID NO: 16 for the FGFR2 part (nucleic acid 1 to nucleic acid 2574) and SEQ ID NO: 20 for the CCDC147 part (nucleic acid 156 to nucleic acid 3313). The FGFR2-VCL sequence used was composed of SEQ ID NO: 16 for the FGFR2 part (nucleic acid 1 to nucleic acid 2574) and SEQ ID NO: 18 for the VCL part (nucleic acid 2117 to nucleic acid 5482).

Figure 2:
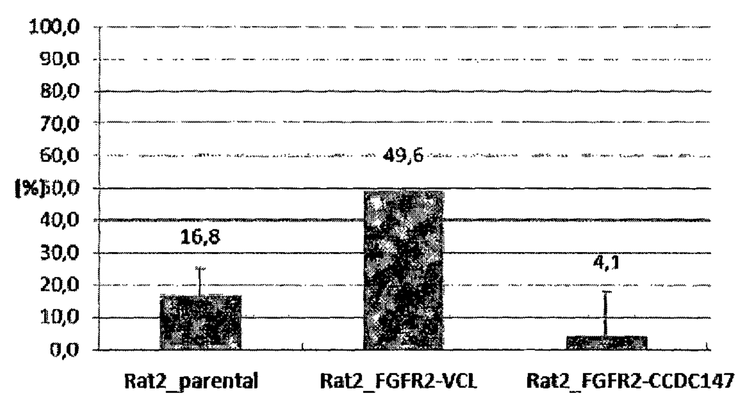
FIG. 2 is a graph representing the plating efficiency (%) results for Rat2 cells and derived cell pools expressing FGFR2-VCL and FGFR2-CCDC147 obtained as per Example 4.

(2) Assessment of Anchorage-Independent Growth Properties of Stable Expressor Cell Pools Single cell suspensions were prepared using ACCUTASE (GE Healthcare Europe GmbH) and diluted such that appropriate cell numbers were seeded in 6well dishes in 0.4% soft-agar top layer without selection antibiotic (seeding densities (cells/well): 10.000, 3.000, 1.000, 300, 100 and 30). Dishes were incubated in a 5% CO2 environment at 37° C. for colony formation. After 21 days of incubation, colonies were fixed using 10% (v/v) acetic acid and 10% (v/v) methanol in H2O and stained with crystal violet (0,01% (w/v) in H2O). Plating efficiency was determined as a ratio between the number of colonies observed after 21 days of incubation in soft agar and the number of seeded cells. The plating efficiency results are shown in FIG. 2.

Figure 3:
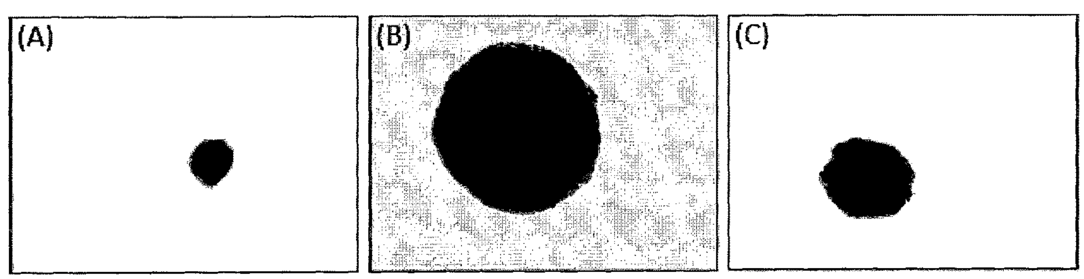
FIG. 3 shows representative images of colonies of Rat2 cells obtained after 21 days of incubation of single cells in soft agar as per Example 4: parental cells (A), FGFR2-VCL expressing cells (B) and FGFR2-CCDC147 expressing cells (C).

For FGFR2-VCL expressing cells, strong colony formation was observed exhibiting high plating efficiency (approximately 50%). Plating efficiency of FGFR2-CCDC147 expressing cells was below that of parental Rat2 cells but colony sizes of parental Rat2 cell line were smaller compared to those of FGFR2-VCL and FGFR2-CCDC147 expressing cell lines (FIG. 3).

Example 5: In Vitro Sensitivity to FGFR Inhibitors (1) Cell Proliferation Assay Using FACS 24 h after seeding (25000 cells/wells), Rat2 cells obtained as per Example 4 (either parental cells or cells expressing FGFR2-VCL or FGFR2-CCDC147 fusion polypeptide) FGFR inhibitors were added, and the cultures were incubated for another 72 h in the presence of the inhibitors. At the end of the incubation period, cells were counted by FACS. IC50 values were calculated in Graphpad Prism 6 using sigmoidal response (variable slope) curve fit. The inhibitors used were selective FGFR inhibitors Compound A, BGJ398 and AZD4547, as well as multi-kinase inhibitor Ponatinib.

Figure 4:
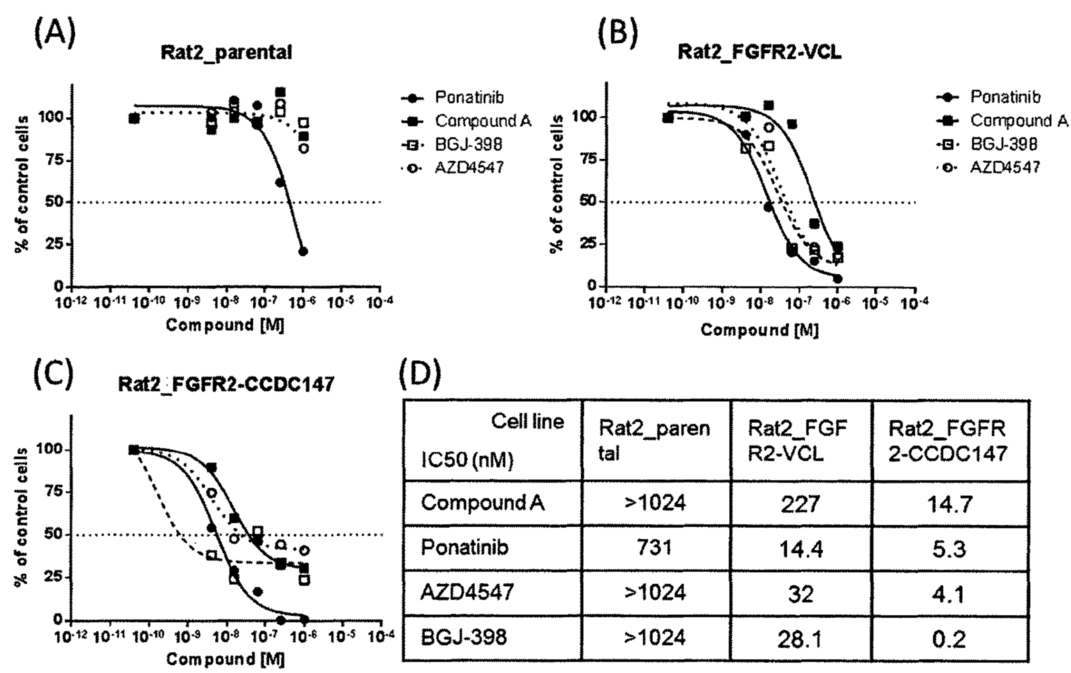
FIG. 4 shows dose response curves obtained with Rat2 cells in the presence of FGFR inhibitors as per Example 5(1): parental cells (A), FGFR2-VCL-expressing cells (B) and FGFR2-CCDC147-expressing cells (C). Growth rates were compared.

FACS analysis revealed that proliferation of the fusion polypeptide-expressing cells was inhibited by all FGFR inhibitors tested (FIG. 4). Multi-kinase inhibitor Ponatinib also inhibited cell proliferation of parental cells due to its large and non-specific spectrum of activity. Relative IC50s of >1024 nM, 227.1 nM and 14.7 nM were obtained for Compound A in Rat2 parental cells, FGFR2-VCL expressing cells and FGFR2-CCDC147 expressing cells, respectively.

Hence, the above results show that cells expressing either fusion of the present invention (FGFR2-VCL or FGFR2-CCDC147, respectively) are sensitive to FGFR selective inhibitors in vitro, whereas parental cells are only sensitive to a multi-kinase inhibitor.

(2) Cell Proliferation Assay Using Cell Titer Glo

Figure 5:
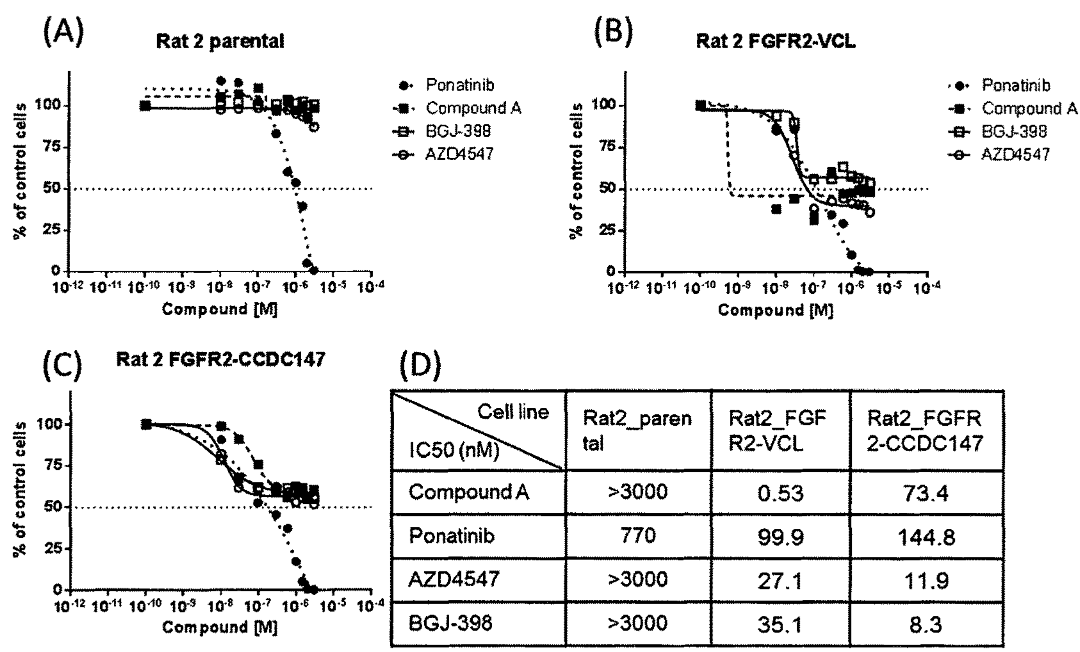
FIG. 5 shows dose response curves obtained with Rat2 cells in the presence of FGFR inhibitors as per Example 5(2): in parental cells (A), FGFR2-VCL-expressing cells (B) and FGFR2-CCDC147-expressing cells (C). Growth rates were compared.

Rat2 cells obtained as per Example 4 (either parental cells or cells expressing FGFR2-VCL or FGFR2-CCDC147 fusion polypeptide) were used in this assay. Cells were seeded in 96 well plates and cultured for 24 h before addition of FGFR inhibitors (the same as in section (1) above). After 72 h of further incubation, cell growth was analyzed by determination of the cellular ATP content (Cell Titer Glo; Promega) using a luminescence plate reader. Relative IC50s of >3000 nM, 0.53 nM and 73.4 nM were obtained for Compound A in Rat2 parental cells, FGFR2-VCL expressing cells and FGFR2-CCDC147 expressing cells, respectively. Dose response curves and a summary of IC50s are shown in FIG. 5.

Thus, FGFR selective inhibitors showed potent inhibition of proliferation of both cell lines harboring FGFR2 fusions (FGFR2-VCL and FGFR2-CCDC147, respectively), whereas parental cells were not affected by FGFR selective inhibitors.

Example 6: In Vivo Tumorigenicity

Figure 6:
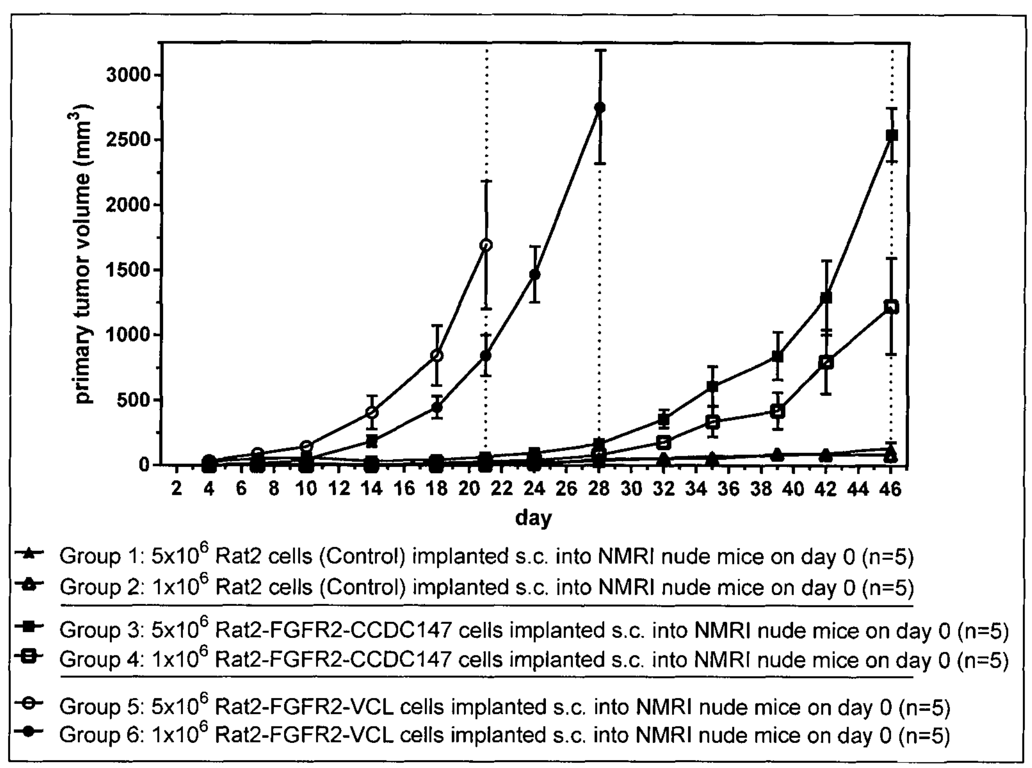
FIG. 6 is a graph showing primary tumor volumes measured as per Example 6 in mice inoculated with Rat2 cells (Groups 1 and 2), Rat2-FGFR2-CCDC147 cells (Groups 3 and 4) and Rat2-FGFR2-VCL cells (Groups 5 and 6), respectively. Data are displayed as means±SEM.

In vivo tumorigenicity of Rat2 cells (either parental cells or cells expressing FGFR2-VCL or FGFR2-CCDC147 fusion polypeptide, obtained as per Example 4) was evaluated in vivo in a subcutaneous tumor model in 5-6 week-old female NMRI nude mice. The study consisted of 6 experimental groups, each containing 5 animals. $5\times10^6$ and $1\times10^6$ Rat2 parental cells (Groups 1 and 2), Rat2-FGFR2-CCDC147 cells (Groups 3 and 4) and Rat2-FGFR2-VCL cells (Groups 5 and 6), respectively, were subcutaneously implanted on day 0. Animal weights of all groups increased continuously during the course of the study. Primary tumor volumes were determined twice weekly by caliper measurement. Tumor volumes were calculated according to the formula $W^2\times L/2$ (L=length and W=the perpendicular width of the tumor, L>W). Results are shown on FIG. 6 (Data are displayed as means±SEM).

In the case of Rat2 parental cells (control), no primary tumor growth could be observed, regardless of the inoculum size. In the case of Rat2-FGFR2-CCDC147 cells, substantial tumor growth could be observed starting around day 28, and the animals that had received higher numbers of implanted cells ($5\times10^6$) exhibited faster tumor growth. In the case of Rat2-FGFR2-VCL cells (Groups 5 and 6), tumor growth was observed starting around 10 days after implantation. Owing to fast tumor growth, Group 5 ($5\times10^6$ cells) had to be terminated for ethical reasons (tumor burden) on day 21, and Group 6 ($1\times10^6$ cells) on day 28. Tumors expressing either FGFR2 fusion construct (FGFR2-VCL or FGFR2-CCDC147) were therefore shown to be tumorigenic in vivo in female NMRI nude mice.

Example 7: In Vivo Sensitivity to FGFR Inhibitors (1) FGFR2-CCDC147 Fusion

On Day 0, $5\times10^6$ FGFR2-CCDC147-expressing Rat2 cells in 100 μl PBS were subcutaneously implanted into the left flank of 5-6 week-old female NMRI nude mice (group size of 6 animals). Compound A was orally administered once daily for 14 consecutive days (30 or 60 mg/kg) in mice with established tumors (D25, mean Tumor Volume=135 $mm^3$). Primary tumor sizes were measured twice weekly by calipering. Animals were terminated on last day of treatment and tumors weighed at necropsy.

Figure 7:
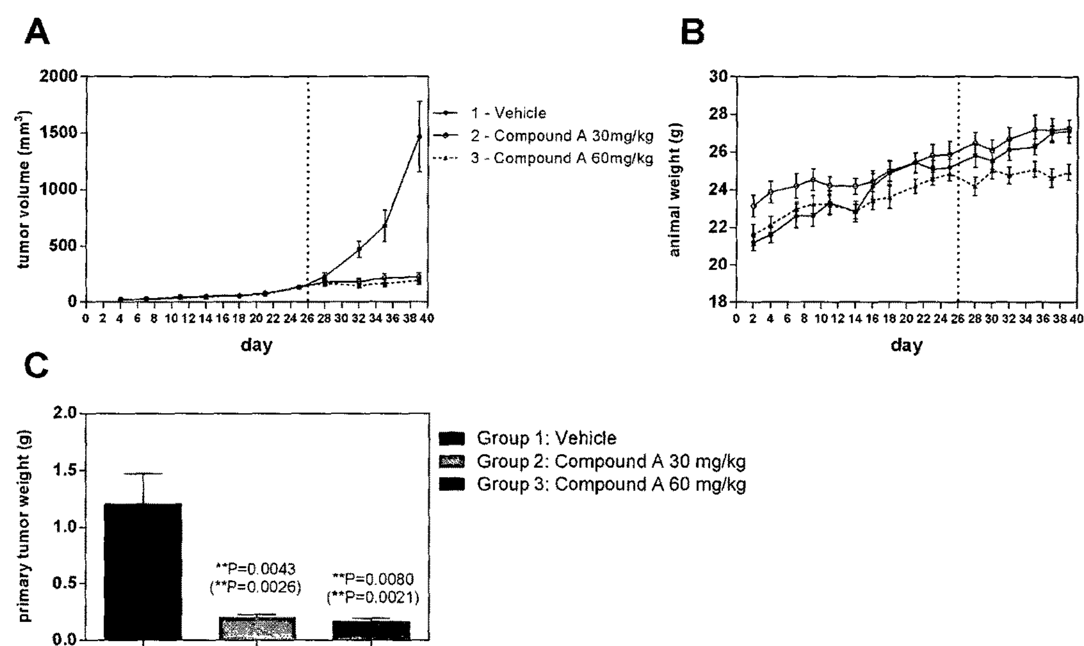
FIG. 7 is a graph showing tumor volumes (A), body weight (B) and tumor weights on the last day of treatment (C) as obtained in the FGFR2-CCDC147 in vivo model of Example 7(1). Data are displayed as means±SEM. P-values were calculated compared to the Vehicle Control using the Mann Whitney test (unpaired t-test in parentheses).

Compound A showed potent antitumor efficacy in vivo in the FGFR2-CCDC147 expressing model (FIG. 7A). Compound A inhibited tumor growth at the two tested doses (30 and 60 mg/kg), whereas no significant effect was observed on body weight (panel B). Data are displayed as means±SEM. P-values were calculated compared to the Vehicle Control using the Mann Whitney test (unpaired t-test in parentheses).

Thus, FGFR selective inhibitor Compound A, administered daily for 14 consecutive days at 30 and 60 mg/kg, showed a highly significant antitumoral efficacy (comparable at both doses) in the subcutaneously implanted Rat2-FGFR2-CCDC147 tumor model in female NMRI nude mice in vivo.

(2) FGFR2-VCL Fusion

On Day 0, $1\times10^6$ FGFR2-VCL expressing Rat2 cells in 100 μl PBS were subcutaneously implanted into the left flank of 5-6 week-old female NMRI nude mice (group size of 6 animals). Compound A was orally administered once daily for 14 consecutive days (30 or 60 mg/kg) in mice with established tumors (D15, mean Tumor Volume=188 $mm^3$).

Primary tumor sizes were measured twice weekly by calipering. Animals were terminated on last day of treatment and tumors weighed at necropsy.

Figure 8:
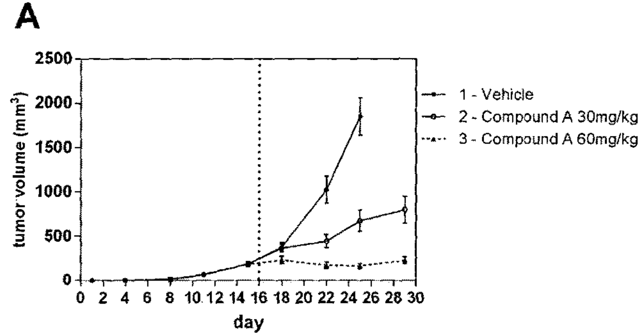
FIG. 8 is a graph showing tumor volumes (A), body weight (B) and tumor weights on the last day of treatment (C) as obtained in the FGFR2-VCL in vivo model of Example 7(2). Data are displayed as means±SEM. P-values were calculated compared to the Vehicle Control and between Groups 2 and 3 using the Mann Whitney test (unpaired t-test in parentheses).
Figure 8:
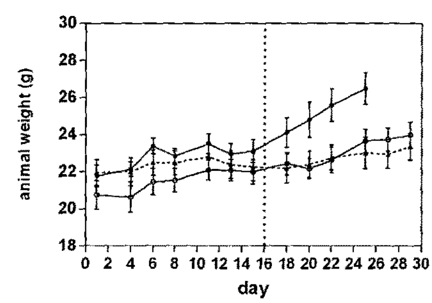
Figure 8:
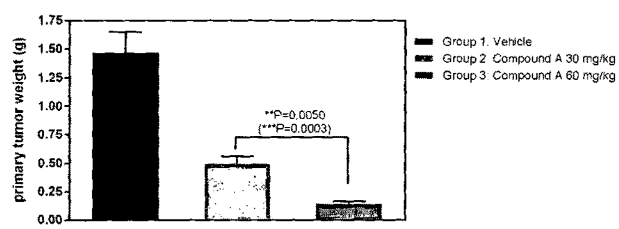

FGFR selective inhibitor Compound A showed potent antitumor efficacy in vivo in FGFR2-VCL-expressing model (FIG. 8A). Compound A inhibited tumor growth without significantly affecting body weight (panel B). Data are displayed as means±SEM. P-values were calculated compared to the Vehicle Control and between Groups 2 and 3 using the Mann Whitney test (unpaired t-test in parentheses).

Thus, FGFR selective inhibitor Compound A, administered orally daily for 14 consecutive days at 30 and 60 mg/kg, showed a highly significant and dose-dependent antitumoral efficacy in the subcutaneously implanted Rat2-FGFR2-VCL tumor model in female NMRI nude mice in vivo. Tumor stasis was observed for the 60 mg/kg-treated group.

Example 8: Functional Analysis of FGFR2-VCL/FGFR2-CCDC147 Autophosphorylation In this example, the following sequences were used: the FGFR2-CCDC147 fusion gene was composed of SEQ ID NO: 16 for the FGFR2 part (nucleic acid 1 to nucleic acid 2574) and SEQ ID NO: 20 for the CCDC147 part (nucleic acid 156 to nucleic acid 3313); and the FGFR2-VCL fusion gene was composed of SEQ ID NO: 16 for the FGFR2 part (nucleic acid 1 to nucleic acid 2574) and SEQ ID NO: 18 for the VCL part (nucleic acid 2117 to nucleic acid 5482).

Figure 9:
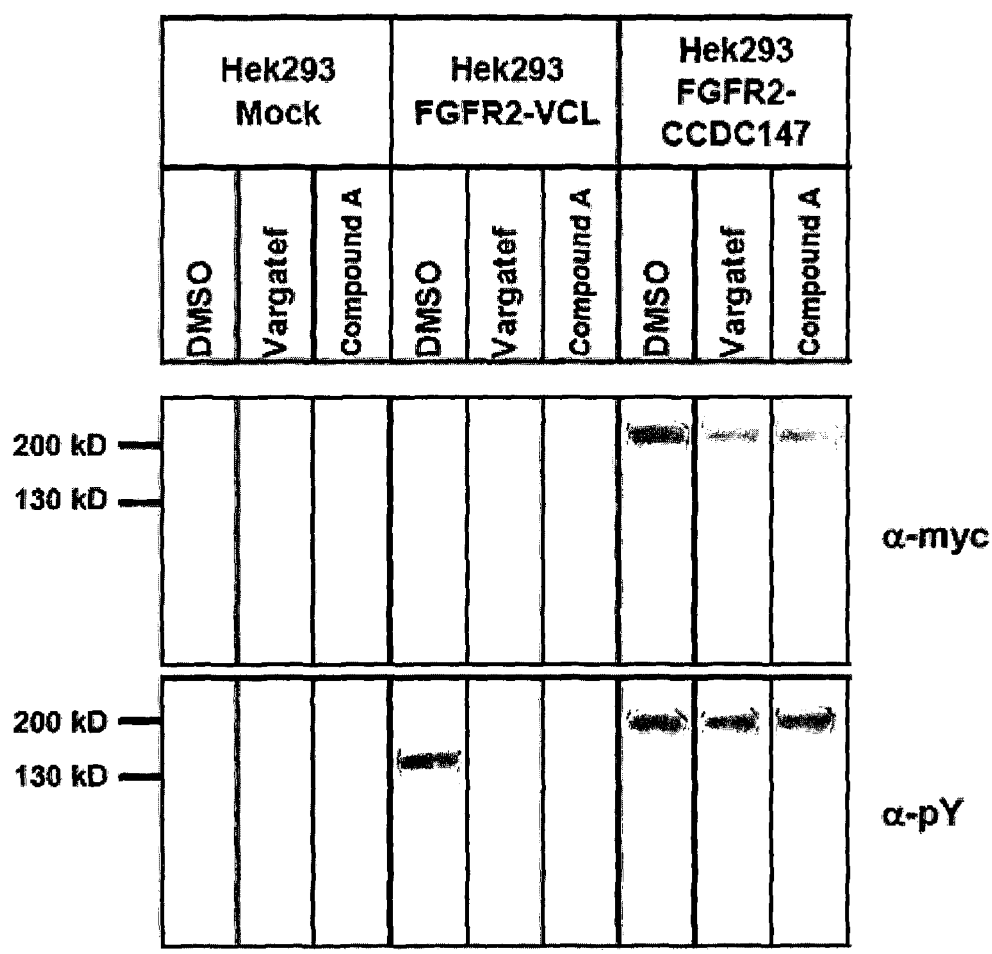
FIG. 9 is a western blot analysis of HEK293T cells transiently mock-transfected or transfected with FGFR2-VCL or FGFR-CCDC147 expression construct and briefly treated with Vargatef, Compound A or vehicle as detailed in Example 8(1). Anti-myc antibody (α-myc) detected the myc-tagged fusion polypeptides, and anti-phosphotyrosine antibody (α-pY) detected phosphorylation of the fusion polypeptides.

(1) Autophosphorylation of FGFR2 Fusion Polypeptides in Transiently Transfected HEK293T Cells Assessed by Western Blot HEK293T cells were transiently transfected with expression plasmids containing either an FGFR2-VCL or an FGFR2-CCDC147 fusion gene, which genes had been supplemented with a C-terminal double myc-tag extension. As a negative control, HEK293T cells were mock-transfected. Cells were treated for 90 min with 0.1% DMSO, 1E-05 M Vargatef or 1E-05 M Compound A. After treatment, expression and autophosphorylation of the fusion polypeptides was analysed by Western blotting. The expression of myc-tagged fusion polypeptide was determined using the anti-myc antibody 9E10 (α-myc), and the phosphorylation analysis was performed with the anti-phosphotyrosine antibody pY99 (α-pY). The results are shown in FIG. 9. Both FGFR2-VCL- and FGFR2-CCDC147-expressing cells show ligand-independent high levels of FGFR phosphorylation. This autophosphorylation appears substantially reduced in FGFR2-VCL-expressing cells and, somewhat more marginally, in FGFR2-CCDC147-expressing cells upon exposure to FGFR selective inhibitor Compound A or less selective inhibitor Vargatef.

Figure 10:
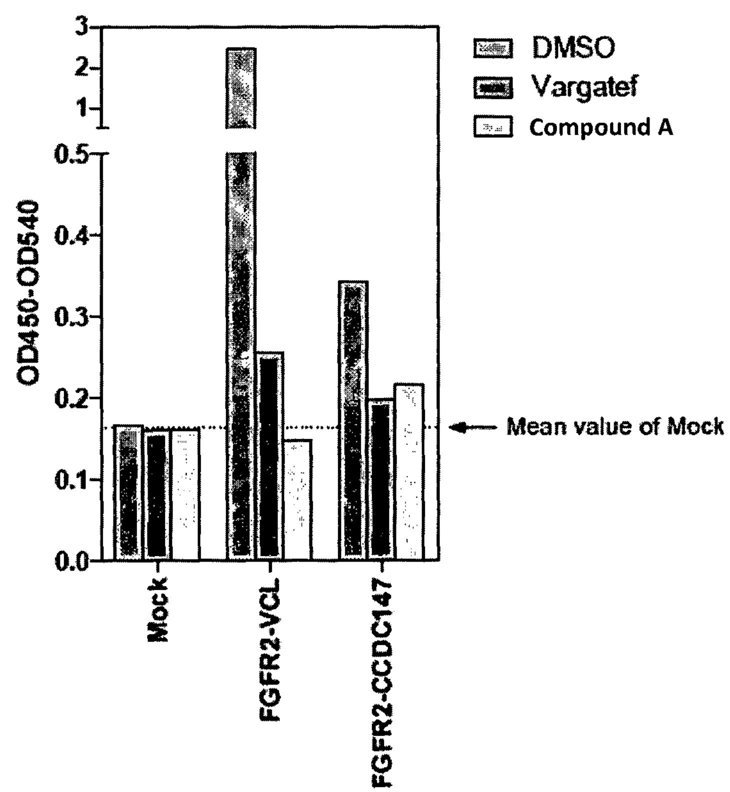
FIG. 10 is a graph reporting results from a similar experiment as in FIG. 9, in which autophosphorylation of fusion polypeptides was quantified by a sandwich phosphotyrosine ELISA as detailed in Example 8(2). Optical density data are shown.

(2) Autophosphorylation of FGFR2 Fusion Polypeptides in Transiently Transfected HEK293T Cells Measured by ELISA HEK293T cells, mock-transfected (control) or transiently transfected with expressible FGFR2-VCL or FGFR2-CCDC147 fusion genes, were treated with 0.1% DMSO, 1E-05 M Vargatef or 1E-05 M Compound A for 90 min. After treatment, autophosphorylation of the FGFR2 fusion polypeptides was analysed using a sandwich phosphotyrosine ELISA. Each condition was done in duplicates. Mean Optical Densities (OD) values of each condition are presented in FIG. 10.

Both FGFR2-VCL- and FGFR2-CCDC147-expressing cells show ligand-independent high levels of FGFR phosphorylation, which levels are decreased by FGFR selective inhibitor Compound A or less selective inhibitor Vargatef.

Example 9: Diagnostic Method for Detecting FGFR2-VCL and FGFR2-CCDC147 Fusions in Tumor Biopsies Using Digital Detection of mRNA Total RNA was extracted from FFPE samples of human cholangiocarcinoma as described in Example 1(1). 500 ng of total RNA were used per sample and analyzed using the nCounter Gene Expression Assay protocol as instructed by the manufacturer (Nanostring). The nCounter assay is based on direct digital detection of mRNA molecules of interest using target-specific, color-coded probes that hybridize directly to a target molecule in solution, so that the expression level of each gene is measured in a relative fashion by counts, without the need for cDNA synthesis and amplification. Each probe is constituted by a Reporter probe part of 50 bases that carries the barcode and a Capture probe part of 50 bases that carries a biotin molecule allowing the target/probe complex to be immobilized to a streptavidin-coated nCounter Cartridge for data collection (Counts) after wash-out of excess probes.

For each fusion gene of the present invention, probes were designed and synthesized by NanoString (Custom CodeSet), then inserted with all consumables and reagents in a ready-to-use nCounter Master Kit for sample processing in the nCounter Analysis System. The target sequences used for the design of the probes, as provided by NanoString, are indicated in Table 4 (detail of Capture probe and Reporter probe not known).

TABLE 4

Target sequences used for the design of the probes in the nCounter assay.

| Gene Identifier | Target Sequence |
|---|---|
| FGFR2-CCDC147 | AGCAGTTGGTAGAAGACTTGGATCGAATTCTCACTCTC ACAACCAATGAGGAAAAGGGTGGAAAGCAAGTCCTGGA AGAATCTGCATTTGAAGAAATGGA (SEQ ID NO: 80) |
| FGFR2-VCL | AGCAGTTGGTAGAAGACTTGGATCGAATTCTCACTCTC ACAACCAATGAGGTGGTCTCGGCTGCTCGTATCTTACT TAGGAACCCTGGAAATCAAGCTGC (SEQ ID NO: 79) |

Count values obtained were background corrected and normalized against the most stable housekeeping genes as previously described (Beaume, et al. (2011) J Microbiol Methods 84: 327-334). The results are presented in Table 5.

TABLE 5

Normalized values obtained for the 2 fusion genes of the present invention in intrahepatic cholangiocarcinoma (iCCA) samples

| | Fusion name | |
|---|---|---|
| Sample Identifier | FGFR2-VCL | FGFR2-CCDC147 |
| iCCA FFPE sample #1 | 129 | 4652 |
| iCCA FFPE sample #2 | 66204 | 1 |

It could thus be determined that the iCCA FFPE sample #1 harbors a FGFR2-CCDC147 gene fusion and that the iCCA FFPE sample #2 harbors a FGFR2-VCL gene fusion. For iCCA FFPE sample #1, it was determined (by PCR amplification using validated primers for both fusions) that the normalized value of 129 regarding FGFR2-VCL resulted from nonspecific hybridization and constituted background noise.

Example 10: Diagnostic Method for Detecting FGFR2-VCL and FGFR2-CCDC147 Fusions in Tumor Biopsies Using DNA (1) Biopsy Samples and DNA Preparation Total DNA are extracted from macro-dissected 10 μm thick sections from formalin-fixed, paraffin-embedded tissue obtained from biopsies of human cholangiocarcinomas. DNA extraction is performed using an FFPE DNA Isolation Kit.

(2) Sequencing

Fusions are detected by capture-enriched DNA sequencing using capture probes for? the VCL and CCDC147 genes, as described by Duncavage et al. (Duncavage et al. Mod Pathol. 2012 June; 25(6):795-804). After fragmentation of the genomic DNA (to fragments of about 250 to 500 bp in length), the fragmented DNA is end repaired, ligated to adapters as per manufacturer's protocol (Illumina, San Diego, Calif., USA). Sequencing libraries are then hybridized with the capture probes per manufacturer's instructions (Agencourt Bioscience, Beverly, Mass., USA). The enriched DNA is then amplified using universal primers targeting the adapters. DNA is then subjected to paired-end sequencing of 50-150-bp fragments using an Illumine MiSeq instrument (Illumina, 5200 Illumina Way, San Diego, Calif. 92122 USA) as instructed by the manufacturer.

(3) Detection of FGFR2-VCL and FGFR2-CCDC147 Fusion Genes

The detection of the FGFR2-VCL and FGFR2-CCDC147 fusion genes is performed as described in example 3(3).

The invention claimed is:

1. A method of cancer therapy, comprising subjecting a subject containing or expressing a gene for a fusion polypeptide or expressing the fusion polypeptide, to a therapeutic regimen that comprises administration of a pharmaceutical composition comprising (1) an inhibitor of fibroblast growth factor receptor (FGFR) kinase activity, (2) an antibody or antigen-binding fragment that binds the fusion polypeptide, (3) an antisense oligonucleotide capable of hybridization in a live cell to a messenger RNA encoding the fusion polypeptide, which hybridization has the effect of preventing or reducing translation of the messenger RNA or (4) an siRNA directed to a messenger RNA encoding the fusion polypeptide, wherein the fusion polypeptide comprises:

a first polypeptide having 95% or more identity with a wild-type FGFR2 polypeptide or with a fragment thereof; and a second polypeptide having 95% or more identity with a wild-type vinculin (VCL) polypeptide or with a fragment thereof.

2. The method of claim 1, wherein the pharmaceutical composition comprises the inhibitor of FGFR kinase activity.

3. The method of claim 1, wherein the first polypeptide comprises a complete tyrosine kinase domain.

4. The method of claim 1, wherein:
the first polypeptide is the wild-type FGFR2 polypeptide or fragment thereof; and
the second polypeptide is the wild-type VCL polypeptide or fragment thereof.

5. The method of claim 2, wherein the inhibitor of FGFR kinase activity is selected from the group consisting of 5-amino-1-(2-methyl-1H-benzimidazol-5-yl)-1H-pyrazol-4-yl]-(1H-indol-2-yl)-methanone, PD173074, pazopanib, AZD4547, ponatinib, dovitinib, BGJ398, E-3810, JNJ-42756493, ARQ 087, LY2874455, BAY1163877, ASP5878, E7090, ODM-203, nintedanib, TAS-120, PRN 1109 and PRN 1371.

6. The method of claim 2, wherein the inhibitor of FGFR kinase activity is 5-amino-1-(2-methyl-1H-benzimidazol-5-yl)-1H-pyrazol-4-yl]-(1H-indol-2-yl)-methanone.

7. A method of cancer therapy, comprising the steps of
(a) taking, from a subject suffering from cancer, a biopsy containing cancer cells, or a fluid sample containing cancer cells or circulating tumor DNA;
(b) determining whether the cancer cells or circulating tumor DNA contains or expresses a gene encoding a fusion polypeptide or expresses the fusion polypeptide;
(c) selecting the subject containing or expressing the gene for the fusion polypeptide or expressing the fusion polypeptide for the treatment of step d; and
(d) subjecting the selected subject to a therapeutic regimen that comprises administration of a pharmaceutical composition comprising (1) an inhibitor of FGFR kinase activity, (2) an antibody or antigen-binding fragment that binds the fusion polypeptide, (3) an antisense oligonucleotide capable of hybridization in a live cell to a messenger RNA encoding the fusion polypeptide, which hybridization has the effect of preventing or reducing translation of the messenger RNA or (4) a siRNA directed to a messenger RNA encoding the fusion polypeptide,
wherein the fusion polypeptide comprises:
a first polypeptide having 95% or more identity with a wild-type FGFR2 polypeptide or with a fragment thereof; and
a second polypeptide having 95% or more identity with a wild-type VCL polypeptide or with a fragment thereof.

8. The method of claim 7, wherein the pharmaceutical composition comprises the inhibitor of FGFR kinase activity.

9. The method of claim 8, wherein the inhibitor of FGFR kinase activity is selected from the group consisting of 5-amino-1-(2-methyl-1H-benzimidazol-5-yl)-1H-pyrazol-4-yl]-(1H-indol-2-yl)-methanone, PD173074, pazopanib, AZD4547, ponatinib, dovitinib, BGJ398, E-3810, JNJ-42756493, ARQ 087, LY2874455, BAY1163877, ASP5878, E7090, ODM-203, nintedanib, TAS-120, PRN 1109 and PRN 1371.

10. The method of claim 8, wherein the inhibitor of FGFR kinase activity is 5-amino-1-(2-methyl-1H-benzimidazol-5-yl)-1H-pyrazol-4-yl]-(1H-indol-2-yl)-methanone.

11. The method of claim 7, wherein the first polypeptide comprises a complete tyrosine kinase domain.

12. The method of claim 7, wherein:
the first polypeptide is the wild-type FGFR2 polypeptide or fragment thereof; and
the second polypeptide is the wild-type VCL polypeptide or fragment thereof.

13. A method of cancer therapy, comprising subjecting a subject containing or expressing a gene for a fusion polypeptide or expressing the fusion polypeptide, to a therapeutic regimen that comprises administration of a pharmaceutical composition comprising (1) an inhibitor of FGFR kinase activity, (2) an antibody or antigen-binding fragment that binds the fusion polypeptide, (3) an antisense oligonucleotide capable of hybridization in a live cell to a messenger RNA encoding the fusion polypeptide, which hybridization has the effect of preventing or reducing translation of the messenger RNA or (4) an siRNA directed to a messenger RNA encoding the fusion polypeptide,
wherein the fusion polypeptide has 95% or more identity with the sequence of SEQ ID NO: 3.

14. The method of claim 13, wherein the pharmaceutical composition comprises the inhibitor of FGFR kinase activity.

15. The method of claim 14, wherein the inhibitor of FGFR kinase activity is selected from the group consisting of 5-amino-1-(2-methyl-1H-benzimidazol-5-yl)-1H-pyrazol-4-yl]-(1H-indol-2-yl)-methanone, PD173074, pazopanib, AZD4547, ponatinib, dovitinib, BGJ398, E-3810, JNJ-42756493, ARQ 087, LY2874455, BAY1163877, ASP5878, E7090, ODM-203, nintedanib, TAS-120, PRN 1109 and PRN 1371.

16. The method of claim 14, wherein the inhibitor of FGFR kinase activity is 5-amino-1-(2-methyl-1H-benzimidazol-5-yl)-1H-pyrazol-4-yl]-(1H-indol-2-yl)-methanone.

17. The method of claim 13, wherein the fusion polypeptide is the polypeptide of SEQ ID NO: 3.

18. A method of cancer therapy, comprising:
(a) taking, from a subject suffering from cancer, a biopsy containing cancer cells, or a fluid sample containing cancer cells or circulating tumor DNA;
(b) determining whether the cancer cells or circulating tumor DNA contains or expresses a gene encoding a fusion polypeptide or expresses the fusion polypeptide;
(c) selecting the subject containing or expressing the gene for the fusion polypeptide or expressing the fusion polypeptide for the treatment of step d; and
(d) subjecting the selected subject to a therapeutic regimen that comprises administration of a pharmaceutical composition comprising (1) an inhibitor of FGFR kinase activity, (2) an antibody or antigen-binding fragment that binds the fusion polypeptide, (3) an antisense oligonucleotide capable of hybridization in a live cell to a messenger RNA encoding the fusion polypeptide, which hybridization has the effect of preventing or reducing translation of the messenger RNA or (4) a siRNA directed to a messenger RNA encoding the fusion polypeptide,
wherein the fusion polypeptide has 95% or more identity with the sequence of SEQ ID NO: 3.

19. The method of claim 18, wherein the pharmaceutical composition comprises the inhibitor of FGFR kinase activity.

20. The method of claim 19, wherein the inhibitor of FGFR kinase activity is selected from the group consisting of 5-amino-1-(2-methyl-1H-benzimidazol-5-yl)-1H-pyrazol-4-yl]-(1H-indol-2-yl)-methanone, PD173074, pazopanib, AZD4547, ponatinib, dovitinib, BGJ398, E-3810, JNJ-42756493, ARQ 087, LY2874455, BAY1163877, ASP5878, E7090, ODM-203, nintedanib, TAS-120, PRN 1109 and PRN 1371.

21. The method of claim 19, wherein the inhibitor of FGFR kinase activity is 5-amino-1-(2-methyl-1H-benzimidazol-5-yl)-1H-pyrazol-4-yl]-(1H-indol-2-yl)-methanone.

22. The method of claim 18, wherein the fusion polypeptide is the polypeptide of SEQ ID NO: 3.

* * * * *

SEQUENCE LISTING

```
<160> NUMBER OF SEQ ID NOS: 80

<210> SEQ ID NO 1
<211> LENGTH: 176
<212> TYPE: DNA
<213> ORGANISM: Homo sapiens
<220> FEATURE:
<221> NAME/KEY: exon
<222> LOCATION: (1)..(72)
<223> OTHER INFORMATION: FGFR2 exon 17
<220> FEATURE:
<221> NAME/KEY: exon
<222> LOCATION: (73)..(176)
<223> OTHER INFORMATION: VCL exon 15

<400> SEQUENCE: 1

ccc tcc cag aga cca acg ttc aag cag ttg gta gaa gac ttg gat cga       48

att ctc act ctc aca acc aat gag gtg gtc tcg gct gct cgt atc tta       96

ctt agg aac cct gga aat caa gct gct tat gaa cat ttt gag acc atg      144

aag aac cag tgg atc gat aat gtt gaa aaa at                           176


<210> SEQ ID NO 2
<211> LENGTH: 200
<212> TYPE: DNA
<213> ORGANISM: Homo sapiens
<220> FEATURE:
<221> NAME/KEY: exon
<222> LOCATION: (1)..(71)
<223> OTHER INFORMATION: FGFR2 exon 17
<220> FEATURE:
```

```
<221> NAME/KEY: exon
<222> LOCATION: (72)..(200)
<223> OTHER INFORMATION: CCDC147 exon 2

<400> SEQUENCE: 2

cct ccc aga gac caa cgt tca agc agt tgg tag aag act tgg atc gaa       48

ttc tca ctc tca caa cca atg ag  g aaa agg gtg gaa agc aag tcc tgg     96

aag aat ctg cat ttg aag aaa tgg aaa gag att ttc agg gag ttc tcc      144

atg aac ttt ctg gag aca aaa gtt tgg aaa aat ttc gga ttg aat atg      192

aga ggc tt                                                           200


<210> SEQ ID NO 3
<211> LENGTH: 58
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: FGFR2 POLYPEPTIDE
<220> FEATURE:
<221> NAME/KEY: DOMAIN
<222> LOCATION: (25)..(58)
<223> OTHER INFORMATION: VCL POLYPEPTIDE

<400> SEQUENCE: 3

Pro Ser Gln Arg Pro Thr Phe Lys Gln Leu Val Glu Asp Leu Asp Arg
1               5                   10                  15

Ile Leu Thr Leu Thr Thr Asn Glu Val Val Ser Ala Ala Arg Ile Leu
            20                  25                  30

Leu Arg Asn Pro Gly Asn Gln Ala Ala Tyr Glu His Phe Glu Thr Met
        35                  40                  45

Lys Asn Gln Trp Ile Asp Asn Val Glu Lys
    50                  55


<210> SEQ ID NO 4
<211> LENGTH: 66
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: FGFR2 POLYPEPTIDE
<220> FEATURE:
<221> NAME/KEY: DOMAIN
<222> LOCATION: (25)..(66)
<223> OTHER INFORMATION: CCDC147 POLYPEPTIDE

<400> SEQUENCE: 4

Ser Gln Arg Pro Thr Phe Lys Gln Leu Val Glu Asp Leu Asp Arg Ile
1               5                   10                  15

Leu Thr Leu Thr Thr Asn Glu Glu Lys Gly Gly Lys Gln Val Leu Glu
            20                  25                  30

Glu Ser Ala Phe Glu Glu Met Glu Arg Asp Phe Gln Gly Val Leu His
        35                  40                  45

Glu Leu Ser Gly Asp Lys Ser Leu Glu Lys Phe Arg Ile Glu Tyr Glu
    50                  55                  60

Arg Leu
65


<210> SEQ ID NO 5
<211> LENGTH: 603
<212> TYPE: DNA
```

```
<213> ORGANISM: Homo sapiens
<220> FEATURE:
<221> NAME/KEY: exon
<222> LOCATION: (1)..(370)
<223> OTHER INFORMATION: FGFR2 exon 17
<220> FEATURE:
<221> NAME/KEY: exon
<222> LOCATION: (371)..(603)
<223> OTHER INFORMATION: VCL exon 15

<400> SEQUENCE: 5

ctt tgg act cgc cag aga tat caa caa tat aga cta tta caa aaa gac       48

cac caa tgg gcg gct tcc agt caa gtg gat ggc tcc aga agc cct gtt       96

tga tag agt ata cac tca tca gag tga tgt ctg gtc ctt cgg ggt gtt      144

aat gtg gga gat ctt cac ttt agg ggg ctc gcc cta ccc agg gat tcc      192

cgt gga gga act ttt taa gct gct gaa gga agg aca cag aat gga taa      240

gcc agc caa ctg cac caa cga act gta cat gat gat gag gga ctg ttg      288

gca tgc agt gcc ctc cca gag acc aac gtt caa gca gtt ggt aga aga      336

ctt gga tcg aat tct cac tct cac aac caa tga g gt  ggt ctc ggc tgc    384

tcg tat ctt act tag gaa ccc tgg aaa tca agc tgc tta tga aca ttt      432

tga gac cat gaa gaa cca gtg gat cga taa tgt tga aaa aat gac agg      480

gct ggt gga cga agc cat tga tac caa atc tct gtt gga tgc ttc aga      528

aga agc aat taa aaa aga cct gga caa gtg caa ggt agc tat ggc caa      576

cat tca gcc tca gat gct ggt tgc tgg                                  603


<210> SEQ ID NO 6
<211> LENGTH: 200
<212> TYPE: PRT
<213> ORGANISM: Homo sapiens
<220> FEATURE:
<221> NAME/KEY: DOMAIN
<222> LOCATION: (1)..(123)
<223> OTHER INFORMATION: FGFR2 POLYPEPTIDE
<220> FEATURE:
<221> NAME/KEY: DOMAIN
<222> LOCATION: (124)..(200)
<223> OTHER INFORMATION: VCL POLYPEPTIDE

<400> SEQUENCE: 6

Phe Gly Leu Ala Arg Asp Ile Asn Asn Ile Asp Tyr Tyr Lys Lys Thr
1               5                   10                  15

Thr Asn Gly Arg Leu Pro Val Lys Trp Met Ala Pro Glu Ala Leu Phe
            20                  25                  30

Asp Arg Val Tyr Thr His Gln Ser Asp Val Trp Ser Phe Gly Val Leu
        35                  40                  45

Met Trp Glu Ile Phe Thr Leu Gly Gly Ser Pro Tyr Pro Gly Ile Pro
    50                  55                  60

Val Glu Glu Leu Phe Lys Leu Leu Lys Glu Gly His Arg Met Asp Lys
65                  70                  75                  80

Pro Ala Asn Cys Thr Asn Glu Leu Tyr Met Met Met Arg Asp Cys Trp
                85                  90                  95

His Ala Val Pro Ser Gln Arg Pro Thr Phe Lys Gln Leu Val Glu Asp
            100                 105                 110

Leu Asp Arg Ile Leu Thr Leu Thr Thr Asn Glu Val Val Ser Ala Ala
        115                 120                 125

Arg Ile Leu Leu Arg Asn Pro Gly Asn Gln Ala Ala Tyr Glu His Phe
```

```
    130                 135                 140

Glu Thr Met Lys Asn Gln Trp Ile Asp Asn Val Glu Lys Met Thr Gly
145                 150                 155                 160

Leu Val Asp Glu Ala Ile Asp Thr Lys Ser Leu Leu Asp Ala Ser Glu
                165                 170                 175

Glu Ala Ile Lys Lys Asp Leu Asp Lys Cys Lys Val Ala Met Ala Asn
            180                 185                 190

Ile Gln Pro Gln Met Leu Val Ala
        195                 200


<210> SEQ ID NO 7
<211> LENGTH: 20
<212> TYPE: DNA
<213> ORGANISM: Homo sapiens

<400> SEQUENCE: 7

gactttggac tcgccagaga                                                   20


<210> SEQ ID NO 8
<211> LENGTH: 20
<212> TYPE: DNA
<213> ORGANISM: Homo sapiens

<400> SEQUENCE: 8

cagagaccaa cgttcaagca                                                   20


<210> SEQ ID NO 9
<211> LENGTH: 20
<212> TYPE: DNA
<213> ORGANISM: Homo sapiens

<400> SEQUENCE: 9

ggttggctga ggtccaagta                                                   20


<210> SEQ ID NO 10
<211> LENGTH: 24
<212> TYPE: DNA
<213> ORGANISM: Homo sapiens

<400> SEQUENCE: 10

tcttgtgtca gggtaactag gtga                                              24


<210> SEQ ID NO 11
<211> LENGTH: 20
<212> TYPE: DNA
<213> ORGANISM: Homo sapiens

<400> SEQUENCE: 11

agcttgattt ccagggttcc                                                   20


<210> SEQ ID NO 12
<211> LENGTH: 20
<212> TYPE: DNA
<213> ORGANISM: Homo sapiens

<400> SEQUENCE: 12

aagatacgag cagccgagac                                                   20


<210> SEQ ID NO 13
<211> LENGTH: 19
<212> TYPE: DNA
<213> ORGANISM: Homo sapiens
```

<400> SEQUENCE: 13
ccagcaacca gcatctgag 19

<210> SEQ ID NO 14
<211> LENGTH: 20
<212> TYPE: DNA
<213> ORGANISM: Homo sapiens

<400> SEQUENCE: 14
ttccaggact tgctttccac 20

<210> SEQ ID NO 15
<211> LENGTH: 22
<212> TYPE: DNA
<213> ORGANISM: Homo sapiens

<400> SEQUENCE: 15
tccctgaaaa tctctttcca tt 22

<210> SEQ ID NO 16
<211> LENGTH: 4255
<212> TYPE: DNA
<213> ORGANISM: Homo sapiens

<400> SEQUENCE: 16
cccaaggacc actcttctgc gtttggagtt gctccccgca accccgggct cgtcgctttc 60
tccatcccga cccacgcggg gcgcggggac aacacaggtc gcggaggagc gttgccattc 120
aagtgactgc agcagcagcg gcagcgcctc ggttcctgag cccaccgcag gctgaaggca 180
ttgcgcgtag tccatgcccg tagaggaagt gtgcagatgg gattaacgtc cacatggaga 240
tatggaagag gaccggggat tggtaccgta accatggtca gctggggtcg tttcatctgc 300
ctggtcgtgg tcaccatggc aaccttgtcc ctggcccggc cctccttcag tttagttgag 360
gataccacat tagagccaga agagccacca accaaatacc aaatctctca accagaagtg 420
tacgtggctg cgccagggga gtcgctagag gtgcgctgcc tgttgaaaga tgccgccgtg 480
atcagttgga ctaaggatgg ggtgcacttg gggcccaaca ataggacagt gcttattggg 540
gagtacttgc agataaaggg cgccacgcct agagactccg gcctctatgc ttgtactgcc 600
agtaggactg tagacagtga aacttggtac ttcatggtga atgtcacaga tgccatctca 660
tccggagatg atgaggatga caccgatggt gcggaagatt ttgtcagtga gaacagtaac 720
aacaagagag caccatactg gaccaacaca gaaaagatgg aaaagcggct ccatgctgtg 780
cctgcggcca acactgtcaa gtttcgctgc ccagccgggg ggaacccaat gccaaccatg 840
cggtggctga aaaacgggaa ggagtttaag caggagcatc gcattggagg ctacaaggta 900
cgaaaccagc actggagcct cattatggaa agtgtggtcc catctgacaa gggaaattat 960
acctgtgtag tggagaatga atacgggtcc atcaatcaca cgtaccacct ggatgttgtg 1020
gagcgatcgc ctcaccggcc catcctccaa gccggactgc cggcaaatgc ctccacagtg 1080
gtcggaggag acgtagagtt tgtctgcaag gtttacagtg atgcccagcc ccacatccag 1140
tggatcaagc acgtggaaaa gaacggcagt aaatacgggc ccgacgggct gccctacctc 1200
aaggttctca aggccgccgg tgttaacacc acggacaaag agattgaggt tctctatatt 1260
cggaatgtaa cttttgagga cgctggggaa tatacgtgct tggcgggtaa ttctattggg 1320
atatcctttc actctgcatg gttgacagtt ctgccagcgc ctggaagaga aaaggagatt 1380

```
acagcttccc cagactacct ggagatagcc atttactgca taggggtctt cttaatcgcc   1440
tgtatggtgg taacagtcat cctgtgccga atgaagaaca cgaccaagaa gccagacttc   1500
agcagccagc cggctgtgca caagctgacc aaacgtatcc ccctgcggag acaggtaaca   1560
gtttcggctg agtccagctc ctccatgaac tccaacaccc cgctggtgag gataacaaca   1620
cgcctctctt caacggcaga cacccccatg ctggcagggg tctccgagta tgaacttcca   1680
gaggacccaa aatgggagtt tccaagagat aagctgacac tgggcaagcc cctgggagaa   1740
ggttgctttg ggcaagtggt catggcggaa gcagtgggaa ttgacaaaga caagcccaag   1800
gaggcggtca ccgtggccgt gaagatgttg aaagatgatg ccacagagaa agacctttct   1860
gatctggtgt cagagatgga gatgatgaag atgattggga aacacaagaa tatcataaat   1920
cttcttggag cctgcacaca ggatgggcct ctctatgtca tagttgagta tgcctctaaa   1980
ggcaacctcc gagaatacct ccgagcccgg aggccacccg ggatggagta ctcctatgac   2040
attaaccgtg ttcctgagga gcagatgacc ttcaaggact tggtgtcatg cacctaccag   2100
ctggccagag gcatggagta cttggcttcc caaaaatgta ttcatcgaga tttagcagcc   2160
agaaatgttt tggtaacaga aaacaatgtg atgaaaatag cagactttgg actcgccaga   2220
gatatcaaca atatagacta ttacaaaaag accaccaatg ggcggcttcc agtcaagtgg   2280
atggctccag aagccctgtt tgatagagta tacactcatc agagtgatgt ctggtccttc   2340
ggggtgttaa tgtgggagat cttcacttta gggggctcgc cctacccagg gattcccgtg   2400
gaggaacttt ttaagctgct gaaggaagga cacagaatgg ataagccagc caactgcacc   2460
aacgaactgt acatgatgat gagggactgt tggcatgcag tgccctccca gagaccaacg   2520
ttcaagcagt tggtagaaga cttggatcga attctcactc tcacaaccaa tgaggaatac   2580
ttggacctca gccaacctct cgaacagtat tcacctagtt accctgacac aagaagttct   2640
tgttcttcag gagatgattc tgtttttct ccagacccca tgccttacga accatgcctt    2700
cctcagtatc cacacataaa cggcagtgtt aaaacatgaa tgactgtgtc tgcctgtccc   2760
caaacaggac agcactggga acctagctac actgagcagg gagaccatgc ctcccagagc   2820
ttgttgtctc cacttgtata tatggatcag aggagtaaat aattggaaaa gtaatcagca   2880
tatgtgtaaa gatttataca gttgaaaact tgtaatcttc cccaggagga gaagaaggtt   2940
tctggagcag tggactgcca caagccacca tgtaacccct ctcacctgcc gtgcgtactg   3000
gctgtggacc agtaggactc aaggtggacg tgcgttctgc cttccttgtt aattttgtaa   3060
taattggaga agatttatgt cagcacacac ttacagagca caaatgcagt atataggtgc   3120
tggatgtatg taaatatatt caaattatgt ataaatatat attatatatt tacaaggagt   3180
tattttttgt attgatttta aatggatgtc ccaatgcacc tagaaaattg gtctctcttt   3240
ttttaatagc tatttgctaa atgctgttct tacacataat ttcttaattt tcaccgagca   3300
gaggtggaaa aatacttttg ctttcaggga aaatggtata acgttaattt attaataaat   3360
tggtaatata caaaacaatt aatcatttat agttttttt gtaatttaag tggcatttct    3420
atgcaggcag cacagcagac tagttaatct attgcttgga cttaactagt tatcagatcc   3480
tttgaaaaga gaatatttac aatatatgac taatttgggg aaaatgaagt tttgatttat   3540
ttgtgtttaa atgctgctgt cagacgattg ttcttagacc tcctaaatgc cccatattaa   3600
aagaactcat tcataggaag gtgtttcatt ttggtgtgca accctgtcat tacgtcaacg   3660
caacgtctaa ctggacttcc caagataaat ggtaccagcg tcctcttaaa agatgcctta   3720
atccattcct tgaggacaga ccttagttga aatgatagca gaatgtgctt ctctctggca   3780
```

```
gctggccttc tgcttctgag ttgcacatta atcagattag cctgtattct cttcagtgaa   3840

ttttgataat ggcttccaga ctctttggcg ttggagacgc ctgttaggat cttcaagtcc   3900

catcatagaa aattgaaaca cagagttgtt ctgctgatag ttttggggat acgtccatct   3960

ttttaaggga ttgctttcat ctaattctgg caggacctca ccaaaagatc cagcctcata   4020

cctacatcag acaaaatatc gccgttgttc cttctgtact aaagtattgt gttttgcttt   4080

ggaaacaccc actcactttg caatagccgt gcaagatgaa tgcagattac actgatctta   4140

tgtgttacaa aattggagaa agtatttaat aaaacctgtt aatttttata ctgacaataa   4200

aaatgtttct acagatatta atgttaacaa gacaaaataa atgtcacgca actta        4255


<210> SEQ ID NO 17
<211> LENGTH: 821
<212> TYPE: PRT
<213> ORGANISM: Homo sapiens

<400> SEQUENCE: 17

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285
```

```
Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
```

```
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820


<210> SEQ ID NO 18
<211> LENGTH: 5482
<212> TYPE: DNA
<213> ORGANISM: Homo sapiens

<400> SEQUENCE: 18

gtagtcgctg cacagtctgt ctcttcgccg gttcccggcc ccgtggatcc tacttctctg     60

tcgcccgcgg ttcgccgccc cgctcgccgc cgcgatgcca gtgtttcata cgcgcacgat    120

cgagagcatc ctggagccgg tggcacagca gatctcccac ctggtgataa tgcacgagga    180

gggcgaggtg gacggcaaag ccattcctga cctcaccgcg cccgtggccg ccgtgcaggc    240

ggccgtcagc aacctcgtcc gggttggaaa agagactgtt caaaccactg aggatcagat    300

tttgaagaga gatatgccac cagcatttat taaggttgag aatgcttgca ccaagcttgt    360

ccaggcagct cagatgcttc agtcagaccc ttactcagtg cctgctcgag attatctaat    420

tgatgggtca aggggcatcc tctctggaac atcagacctg ctccttacct tcgatgaggc    480

tgaggtccgt aaaattatta gagtttgcaa aggaattttg gaatatctta cagtggcaga    540

ggtggtggag actatggaag atttggtcac ttacacaaag aatcttgggc caggaatgac    600

taagatggcc aagatgattg acgagagaca gcaggagctc actcaccagg agcaccgagt    660

gatgttggtg aactcgatga acaccgtgaa agagttgctg ccagttctca tttcagctat    720

gaagattttt gtaacaacta aaaactcaaa aaaccaaggc atagaggaag ctttaaaaaa    780

tcgcaatttt actgtagaaa aaatgagtgc tgaaattaat gagataattc gtgtgttaca    840

actcacctct tgggatgaag atgcctgggc cagcaaggac actgaagcca tgaagagagc    900

attggcctcc atagactcca aactgaacca ggccaaaggt tggctccgtg accctagtgc    960

ctccccaggg gatgctggtg agcaggccat cagacagatc ttagatgaag ctggaaaagt   1020

tggtgaactc tgtgcaggca aagaacgcag ggagattctg ggaacttgca aaatgctagg   1080

gcagatgact gatcaagtgg ctgacctccg tgccagagga caaggatcct caccggtggc   1140

catgcagaaa gctcagcagg tatctcaggg tctggatgtg ctcacagcaa aagtggaaaa   1200

tgcagctcgc aagctggaag ccatgaccaa ctcaaagcag agcattgcaa agaagatcga   1260

tgctgctcag aactggcttg cagatccaaa tggtggaccg gaaggagaag agcagattcg   1320

aggtgctttg gctgaagctc ggaaaatagc agaattatgt gatgatccta aagaaagaga   1380

tgacattcta cgttcccttg ggaaatatc tgctctgact tctaaattag cagatctacg   1440
```

-continued

```
aagacagggg aaaggagatt ctccagaggc tcgagccttg gccaaacagg tggccacggc   1500
cctgcagaac ctgcagacca aaaccaaccg ggctgtggcc aacagcagac cggccaaagc   1560
agctgtacac cttgagggca agattgagca agcacagcgg tggattgata atcccacagt   1620
ggatgaccgt ggagtcggtc aggctgccat ccgggggctt gtggccgaag ggcatcgtct   1680
ggctaatgtt atgatggggc cttatcggca agatcttctc gccaagtgtg accgagtgga   1740
ccagctgaca gcccagctgg ctgacctggc tgccagaggg gaaggggaga gtcctcaggc   1800
acgagcactt gcatctcagc tccaagactc cttaaaggat ctaaaagctc ggatgcagga   1860
ggccatgact caggaagtgt cagatgtttt cagcgatacc acaactccca tcaagctgtt   1920
ggcagtggca gccacggcgc ctcctgatgc gcctaacagg gaagaggtat ttgatgagag   1980
ggcagctaac tttgaaaacc attcaggaaa gcttggtgct acggccgaga aggcggctgc   2040
ggttggtact gctaataaat caacagtgga aggcattcag gcctcagtga agacggcccg   2100
agaactcaca ccccaggtgg tctcggctgc tcgtatctta cttaggaacc ctggaaatca   2160
agctgcttat gaacattttg agaccatgaa gaaccagtgg atcgataatg ttgaaaaaat   2220
gacagggctg gtggacgaag ccattgatac caaatctctg ttggatgctt cagaagaagc   2280
aattaaaaaa gacctggaca agtgcaaggt agctatggcc aacattcagc ctcagatgct   2340
ggttgctggg gcaaccagta ttgctcgtcg ggccaaccgg atcctgctgg tggctaagag   2400
ggaggtggag aattccgagg atcccaagtt ccgtgaggct gtgaaagctg cctctgatga   2460
attgagcaaa accatctccc cgatggtgat ggatgcaaaa gctgtggctg gaaacatttc   2520
cgaccctgga ctgcaaaaga gcttcctgga ctcaggatat cggatcctgg gagctgtggc   2580
caaggtcaga gaagccttcc aacctcagga gcctgacttc ccgccgcctc caccagacct   2640
tgaacaactc cgactaacag atgagcttgc tcctcccaaa ccacctctgc ctgaaggtga   2700
ggtccctcca cctaggcctc caccaccaga ggaaaaggat gaagagttcc ctgagcagaa   2760
ggccggggag gtgattaacc agccaatgat gatggctgcc agacagctcc atgatgaagc   2820
tcgcaaatgg tccagcaagc cgggcatccc agccgctgag gtgggtatag gtgttgtagc   2880
tgaggcagat gcggccgatg ctgctggctt ccctgtcccc cctgacatgg aagacgatta   2940
cgaacctgag ctgctgttaa tgccatccaa tcagccggtc aaccagccca ttctggccgc   3000
ggctcagtcc ttgcatcggg aagctaccaa gtggtctagt aagggcaatg acatcattgc   3060
agcagccaag cgcatggctc tgctgatggc tgagatgtct cggctggtaa gagggggcag   3120
tggtaccaag cgggcactca ttcagtgtgc caaggacatc gccaaggcct cagatgaggt   3180
gactcggttg gccaaggagg ttgccaagca gtgcacagat aaacggatta gaaccaacct   3240
cttacaggta tgtgagcgaa tcccaaccat aagcacccag ctcaaaatcc tgtccacagt   3300
gaaggccacc atgctgggcc ggaccaacat cagtgatgag gagtctgagc aggccacaga   3360
gatgctggtt cacaatgccc agaacctcat gcagtctgtg aaggagactg tgcgggaagc   3420
tgaagctgct tcaatcaaaa ttcgaacaga tgctggattt acactgcgct gggttagaaa   3480
gactccctgg taccagtagg cacctggctg agcctggctg gcacagaaac ctctactaaa   3540
aagaaggaaa atgatctgag tcccaggagc tgcccagagt tgctgggagc tgaaaaatca   3600
catcctggcc tggcacatca gaaaggaatg gggcctcttc caaattagaa gacatttata   3660
ctcttttttc atggacactt tgaaatgtgt ttctgtataa agcctgtatt ctcaaacaca   3720
gttacacttg tgcaccctct atcccaatag gcagactggg tttctagccc atggacttca   3780
cataagctca gaatccaagt gaacactagc cagacactct gctctgccct tgttccctag   3840
```

```
gggacacttc cctctgtttc tctttccttg gctcccattc actcttccag aatcccaaga   3900

cccagggccc aggcaaatca gttactaaga agaaaattgc tgtgcctccc aaaattgttt   3960

tgagctttcc atgttgctgc caaccatacc ttccttccct gggctgtgct acctgggtcc   4020

ttttcagaag tgagctttgc tgctacaggg gaaggtggcc tctgtggagc cccagcatat   4080

gggggcctgg attcatttcc tgcccttcct cagtttaatc cttctagttt cccacaatat   4140

aaaactgtac ttcactgtca ggaagaaatc acagaatcat atgattctgc ttttaccatg   4200

cccctgagca atgtctgtgc tagggaaact tcccgtccca tatcctgcct cagcccgcca   4260

aggtagccat cccatgaaca cactgtgtcc tggtgctctc tgccactgga agggcagagt   4320

agccagggtg tggccctgcc atcttcccag cagggccact cccggcactc catgcttagt   4380

cactgcctgc agaggtctgt gctgaggcct tatcattcat tcttagctct taattgttca   4440

ttttgagctg aaatgctgca ttttaatttt aaccaaaaca tgtctcctat cctggttttt   4500

gtagccttcc tccacatcct ttctaaacaa gattttaaag acatgtaggt gtttgttcat   4560

ctgtaactct aaaagatcct ttttaaattc agtcctaaga aagaggagtg cttgtcccct   4620

aagagtgttt aatggcaagg cagccctgtc tgaaggacac ttcctgccta agggagagtg   4680

gtatttgcag actagaattc tagtgctgct gaagatgaat caatgggaaa tactactcct   4740

gtaattccta cctccctgca accaactaca accaagctct ctgcatctac tcccaagtat   4800

ggggttcaag agagtaatgg gtttcatatt tcttatcacc acagtaagtt cctactaggc   4860

aaaatgagag ggcagtgttt cctttttggt acttattact gctaagtatt tcccagcaca   4920

tgaaacctta tttttttccca aagccagaac cagatgagta aaggagtaag aaccttgcct   4980

gaacatcctt ccttcccacc catcgctgtg tgttagttcc caacatcgaa tgtgtacaac   5040

ttaagttggt cctttacact caggctttca ctatttcctt tataatgagg atgattattt   5100

tcaaggccct cagcatattt gtatagttgc ttgcctgata taaatgcaat attaatgcct   5160

ttaaagtatg aatctatgcc aaagatcact tgttgtttta ctaaagaaag attacttaga   5220

ggaaataaga aaaatcatgt ttgctctccc ggttcttcca gtggtttgag acactggttt   5280

acactttatg ccggatgtgc ttttctccaa tatcagtgct cgagacacag tgaagcaaat   5340

taaaaaaaaa aaaaaaaaaa atccctgaat gatgattaga gacatcaccg ctaaaaaact   5400

acatttataa gctaggattt gttatatgca aatattttct gcctcttctt ttgttctgtt   5460

taaaacaata aaatgcattt gt                                             5482
```

```
<210> SEQ ID NO 19
<211> LENGTH: 1134
<212> TYPE: PRT
<213> ORGANISM: Homo sapiens

<400> SEQUENCE: 19

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80
```

```
Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
        435                 440                 445

Arg Arg Gln Gly Lys Gly Asp Ser Pro Glu Ala Arg Ala Leu Ala Lys
    450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495
```

```
Ile Glu Gln Ala Gln Arg Trp Ile Asp Asn Pro Thr Val Asp Asp Arg
            500                 505                 510

Gly Val Gly Gln Ala Ala Ile Arg Gly Leu Val Ala Glu Gly His Arg
        515                 520                 525

Leu Ala Asn Val Met Met Gly Pro Tyr Arg Gln Asp Leu Leu Ala Lys
    530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765

Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860

Leu Pro Glu Gly Glu Val Pro Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Pro Gly Ile Pro Ala Ala Glu Val Gly Ile Gly Val Val
```

```
        915                 920                 925

Ala Glu Ala Asp Ala Ala Asp Ala Ala Gly Phe Pro Val Pro Pro Asp
    930                 935                 940

Met Glu Asp Asp Tyr Glu Pro Glu Leu Leu Leu Met Pro Ser Asn Gln
945                 950                 955                 960

Pro Val Asn Gln Pro Ile Leu Ala Ala Ala Gln Ser Leu His Arg Glu
                965                 970                 975

Ala Thr Lys Trp Ser Ser Lys Gly Asn Asp Ile Ile Ala Ala Ala Lys
            980                 985                 990

Arg Met Ala Leu Leu Met Ala Glu  Met Ser Arg Leu Val  Arg Gly Gly
        995                 1000                 1005

Ser Gly  Thr Lys Arg Ala Leu  Ile Gln Cys Ala Lys  Asp Ile Ala
    1010                 1015                 1020

Lys Ala  Ser Asp Glu Val Thr  Arg Leu Ala Lys Glu  Val Ala Lys
    1025                 1030                 1035

Gln Cys  Thr Asp Lys Arg Ile  Arg Thr Asn Leu Leu  Gln Val Cys
    1040                 1045                 1050

Glu Arg  Ile Pro Thr Ile Ser  Thr Gln Leu Lys Ile  Leu Ser Thr
    1055                 1060                 1065

Val Lys  Ala Thr Met Leu Gly  Arg Thr Asn Ile Ser  Asp Glu Glu
    1070                 1075                 1080

Ser Glu  Gln Ala Thr Glu Met  Leu Val His Asn Ala  Gln Asn Leu
    1085                 1090                 1095

Met Gln  Ser Val Lys Glu Thr  Val Arg Glu Ala Glu  Ala Ala Ser
    1100                 1105                 1110

Ile Lys  Ile Arg Thr Asp Ala  Gly Phe Thr Leu Arg  Trp Val Arg
    1115                 1120                 1125

Lys Thr  Pro Trp Tyr Gln
    1130
```

<210> SEQ ID NO 20
<211> LENGTH: 3313
<212> TYPE: DNA
<213> ORGANISM: Homo sapiens

<400> SEQUENCE: 20

```
gcgccgagcg cgggtttccg ctcggggcgg gcgatagaga cagcgcgtcg cgcctttagc      60

ttctttccca gactccggcc cagctcctgc gatctccaca gcagcctctg aggccgcccc     120

cagagagcat caggatggct gaggaaaagg gtggaaagca agtcctggaa gaatctgcat     180

ttgaagaaat ggaaagagat tttcagggag ttctccatga actttctgga gacaaaagtt     240

tggaaaaatt tcggattgaa tatgagaggc ttcatgctgt catgaaaaag tcttatgaca     300

atgaaaagcg tctgatggcc aaatgcagag agctaaatgc agagattgta gtgaattctg     360

cgaaggtcgc cactgccctt aagctctctc aggatgatca gaccaccatt gcatccctaa     420

agaaggaaat tgaaaaggcc tggaagatgg tggactcagc ctatgacaaa gagcagaagg     480

ccaaggagac gattcttgct ctgaaagagg aaatagtgaa cctgaccaaa ctagtggagc     540

aggggtctgg actgtcaatg gaccagcata gcaacatccg agatttactg aggttcaaag     600

aagaagtgac aaaggagaga gaccagctct tatcagaagt ggtaaaatta cgagaatccc     660

tagctcagac cactgaacag cagcaggaaa cagagcgatc aaaagaggag gctgaacatg     720

ccatcagtca gttccaacaa gaaatccagc aacgtcagaa cgaagcttcc cgggagttcc     780

ggaagaagga aaaactagag aaagagctca agcagattca ggcagacatg gacagcaggc     840
```

```
agacagaaat aaaagccctg cagcagtatg tgcagaagag caaggaggag cttcagaagc    900
tggagcagca gctgaaggag cagaagatat tgaatgagag agctgcaaag gaactcgagc    960
aatttcagat gagaaatgct aaacttcagc aagagaatga acagcacagt ttggtctgtg   1020
agcagctatc ccaggaaaac caacagaagg cgttggagct caaagccaaa gaggaagaag   1080
tccatcaaat gcgccttgac atcgggaagc tcaacaaaat cagagaacaa attcataaga   1140
aattgcacca caccgaagat caaaaggcag aagtcgaaca gcacaaagaa accctaaaaa   1200
atcagattgt gggattagag agagaggtag aggcttcaaa gaaacaagca gaacttgaca   1260
gaaaggcaat ggacgagctt ctaagagaaa gggacatact aaataagaac atgcttaagg   1320
cggtcaatgc gacccagaag cagacagact tggtaaagct ccatgaacaa gccaagagga   1380
acctggaggg agaaatccag aactacaagg atgaggctca gaagcagaga aagatcatct   1440
ttcatctgga aaaggagcgt gaccggtaca tcaaccaagc cagtgacctt acgcaaaagg   1500
tccttatgaa catggaagac ataaaagttc gtgaaacaca gatttttgac tacaggaaaa   1560
aaatagctga atcagagatt aaattaaaac agcaacagaa cctatatgaa gctgtgagat   1620
cagacagaaa tctgtatagc aaaaatctgg ttgaggctca ggatgaaata acagatatga   1680
agagaaagtt aaagattatg atccatcagg tagatgagct gaaagaagac atctctgcca   1740
aagagtccgc acttgtgaag ctgcacctgg aacagcagcg aatagaaaag gaaaaggaaa   1800
cattgaaggc tgagctgcag aagctgagac aacaagccct ggagacaaaa cactttattg   1860
aaaagcaaga agctgaagag agaaaactcc tgcgaataat tgctgaggct gacggggaga   1920
ggttgagaca gaagaaggaa ttagaccagg tcatcagtga gagagatatc ctggggtctc   1980
agcttgttcg gcgcaatgat gagttagctt tgctctatga gaagatcaag atccaacagt   2040
ctgtgctgaa taaaggggag agccagtaca accagaggtt ggaggacatg agaatcctca   2100
gacttgagat caagaagctt cgccgggaaa aggggattct tgccaggagt atggctaatg   2160
ttgaagaact cagacaggag tttttcaca tgcaaagaga attgttgaag gagaggacac   2220
gctgccgagc cctggaggag gagctggaga atcccctgaa tgtgcacaga tggaggaagc   2280
tcgaggccag cgaccccaat gcatatgagc tgatacagaa aattcacacc ctgcagaagc   2340
gtctcatcag caagactgaa gaggtggttg aaaaagagct gctcctccag gaaaaggaga   2400
aactctacat ggaactaaag cacgtcttgg cccgccagcc tggacctgag gctgcggaac   2460
agctgaagct gtaccgacgc acgctgcatg acaagaagca gcagctgaaa gttttgtctt   2520
cagaattgaa tatgtatgaa gtacagagca aagaatataa atatgaggta gagaaactta   2580
ccaatgagct ccagaattta aagaagaaat acctcgctca gaaacgtaaa gaacaacttc   2640
aaaaaaacaa ggacacagca cccatggata acaccttctt aatggtcaaa ccaaatggtc   2700
ctggttttac tgggggcgga tttcctctca ggtcaaccaa aatgacgttc taacctgaag   2760
ctgctggctg tttccagttg aacaactcat gaaatctgct ctgggacatt ttgggggaat   2820
ctcaaagtcc ttggatcata gaactgagtg ctgagaatcc aggatggaaa gaaatgcaga   2880
actatcatag tcacatacat ataagaggga tggtgttttg tctggttcac gttgatatta   2940
acagatcata attctctctg ttcagttagg ctgacctatt gcatgaagca aatcttttgt   3000
tgctacccca ttgattgaaa tgtactagac cttaatttct ttattacaga cattggtgta   3060
cttgaaggtt ttatatttaa aagtattttt gaaatgcaat gtgtcccctc tcaccttatt   3120
aacaataatc tattttaatt attcctcatt aacaagtcat tgcatgagat gagaaagaag   3180
```

gacaaactct taagaattta aaaagtgttt tgagaatgat ttctatatgg aatttctttt 3240
caggcccgga atgggaaaat ctattccaaa gagacacact aataaatact tcattataaa 3300
aaataaaaaa gaa 3313

<210> SEQ ID NO 21
<211> LENGTH: 872
<212> TYPE: PRT
<213> ORGANISM: Homo sapiens

<400> SEQUENCE: 21

Met Ala Glu Glu Lys Gly Gly Lys Gln Val Leu Glu Glu Ser Ala Phe
1 5 10 15

Glu Glu Met Glu Arg Asp Phe Gln Gly Val Leu His Glu Leu Ser Gly
20 25 30

Asp Lys Ser Leu Glu Lys Phe Arg Ile Glu Tyr Glu Arg Leu His Ala
35 40 45

Val Met Lys Lys Ser Tyr Asp Asn Glu Lys Arg Leu Met Ala Lys Cys
50 55 60

Arg Glu Leu Asn Ala Glu Ile Val Val Asn Ser Ala Lys Val Ala Thr
65 70 75 80

Ala Leu Lys Leu Ser Gln Asp Asp Gln Thr Thr Ile Ala Ser Leu Lys
85 90 95

Lys Glu Ile Glu Lys Ala Trp Lys Met Val Asp Ser Ala Tyr Asp Lys
100 105 110

Glu Gln Lys Ala Lys Glu Thr Ile Leu Ala Leu Lys Glu Glu Ile Val
115 120 125

Asn Leu Thr Lys Leu Val Glu Gln Gly Ser Gly Leu Ser Met Asp Gln
130 135 140

His Ser Asn Ile Arg Asp Leu Leu Arg Phe Lys Glu Glu Val Thr Lys
145 150 155 160

Glu Arg Asp Gln Leu Leu Ser Glu Val Val Lys Leu Arg Glu Ser Leu
165 170 175

Ala Gln Thr Thr Glu Gln Gln Gln Glu Thr Glu Arg Ser Lys Glu Glu
180 185 190

Ala Glu His Ala Ile Ser Gln Phe Gln Gln Glu Ile Gln Gln Arg Gln
195 200 205

Asn Glu Ala Ser Arg Glu Phe Arg Lys Lys Glu Lys Leu Glu Lys Glu
210 215 220

Leu Lys Gln Ile Gln Ala Asp Met Asp Ser Arg Gln Thr Glu Ile Lys
225 230 235 240

Ala Leu Gln Gln Tyr Val Gln Lys Ser Lys Glu Glu Leu Gln Lys Leu
245 250 255

Glu Gln Gln Leu Lys Glu Gln Lys Ile Leu Asn Glu Arg Ala Ala Lys
260 265 270

Glu Leu Glu Gln Phe Gln Met Arg Asn Ala Lys Leu Gln Gln Glu Asn
275 280 285

Glu Gln His Ser Leu Val Cys Glu Gln Leu Ser Gln Glu Asn Gln Gln
290 295 300

Lys Ala Leu Glu Leu Lys Ala Lys Glu Glu Glu Val His Gln Met Arg
305 310 315 320

Leu Asp Ile Gly Lys Leu Asn Lys Ile Arg Glu Gln Ile His Lys Lys
325 330 335

Leu His His Thr Glu Asp Gln Lys Ala Glu Val Glu Gln His Lys Glu
340 345 350

```
Thr Leu Lys Asn Gln Ile Val Gly Leu Glu Arg Glu Val Glu Ala Ser
        355                 360                 365

Lys Lys Gln Ala Glu Leu Asp Arg Lys Ala Met Asp Glu Leu Leu Arg
    370                 375                 380

Glu Arg Asp Ile Leu Asn Lys Asn Met Leu Lys Ala Val Asn Ala Thr
385                 390                 395                 400

Gln Lys Gln Thr Asp Leu Val Lys Leu His Glu Gln Ala Lys Arg Asn
                405                 410                 415

Leu Glu Gly Glu Ile Gln Asn Tyr Lys Asp Glu Ala Gln Lys Gln Arg
            420                 425                 430

Lys Ile Ile Phe His Leu Glu Lys Glu Arg Asp Arg Tyr Ile Asn Gln
        435                 440                 445

Ala Ser Asp Leu Thr Gln Lys Val Leu Met Asn Met Glu Asp Ile Lys
    450                 455                 460

Val Arg Glu Thr Gln Ile Phe Asp Tyr Arg Lys Lys Ile Ala Glu Ser
465                 470                 475                 480

Glu Ile Lys Leu Lys Gln Gln Gln Asn Leu Tyr Glu Ala Val Arg Ser
                485                 490                 495

Asp Arg Asn Leu Tyr Ser Lys Asn Leu Val Glu Ala Gln Asp Glu Ile
            500                 505                 510

Thr Asp Met Lys Arg Lys Leu Lys Ile Met Ile His Gln Val Asp Glu
        515                 520                 525

Leu Lys Glu Asp Ile Ser Ala Lys Glu Ser Ala Leu Val Lys Leu His
    530                 535                 540

Leu Glu Gln Gln Arg Ile Glu Lys Glu Lys Glu Thr Leu Lys Ala Glu
545                 550                 555                 560

Leu Gln Lys Leu Arg Gln Gln Ala Leu Glu Thr Lys His Phe Ile Glu
                565                 570                 575

Lys Gln Glu Ala Glu Glu Arg Lys Leu Leu Arg Ile Ile Ala Glu Ala
            580                 585                 590

Asp Gly Glu Arg Leu Arg Gln Lys Lys Glu Leu Asp Gln Val Ile Ser
        595                 600                 605

Glu Arg Asp Ile Leu Gly Ser Gln Leu Val Arg Arg Asn Asp Glu Leu
    610                 615                 620

Ala Leu Leu Tyr Glu Lys Ile Lys Ile Gln Gln Ser Val Leu Asn Lys
625                 630                 635                 640

Gly Glu Ser Gln Tyr Asn Gln Arg Leu Glu Asp Met Arg Ile Leu Arg
                645                 650                 655

Leu Glu Ile Lys Lys Leu Arg Arg Glu Lys Gly Ile Leu Ala Arg Ser
            660                 665                 670

Met Ala Asn Val Glu Glu Leu Arg Gln Glu Phe Phe His Met Gln Arg
        675                 680                 685

Glu Leu Leu Lys Glu Arg Thr Arg Cys Arg Ala Leu Glu Glu Glu Leu
    690                 695                 700

Glu Asn Pro Leu Asn Val His Arg Trp Arg Lys Leu Glu Ala Ser Asp
705                 710                 715                 720

Pro Asn Ala Tyr Glu Leu Ile Gln Lys Ile His Thr Leu Gln Lys Arg
                725                 730                 735

Leu Ile Ser Lys Thr Glu Glu Val Val Glu Lys Glu Leu Leu Leu Gln
            740                 745                 750

Glu Lys Glu Lys Leu Tyr Met Glu Leu Lys His Val Leu Ala Arg Gln
        755                 760                 765
```

```
Pro Gly Pro Glu Ala Ala Glu Gln Leu Lys Leu Tyr Arg Arg Thr Leu
    770                 775                 780

His Asp Lys Lys Gln Gln Leu Lys Val Leu Ser Ser Glu Leu Asn Met
785                 790                 795                 800

Tyr Glu Val Gln Ser Lys Glu Tyr Lys Tyr Glu Val Glu Lys Leu Thr
                805                 810                 815

Asn Glu Leu Gln Asn Leu Lys Lys Lys Tyr Leu Ala Gln Lys Arg Lys
            820                 825                 830

Glu Gln Leu Gln Lys Asn Lys Asp Thr Ala Pro Met Asp Asn Thr Phe
        835                 840                 845

Leu Met Val Lys Pro Asn Gly Pro Gly Phe Thr Gly Gly Gly Phe Pro
    850                 855                 860

Leu Arg Ser Thr Lys Met Thr Phe
865                 870


<210> SEQ ID NO 22
<211> LENGTH: 2466
<212> TYPE: DNA
<213> ORGANISM: Homo sapiens

<400> SEQUENCE: 22

atggtcagct ggggtcgttt catctgcctg gtcgtggtca ccatggcaac cttgtccctg     60

gcccggccct ccttcagttt agttgaggat accacattag agccagaaga gccaccaacc    120

aaataccaaa tctctcaacc agaagtgtac gtggctgcgc caggggagtc gctagaggtg    180

cgctgcctgt tgaaagatgc cgccgtgatc agttggacta aggatggggt gcacttgggg    240

cccaacaata ggacagtgct tattggggag tacttgcaga taaagggcgc cacgcctaga    300

gactccggcc tctatgcttg tactgccagt aggactgtag acagtgaaac ttggtacttc    360

atggtgaatg tcacagatgc catctcatcc ggagatgatg aggatgacac cgatggtgcg    420

gaagattttg tcagtgagaa cagtaacaac aagagagcac catactggac caacacagaa    480

aagatggaaa agcggctcca tgctgtgcct gcggccaaca ctgtcaagtt tcgctgccca    540

gccgggggga acccaatgcc aaccatgcgg tggctgaaaa acgggaagga gtttaagcag    600

gagcatcgca ttggaggcta caaggtacga aaccagcact ggagcctcat tatggaaagt    660

gtggtcccat ctgacaaggg aaattatacc tgtgtagtgg agaatgaata cgggtccatc    720

aatcacacgt accacctgga tgttgtggag cgatcgcctc accggcccat cctccaagcc    780

ggactgccgg caaatgcctc cacagtggtc ggaggagacg tagagtttgt ctgcaaggtt    840

tacagtgatg cccagcccca catccagtgg atcaagcacg tggaaaagaa cggcagtaaa    900

tacgggcccg acgggctgcc ctacctcaag gttctcaagg ccgccggtgt taacaccacg    960

gacaaagaga ttgaggttct ctatattcgg aatgtaactt ttgaggacgc tggggaatat   1020

acgtgcttgg cgggtaattc tattgggata tcctttcact ctgcatggtt gacagttctg   1080

ccagcgcctg gaagagaaaa ggagattaca gcttccccag actacctgga gatagccatt   1140

tactgcatag gggtcttctt aatcgcctgt atggtggtaa cagtcatcct gtgccgaatg   1200

aagaacacga ccaagaagcc agacttcagc agccagccgg ctgtgcacaa gctgaccaaa   1260

cgtatccccc tgcggagaca ggtaacagtt tcggctgagt ccagctcctc catgaactcc   1320

aacaccccgc tggtgaggat aacaacacgc ctctcttcaa cggcagacac ccccatgctg   1380

gcaggggtct ccgagtatga acttccagag gacccaaaat gggagtttcc aagagataag   1440

ctgacactgg gcaagcccct gggagaaggt tgctttgggc aagtggtcat ggcggaagca   1500
```

```
gtgggaattg acaaagacaa gcccaaggag gcggtcaccg tggccgtgaa gatgttgaaa   1560

gatgatgcca cagagaaaga cctttctgat ctggtgtcag agatggagat gatgaagatg   1620

attgggaaac acaagaatat cataaatctt cttggagcct gcacacagga tgggcctctc   1680

tatgtcatag ttgagtatgc ctctaaaggc aacctccgag aatacctccg agcccggagg   1740

ccacccggga tggagtactc ctatgacatt aaccgtgttc ctgaggagca gatgaccttc   1800

aaggacttgg tgtcatgcac ctaccagctg gccagaggca tggagtactt ggcttcccaa   1860

aaatgtattc atcgagattt agcagccaga aatgttttgg taacagaaaa caatgtgatg   1920

aaaatagcag actttggact cgccagagat atcaacaata tagactatta caaaaagacc   1980

accaatgggc ggcttccagt caagtggatg gctccagaag ccctgtttga tagagtatac   2040

actcatcaga gtgatgtctg gtccttcggg gtgttaatgt gggagatctt cactttaggg   2100

ggctcgccct acccagggat tcccgtggag gaacttttta agctgctgaa ggaaggacac   2160

agaatggata agccagccaa ctgcaccaac gaactgtaca tgatgatgag ggactgttgg   2220

catgcagtgc cctcccagag accaacgttc aagcagttgg tagaagactt ggatcgaatt   2280

ctcactctca caaccaatga ggaatacttg gacctcagcc aacctctcga acagtattca   2340

cctagttacc ctgacacaag aagttcttgt tcttcaggag atgattctgt tttttctcca   2400

gaccccatgc cttacgaacc atgccttcct cagtatccac acataaacgg cagtgttaaa   2460

acatga                                                              2466


<210> SEQ ID NO 23
<211> LENGTH: 821
<212> TYPE: PRT
<213> ORGANISM: Homo sapiens

<400> SEQUENCE: 23

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
```

-continued

```
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620
```

```
Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820
```

<210> SEQ ID NO 24
<211> LENGTH: 2124
<212> TYPE: DNA
<213> ORGANISM: Homo sapiens
<220> FEATURE:
<221> NAME/KEY: variation
<222> LOCATION: (2107)..(2107)
<223> OTHER INFORMATION: Y = C or T (dbSNP entry rs1047057)

<400> SEQUENCE: 24

```
atggtcagct ggggtcgttt catctgcctg gtcgtggtca ccatggcaac cttgtccctg     60

gcccggccct ccttcagttt agttgaggat accacattag agccagaaga tgccatctca    120

tccggagatg atgaggatga caccgatggt gcggaagatt ttgtcagtga gaacagtaac    180

aacaagagag caccatactg gaccaacaca gaaaagatgg aaaagcggct ccatgctgtg    240

cctgcggcca acactgtcaa gtttcgctgc ccagccgggg ggaacccaat gccaaccatg    300

cggtggctga aaaacgggaa ggagtttaag caggagcatc gcattggagg ctacaaggta    360

cgaaaccagc actggagcct cattatggaa agtgtggtcc catctgacaa gggaaattat    420

acctgtgtag tggagaatga atacgggtcc atcaatcaca cgtaccacct ggatgttgtg    480

gagcgatcgc ctcaccggcc catcctccaa gccggactgc cggcaaatgc ctccacagtg    540

gtcggaggag acgtagagtt tgtctgcaag gtttacagtg atgcccagcc ccacatccag    600

tggatcaagc acgtggaaaa gaacggcagt aaatacgggc ccgacgggct gccctacctc    660

aaggttctca aggccgccgg tgttaacacc acggacaaag agattgaggt tctctatatt    720

cggaatgtaa cttttgagga cgctggggaa tatacgtgct tggcgggtaa ttctattggg    780

atatcctttc actctgcatg gttgacagtt ctgccagcgc ctggaagaga aaaggagatt    840
```

```
acagcttccc cagactacct ggagatagcc atttactgca taggggtctt cttaatcgcc    900

tgtatggtgg taacagtcat cctgtgccga atgaagaaca cgaccaagaa gccagacttc    960

agcagccagc cggctgtgca caagctgacc aaacgtatcc ccctgcggag acaggtaaca   1020

gtttcggctg agtccagctc ctccatgaac tccaacaccc cgctggtgag gataacaaca   1080

cgcctctctt caacggcaga cacccccatg ctggcagggg tctccgagta tgaacttcca   1140

gaggacccaa aatgggagtt tccaagagat aagctgacac tgggcaagcc cctgggagaa   1200

ggttgctttg ggcaagtggt catggcggaa gcagtgggaa ttgacaaaga caagcccaag   1260

gaggcggtca ccgtggccgt gaagatgttg aaagatgatg ccacagagaa agacctttct   1320

gatctggtgt cagagatgga gatgatgaag atgattggga aacacaagaa tatcataaat   1380

cttcttggag cctgcacaca ggatgggcct ctctatgtca tagttgagta tgcctctaaa   1440

ggcaacctcc gagaatacct ccgagcccgg aggccacccg ggatggagta ctcctatgac   1500

attaaccgtg ttcctgagga gcagatgacc ttcaaggact tggtgtcatg cacctaccag   1560

ctggccagag gcatggagta cttggcttcc caaaaatgta ttcatcgaga tttagcagcc   1620

agaaatgttt tggtaacaga aaacaatgtg atgaaaatag cagactttgg actcgccaga   1680

gatatcaaca atatagacta ttacaaaaag accaccaatg ggcggcttcc agtcaagtgg   1740

atggctccag aagccctgtt tgatagagta tacactcatc agagtgatgt ctggtccttc   1800

ggggtgttaa tgtgggagat cttcacttta gggggctcgc cctacccagg gattcccgtg   1860

gaggaacttt ttaagctgct gaaggaagga cacagaatgg ataagccagc caactgcacc   1920

aacgaactgt acatgatgat gagggactgt tggcatgcag tgccctccca gagaccaacg   1980

ttcaagcagt tggtagaaga cttggatcga attctcactc tcacaaccaa tgaggaggag   2040

aagaaggttt ctggagcagt ggactgccac aagccaccat gtaacccctc tcacctgccg   2100

tgcgtaytgg ctgtggacca gtag                                          2124
```

<210> SEQ ID NO 25
<211> LENGTH: 707
<212> TYPE: PRT
<213> ORGANISM: Homo sapiens

<400> SEQUENCE: 25

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140
```

```
Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205

Gly Ser Lys Tyr Gly Pro Asp Gly Leu Pro Tyr Leu Lys Val Leu Lys
    210                 215                 220

Ala Ala Gly Val Asn Thr Thr Asp Lys Glu Ile Glu Val Leu Tyr Ile
225                 230                 235                 240

Arg Asn Val Thr Phe Glu Asp Ala Gly Glu Tyr Thr Cys Leu Ala Gly
                245                 250                 255

Asn Ser Ile Gly Ile Ser Phe His Ser Ala Trp Leu Thr Val Leu Pro
            260                 265                 270

Ala Pro Gly Arg Glu Lys Glu Ile Thr Ala Ser Pro Asp Tyr Leu Glu
        275                 280                 285

Ile Ala Ile Tyr Cys Ile Gly Val Phe Leu Ile Ala Cys Met Val Val
    290                 295                 300

Thr Val Ile Leu Cys Arg Met Lys Asn Thr Thr Lys Lys Pro Asp Phe
305                 310                 315                 320

Ser Ser Gln Pro Ala Val His Lys Leu Thr Lys Arg Ile Pro Leu Arg
                325                 330                 335

Arg Gln Val Thr Val Ser Ala Glu Ser Ser Ser Ser Met Asn Ser Asn
            340                 345                 350

Thr Pro Leu Val Arg Ile Thr Thr Arg Leu Ser Ser Thr Ala Asp Thr
        355                 360                 365

Pro Met Leu Ala Gly Val Ser Glu Tyr Glu Leu Pro Glu Asp Pro Lys
    370                 375                 380

Trp Glu Phe Pro Arg Asp Lys Leu Thr Leu Gly Lys Pro Leu Gly Glu
385                 390                 395                 400

Gly Cys Phe Gly Gln Val Val Met Ala Glu Ala Val Gly Ile Asp Lys
                405                 410                 415

Asp Lys Pro Lys Glu Ala Val Thr Val Ala Val Lys Met Leu Lys Asp
            420                 425                 430

Asp Ala Thr Glu Lys Asp Leu Ser Asp Leu Val Ser Glu Met Glu Met
        435                 440                 445

Met Lys Met Ile Gly Lys His Lys Asn Ile Ile Asn Leu Leu Gly Ala
    450                 455                 460

Cys Thr Gln Asp Gly Pro Leu Tyr Val Ile Val Glu Tyr Ala Ser Lys
465                 470                 475                 480

Gly Asn Leu Arg Glu Tyr Leu Arg Ala Arg Arg Pro Pro Gly Met Glu
                485                 490                 495

Tyr Ser Tyr Asp Ile Asn Arg Val Pro Glu Glu Gln Met Thr Phe Lys
            500                 505                 510

Asp Leu Val Ser Cys Thr Tyr Gln Leu Ala Arg Gly Met Glu Tyr Leu
        515                 520                 525

Ala Ser Gln Lys Cys Ile His Arg Asp Leu Ala Ala Arg Asn Val Leu
    530                 535                 540

Val Thr Glu Asn Asn Val Met Lys Ile Ala Asp Phe Gly Leu Ala Arg
545                 550                 555                 560
```

```
Asp Ile Asn Asn Ile Asp Tyr Tyr Lys Lys Thr Thr Asn Gly Arg Leu
                565                 570                 575

Pro Val Lys Trp Met Ala Pro Glu Ala Leu Phe Asp Arg Val Tyr Thr
            580                 585                 590

His Gln Ser Asp Val Trp Ser Phe Gly Val Leu Met Trp Glu Ile Phe
        595                 600                 605

Thr Leu Gly Gly Ser Pro Tyr Pro Gly Ile Pro Val Glu Glu Leu Phe
    610                 615                 620

Lys Leu Leu Lys Glu Gly His Arg Met Asp Lys Pro Ala Asn Cys Thr
625                 630                 635                 640

Asn Glu Leu Tyr Met Met Met Arg Asp Cys Trp His Ala Val Pro Ser
                645                 650                 655

Gln Arg Pro Thr Phe Lys Gln Leu Val Glu Asp Leu Asp Arg Ile Leu
            660                 665                 670

Thr Leu Thr Thr Asn Glu Glu Glu Lys Lys Val Ser Gly Ala Val Asp
        675                 680                 685

Cys His Lys Pro Pro Cys Asn Pro Ser His Leu Pro Cys Val Leu Ala
    690                 695                 700

Val Asp Gln
705


<210> SEQ ID NO 26
<211> LENGTH: 2358
<212> TYPE: DNA
<213> ORGANISM: Homo sapiens

<400> SEQUENCE: 26

atggtcagct ggggtcgttt catctgcctg gtcgtggtca ccatggcaac cttgtccctg      60

gcccggccct ccttcagttt agttgaggat accacattag agccagaaga gccaccaacc     120

aaataccaaa tctctcaacc agaagtgtac gtggctgcgc caggggagtc gctagaggtg     180

cgctgcctgt tgaaagatgc cgccgtgatc agttggacta aggatggggt gcacttgggg     240

cccaacaata ggacagtgct tattggggag tacttgcaga taaagggcgc cacgcctaga     300

gactccggcc tctatgcttg tactgccagt aggactgtag acagtgaaac ttggtacttc     360

atggtgaatg tcacagatgc catctcatcc ggagatgatg aggatgacac cgatggtgcg     420

gaagattttg tcagtgagaa cagtaacaac aagagagcac catactggac caacacagaa     480

aagatggaaa agcggctcca tgctgtgcct gcggccaaca ctgtcaagtt tcgctgccca     540

gccgggggga acccaatgcc aaccatgcgg tggctgaaaa acgggaagga gtttaagcag     600

gagcatcgca ttggaggcta caaggtacga aaccagcact ggagcctcat tatggaaagt     660

gtggtcccat ctgacaaggg aaattatacc tgtgtagtgg agaatgaata cgggtccatc     720

aatcacacgt accacctgga tgttgtggag cgatcgcctc accggcccat cctccaagcc     780

ggactgccgg caaatgcctc cacagtggtc ggaggagacg tagagtttgt ctgcaaggtt     840

tacagtgatg cccagcccca catccagtgg atcaagcacg tggaaaagaa cggcagtaaa     900

tacgggcccg acgggctgcc ctacctcaag gttctcaagg ccgccggtgt taacaccacg     960

gacaaagaga ttgaggttct ctatattcgg aatgtaactt ttgaggacgc tggggaatat    1020

acgtgcttgg cgggtaattc tattgggata tcctttcact ctgcatggtt gacagttctg    1080

ccagcgcctg gaagagaaaa ggagattaca gcttccccag actacctgga gatagccatt    1140

tactgcatag gggtcttctt aatcgcctgt atggtggtaa cagtcatcct gtgccgaatg    1200

aagaacacga ccaagaagcc agacttcagc agccagccgg ctgtgcacaa gctgaccaaa    1260
```

```
cgtatccccc tgcggagaca ggtttcggct gagtccagct cctccatgaa ctccaacacc   1320

ccgctggtga ggataacaac acgcctctct tcaacggcag acaccccccat gctggcaggg   1380

gtctccgagt atgaacttcc agaggaccca aaatgggagt ttccaagaga taagctgaca   1440

ctgggcaagc ccctgggaga aggttgcttt gggcaagtgg tcatggcgga agcagtggga   1500

attgacaaag acaagcccaa ggaggcggtc accgtggccg tgaagatgtt gaaagatgat   1560

gccacagaga aagacctttc tgatctggtg tcagagatgg agatgatgaa gatgattggg   1620

aaacacaaga atatcataaa tcttcttgga gcctgcacac aggatgggcc tctctatgtc   1680

atagttgagt atgcctctaa aggcaacctc cgagaatacc tccgagcccg gaggccaccc   1740

gggatggagt actcctatga cattaaccgt gttcctgagg agcagatgac cttcaaggac   1800

ttggtgtcat gcacctacca gctggccaga ggcatggagt acttggcttc ccaaaaatgt   1860

attcatcgag atttagcagc cagaaatgtt ttggtaacag aaaacaatgt gatgaaaata   1920

gcagactttg gactcgccag agatatcaac aatatagact attacaaaaa gaccaccaat   1980

gggcggcttc cagtcaagtg gatggctcca gaagccctgt ttgatagagt atacactcat   2040

cagagtgatg tctggtcctt cggggtgtta atgtgggaga tcttcacttt agggggctcg   2100

ccctacccag ggattcccgt ggaggaactt tttaagctgc tgaaggaagg acacagaatg   2160

gataagccag ccaactgcac caacgaactg tacatgatga tgagggactg ttggcatgca   2220

gtgccctccc agagaccaac gttcaagcag ttggtagaag acttggatcg aattctcact   2280

ctcacaacca atgaggaata cttggacctc agtcagcctc tcgaaccgta ttcaccttgt   2340

tatcctgacc caagatga                                                2358
```

```
<210> SEQ ID NO 27
<211> LENGTH: 785
<212> TYPE: PRT
<213> ORGANISM: Homo sapiens

<400> SEQUENCE: 27

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175
```

```
Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Ser Ala Glu Ser
            420                 425                 430

Ser Ser Ser Met Asn Ser Asn Thr Pro Leu Val Arg Ile Thr Thr Arg
        435                 440                 445

Leu Ser Ser Thr Ala Asp Thr Pro Met Leu Ala Gly Val Ser Glu Tyr
    450                 455                 460

Glu Leu Pro Glu Asp Pro Lys Trp Glu Phe Pro Arg Asp Lys Leu Thr
465                 470                 475                 480

Leu Gly Lys Pro Leu Gly Glu Gly Cys Phe Gly Gln Val Val Met Ala
                485                 490                 495

Glu Ala Val Gly Ile Asp Lys Asp Lys Pro Lys Glu Ala Val Thr Val
            500                 505                 510

Ala Val Lys Met Leu Lys Asp Asp Ala Thr Glu Lys Asp Leu Ser Asp
        515                 520                 525

Leu Val Ser Glu Met Glu Met Met Lys Met Ile Gly Lys His Lys Asn
    530                 535                 540

Ile Ile Asn Leu Leu Gly Ala Cys Thr Gln Asp Gly Pro Leu Tyr Val
545                 550                 555                 560

Ile Val Glu Tyr Ala Ser Lys Gly Asn Leu Arg Glu Tyr Leu Arg Ala
                565                 570                 575

Arg Arg Pro Pro Gly Met Glu Tyr Ser Tyr Asp Ile Asn Arg Val Pro
            580                 585                 590
```

```
Glu Glu Gln Met Thr Phe Lys Asp Leu Val Ser Cys Thr Tyr Gln Leu
        595                 600                 605

Ala Arg Gly Met Glu Tyr Leu Ala Ser Gln Lys Cys Ile His Arg Asp
    610                 615                 620

Leu Ala Ala Arg Asn Val Leu Val Thr Glu Asn Asn Val Met Lys Ile
625                 630                 635                 640

Ala Asp Phe Gly Leu Ala Arg Asp Ile Asn Asn Ile Asp Tyr Tyr Lys
                645                 650                 655

Lys Thr Thr Asn Gly Arg Leu Pro Val Lys Trp Met Ala Pro Glu Ala
            660                 665                 670

Leu Phe Asp Arg Val Tyr Thr His Gln Ser Asp Val Trp Ser Phe Gly
        675                 680                 685

Val Leu Met Trp Glu Ile Phe Thr Leu Gly Gly Ser Pro Tyr Pro Gly
    690                 695                 700

Ile Pro Val Glu Glu Leu Phe Lys Leu Leu Lys Glu Gly His Arg Met
705                 710                 715                 720

Asp Lys Pro Ala Asn Cys Thr Asn Glu Leu Tyr Met Met Met Arg Asp
                725                 730                 735

Cys Trp His Ala Val Pro Ser Gln Arg Pro Thr Phe Lys Gln Leu Val
            740                 745                 750

Glu Asp Leu Asp Arg Ile Leu Thr Leu Thr Thr Asn Glu Glu Tyr Leu
        755                 760                 765

Asp Leu Ser Gln Pro Leu Glu Pro Tyr Ser Pro Cys Tyr Pro Asp Pro
    770                 775                 780

Arg
785
```

<210> SEQ ID NO 28
<211> LENGTH: 2043
<212> TYPE: DNA
<213> ORGANISM: Homo sapiens

<400> SEQUENCE: 28

```
atggtcagct ggggtcgttt catctgcctg gtcgtggtca ccatggcaac cttgtccctg      60

gcccggccct ccttcagttt agttgaggat accacattag agccagaaga tgccatctca     120

tccggagatg atgaggatga caccgatggt gcggaagatt ttgtcagtga gaacagtaac     180

aacaagagag caccatactg gaccaacaca gaaaagatgg aaaagcggct ccatgctgtg     240

cctgcggcca acactgtcaa gtttcgctgc ccagccgggg ggaacccaat gccaaccatg     300

cggtggctga aaaacgggaa ggagtttaag caggagcatc gcattggagg ctacaaggta     360

cgaaaccagc actggagcct cattatggaa agtgtggtcc catctgacaa gggaaattat     420

acctgtgtag tggagaatga atacgggtcc atcaatcaca cgtaccacct ggatgttgtg     480

gagcgatcgc ctcaccggcc catcctccaa gccggactgc cggcaaatgc ctccacagtg     540

gtcggaggag acgtagagtt tgtctgcaag gtttacagtg atgcccagcc ccacatccag     600

tggatcaagc acgtggaaaa gaacggcagt aaatacgggc ccgacgggct gccctacctc     660

aaggttctca agcactcggg gataaatagt tccaatgcag aagtgctggc tctgttcaat     720

gtgaccgagg cggatgctgg ggaatatata tgtaaggtct ccaattatat agggcaggcc     780

aaccagtctg cctggctcac tgtcctgcca aaacagcaag cgcctggaag agaaaaggag     840

attacagctt ccccagacta cctggagata gccatttact gcataggggt cttcttaatc     900

gcctgtatgg tggtaacagt catcctgtgc cgaatgaaga acacgaccaa gaagccagac     960
```

```
ttcagcagcc agccggctgt gcacaagctg accaaacgta tccccctgcg gagacaggta   1020
acagtttcgg ctgagtccag ctcctccatg aactccaaca ccccgctggt gaggataaca   1080
acacgcctct cttcaacggc agacaccccc atgctggcag gggtctccga gtatgaactt   1140
ccagaggacc caaaatggga gtttccaaga gataagctga cactgggcaa gcccctggga   1200
gaaggttgct ttgggcaagt ggtcatggcg gaagcagtgg gaattgacaa agacaagccc   1260
aaggaggcgg tcaccgtggc cgtgaagatg ttgaaagatg atgccacaga gaaagacctt   1320
tctgatctgg tgtcagagat ggagatgatg aagatgattg ggaaacacaa gaatatcata   1380
aatcttcttg gagcctgcac acaggatggg cctctctatg tcatagttga gtatgcctct   1440
aaaggcaacc tccgagaata cctccgagcc cggaggccac ccgggatgga gtactcctat   1500
gacattaacc gtgttcctga ggagcagatg accttcaagg acttggtgtc atgcacctac   1560
cagctggcca gaggcatgga gtacttggct tcccaaaaat gtattcatcg agatttagca   1620
gccagaaatg ttttggtaac agaaaacaat gtgatgaaaa tagcagactt tggactcgcc   1680
agagatatca acaatataga ctattacaaa aagaccacca atgggcggct tccagtcaag   1740
tggatggctc cagaagccct gtttgataga gtatacactc atcagagtga tgtctggtcc   1800
ttcggggtgt taatgtggga gatcttcact ttagggggct cgccctaccc agggattccc   1860
gtggaggaac tttttaagct gctgaaggaa ggacacagaa tggataagcc agccaactgc   1920
accaacgaac tgtacatgat gatgagggac tgttggcatg cagtgccctc ccagagacca   1980
acgttcaagc agttggtaga agacttggat cgaattctca ctctcacaac caatgagatc   2040
tga                                                                2043
```

<210> SEQ ID NO 29
<211> LENGTH: 680
<212> TYPE: PRT
<213> ORGANISM: Homo sapiens

<400> SEQUENCE: 29

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175
```

```
Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205

Gly Ser Lys Tyr Gly Pro Asp Gly Leu Pro Tyr Leu Lys Val Leu Lys
    210                 215                 220

His Ser Gly Ile Asn Ser Ser Asn Ala Glu Val Leu Ala Leu Phe Asn
225                 230                 235                 240

Val Thr Glu Ala Asp Ala Gly Glu Tyr Ile Cys Lys Val Ser Asn Tyr
                245                 250                 255

Ile Gly Gln Ala Asn Gln Ser Ala Trp Leu Thr Val Leu Pro Lys Gln
            260                 265                 270

Gln Ala Pro Gly Arg Glu Lys Glu Ile Thr Ala Ser Pro Asp Tyr Leu
        275                 280                 285

Glu Ile Ala Ile Tyr Cys Ile Gly Val Phe Leu Ile Ala Cys Met Val
    290                 295                 300

Val Thr Val Ile Leu Cys Arg Met Lys Asn Thr Thr Lys Lys Pro Asp
305                 310                 315                 320

Phe Ser Ser Gln Pro Ala Val His Lys Leu Thr Lys Arg Ile Pro Leu
                325                 330                 335

Arg Arg Gln Val Thr Val Ser Ala Glu Ser Ser Ser Ser Met Asn Ser
            340                 345                 350

Asn Thr Pro Leu Val Arg Ile Thr Thr Arg Leu Ser Ser Thr Ala Asp
        355                 360                 365

Thr Pro Met Leu Ala Gly Val Ser Glu Tyr Glu Leu Pro Glu Asp Pro
    370                 375                 380

Lys Trp Glu Phe Pro Arg Asp Lys Leu Thr Leu Gly Lys Pro Leu Gly
385                 390                 395                 400

Glu Gly Cys Phe Gly Gln Val Val Met Ala Glu Ala Val Gly Ile Asp
                405                 410                 415

Lys Asp Lys Pro Lys Glu Ala Val Thr Val Ala Val Lys Met Leu Lys
            420                 425                 430

Asp Asp Ala Thr Glu Lys Asp Leu Ser Asp Leu Val Ser Glu Met Glu
        435                 440                 445

Met Met Lys Met Ile Gly Lys His Lys Asn Ile Ile Asn Leu Leu Gly
    450                 455                 460

Ala Cys Thr Gln Asp Gly Pro Leu Tyr Val Ile Val Glu Tyr Ala Ser
465                 470                 475                 480

Lys Gly Asn Leu Arg Glu Tyr Leu Arg Ala Arg Arg Pro Pro Gly Met
                485                 490                 495

Glu Tyr Ser Tyr Asp Ile Asn Arg Val Pro Glu Glu Gln Met Thr Phe
            500                 505                 510

Lys Asp Leu Val Ser Cys Thr Tyr Gln Leu Ala Arg Gly Met Glu Tyr
        515                 520                 525

Leu Ala Ser Gln Lys Cys Ile His Arg Asp Leu Ala Ala Arg Asn Val
    530                 535                 540

Leu Val Thr Glu Asn Asn Val Met Lys Ile Ala Asp Phe Gly Leu Ala
545                 550                 555                 560

Arg Asp Ile Asn Asn Ile Asp Tyr Tyr Lys Lys Thr Thr Asn Gly Arg
                565                 570                 575

Leu Pro Val Lys Trp Met Ala Pro Glu Ala Leu Phe Asp Arg Val Tyr
            580                 585                 590

Thr His Gln Ser Asp Val Trp Ser Phe Gly Val Leu Met Trp Glu Ile
```

```
        595                 600                 605

Phe Thr Leu Gly Gly Ser Pro Tyr Pro Gly Ile Pro Val Glu Glu Leu
    610                 615                 620

Phe Lys Leu Leu Lys Glu Gly His Arg Met Asp Lys Pro Ala Asn Cys
625                 630                 635                 640

Thr Asn Glu Leu Tyr Met Met Met Arg Asp Cys Trp His Ala Val Pro
                645                 650                 655

Ser Gln Arg Pro Thr Phe Lys Gln Leu Val Glu Asp Leu Asp Arg Ile
            660                 665                 670

Leu Thr Leu Thr Thr Asn Glu Ile
        675                 680


<210> SEQ ID NO 30
<211> LENGTH: 3405
<212> TYPE: DNA
<213> ORGANISM: Homo sapiens
<220> FEATURE:
<221> NAME/KEY: variation
<222> LOCATION: (2388)..(2388)
<223> OTHER INFORMATION: R = G or A (dbSNP entry rs767809)
<220> FEATURE:
<221> NAME/KEY: variation
<222> LOCATION: (2814)..(2814)
<223> OTHER INFORMATION: S = C or G (dbSNP entry rs2131956)

<400> SEQUENCE: 30

atgccagtgt ttcatacgcg cacgatcgag agcatcctgg agccggtggc acagcagatc     60

tcccacctgg tgataatgca cgaggagggc gaggtggacg gcaaagccat tcctgacctc    120

accgcgcccg tggccgccgt gcaggcggcc gtcagcaacc tcgtccgggt tggaaaagag    180

actgttcaaa ccactgagga tcagattttg aagagagata tgccaccagc atttattaag    240

gttgagaatg cttgcaccaa gcttgtccag gcagctcaga tgcttcagtc agacccttac    300

tcagtgcctg ctcgagatta tctaattgat gggtcaaggg gcatcctctc tggaacatca    360

gacctgctcc ttaccttcga tgaggctgag gtccgtaaaa ttattagagt ttgcaaagga    420

attttggaat atcttacagt ggcagaggtg gtggagacta tggaagattt ggtcacttac    480

acaaagaatc ttgggccagg aatgactaag atggccaaga tgattgacga gagacagcag    540

gagctcactc accaggagca ccgagtgatg ttggtgaact cgatgaacac cgtgaaagag    600

ttgctgccag ttctcatttc agctatgaag atttttgtaa caactaaaaa ctcaaaaaac    660

caaggcatag aggaagcttt aaaaaatcgc aattttactg tagaaaaaat gagtgctgaa    720

attaatgaga taattcgtgt gttacaactc acctcttggg atgaagatgc ctgggccagc    780

aaggacactg aagccatgaa gagagcattg gcctccatag actccaaact gaaccaggcc    840

aaaggttggc tccgtgaccc tagtgcctcc ccaggggatg ctggtgagca ggccatcaga    900

cagatcttag atgaagctgg aaaagttggt gaactctgtg caggcaaaga acgcagggag    960

attctgggaa cttgcaaaat gctagggcag atgactgatc aagtggctga cctccgtgcc   1020

agaggacaag gatcctcacc ggtggccatg cagaaagctc agcaggtatc tcagggtctg   1080

gatgtgctca cagcaaaagt ggaaaatgca gctcgcaagc tggaagccat gaccaactca   1140

aagcagagca ttgcaaagaa gatcgatgct gctcagaact ggcttgcaga tccaaatggt   1200

ggaccggaag gagaagagca gattcgaggt gctttggctg aagctcggaa aatagcagaa   1260

ttatgtgatg atcctaaaga aagagatgac attctacgtt ccccttgggga aatatctgct   1320

ctgacttcta aattagcaga tctacgaaga caggggaaag gagattctcc agaggctcga   1380
```

```
gccttggcca aacaggtggc cacggccctg cagaacctgc agaccaaaac caaccgggct   1440

gtggccaaca gcagaccggc caaagcagct gtacaccttg agggcaagat tgagcaagca   1500

cagcggtgga ttgataatcc cacagtggat gaccgtggag tcggtcaggc tgccatccgg   1560

gggcttgtgg ccgaagggca tcgtctggct aatgttatga tggggcctta tcggcaagat   1620

cttctcgcca agtgtgaccg agtggaccag ctgacagccc agctggctga cctggctgcc   1680

agaggggaag ggagagtcc tcaggcacga gcacttgcat ctcagctcca agactcctta   1740

aaggatctaa aagctcggat gcaggaggcc atgactcagg aagtgtcaga tgttttcagc   1800

gataccacaa ctcccatcaa gctgttggca gtggcagcca cggcgcctcc tgatgcgcct   1860

aacagggaag aggtatttga tgagagggca gctaactttg aaaaccattc aggaaagctt   1920

ggtgctacgg ccgagaaggc ggctgcggtt ggtactgcta ataaatcaac agtggaaggc   1980

attcaggcct cagtgaagac ggcccgagaa ctcacacccc aggtggtctc ggctgctcgt   2040

atcttactta ggaaccctgg aaatcaagct gcttatgaac attttgagac catgaagaac   2100

cagtggatcg ataatgttga aaaaatgaca gggctggtgg acgaagccat tgataccaaa   2160

tctctgttgg atgcttcaga agaagcaatt aaaaaagacc tggacaagtg caaggtagct   2220

atggccaaca ttcagcctca gatgctggtt gctggggcaa ccagtattgc tcgtcgggcc   2280

aaccggatcc tgctggtggc taagagggag gtggagaatt ccgaggatcc caagttccgt   2340

gaggctgtga aagctgcctc tgatgaattg agcaaaacca tctccccrat ggtgatggat   2400

gcaaaagctg tggctggaaa catttccgac cctggactgc aaaagagctt cctggactca   2460

ggatatcgga tcctgggagc tgtggccaag gtcagagaag ccttccaacc tcaggagcct   2520

gacttcccgc cgcctccacc agaccttgaa caactccgac taacagatga gcttgctcct   2580

cccaaaccac ctctgcctga aggtgaggtc cctccaccta ggcctccacc accagaggaa   2640

aaggatgaag agttccctga gcagaaggcc ggggaggtga ttaaccagcc aatgatgatg   2700

gctgccagac agctccatga tgaagctcgc aaatggtcca gcaagccggg catcccagcc   2760

gctgaggtgg gtataggtgt tgtagctgag gcagatgcgg ccgatgctgc tggsttccct   2820

gtccccccctg acatggaaga cgattacgaa cctgagctgc tgttaatgcc atccaatcag   2880

ccggtcaacc agcccattct ggccgcggct cagtccttgc atcgggaagc taccaagtgg   2940

tctagtaagg gcaatgacat cattgcagca gccaagcgca tggctctgct gatggctgag   3000

atgtctcggc tggtaagagg gggcagtggt accaagcggg cactcattca gtgtgccaag   3060

gacatcgcca aggcctcaga tgaggtgact cggttggcca aggaggttgc caagcagtgc   3120

acagataaac ggattagaac caacctctta caggtatgtg agcgaatccc aaccataagc   3180

acccagctca aaatcctgtc cacagtgaag gccaccatgc tgggccggac caacatcagt   3240

gatgaggagt ctgagcaggc cacagagatg ctggttcaca atgcccagaa cctcatgcag   3300

tctgtgaagg agactgtgcg ggaagctgaa gctgcttcaa tcaaaattcg aacagatgct   3360

ggatttacac tgcgctgggt tagaaagact ccctggtacc agtag                   3405
```

<210> SEQ ID NO 31
<211> LENGTH: 1134
<212> TYPE: PRT
<213> ORGANISM: Homo sapiens

<400> SEQUENCE: 31

```
Met Pro Val Phe His Thr Arg Thr Ile Glu Ser Ile Leu Glu Pro Val
1               5                   10                  15
```

-continued

```
Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
```

```
        435                 440                 445

Arg Arg Gln Gly Lys Gly Asp Ser Pro Glu Ala Arg Ala Leu Ala Lys
    450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495

Ile Glu Gln Ala Gln Arg Trp Ile Asp Asn Pro Thr Val Asp Asp Arg
            500                 505                 510

Gly Val Gly Gln Ala Ala Ile Arg Gly Leu Val Ala Glu Gly His Arg
        515                 520                 525

Leu Ala Asn Val Met Met Gly Pro Tyr Arg Gln Asp Leu Leu Ala Lys
    530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765

Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860
```

```
Leu Pro Glu Gly Glu Val Pro Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Pro Gly Ile Pro Ala Ala Glu Val Gly Ile Gly Val Val
        915                 920                 925

Ala Glu Ala Asp Ala Ala Asp Ala Ala Gly Phe Pro Val Pro Pro Asp
    930                 935                 940

Met Glu Asp Asp Tyr Glu Pro Glu Leu Leu Leu Met Pro Ser Asn Gln
945                 950                 955                 960

Pro Val Asn Gln Pro Ile Leu Ala Ala Ala Gln Ser Leu His Arg Glu
                965                 970                 975

Ala Thr Lys Trp Ser Ser Lys Gly Asn Asp Ile Ile Ala Ala Ala Lys
            980                 985                 990

Arg Met Ala Leu Leu Met Ala Glu  Met Ser Arg Leu Val  Arg Gly Gly
        995                 1000                 1005

Ser Gly  Thr Lys Arg Ala Leu  Ile Gln Cys Ala Lys  Asp Ile Ala
    1010                 1015                 1020

Lys Ala  Ser Asp Glu Val Thr  Arg Leu Ala Lys Glu  Val Ala Lys
    1025                 1030                 1035

Gln Cys  Thr Asp Lys Arg Ile  Arg Thr Asn Leu Leu  Gln Val Cys
    1040                 1045                 1050

Glu Arg  Ile Pro Thr Ile Ser  Thr Gln Leu Lys Ile  Leu Ser Thr
    1055                 1060                 1065

Val Lys  Ala Thr Met Leu Gly  Arg Thr Asn Ile Ser  Asp Glu Glu
    1070                 1075                 1080

Ser Glu  Gln Ala Thr Glu Met  Leu Val His Asn Ala  Gln Asn Leu
    1085                 1090                 1095

Met Gln  Ser Val Lys Glu Thr  Val Arg Glu Ala Glu  Ala Ala Ser
    1100                 1105                 1110

Ile Lys  Ile Arg Thr Asp Ala  Gly Phe Thr Leu Arg  Trp Val Arg
    1115                 1120                 1125

Lys Thr  Pro Trp Tyr Gln
    1130


<210> SEQ ID NO 32
<211> LENGTH: 3201
<212> TYPE: DNA
<213> ORGANISM: Homo sapiens
<220> FEATURE:
<221> NAME/KEY: variation
<222> LOCATION: (2388)..(2388)
<223> OTHER INFORMATION: R = A or G (dbSNP entry rs767809)

<400> SEQUENCE: 32

atgccagtgt ttcatacgcg cacgatcgag agcatcctgg agccggtggc acagcagatc     60

tcccacctgg tgataatgca cgaggagggc gaggtggacg gcaaagccat tcctgacctc    120

accgcgcccg tggccgccgt gcaggcggcc gtcagcaacc tcgtccgggt tggaaaagag    180

actgttcaaa ccactgagga tcagattttg aagagagata tgccaccagc atttattaag    240

gttgagaatg cttgcaccaa gcttgtccag gcagctcaga tgcttcagtc agacccttac    300

tcagtgcctg ctcgagatta tctaattgat gggtcaaggg gcatcctctc tggaacatca    360
```

```
gacctgctcc ttaccttcga tgaggctgag gtccgtaaaa ttattagagt ttgcaaagga    420
attttggaat atcttacagt ggcagaggtg gtggagacta tggaagattt ggtcacttac    480
acaaagaatc ttgggccagg aatgactaag atggccaaga tgattgacga gagacagcag    540
gagctcactc accaggagca ccgagtgatg ttggtgaact cgatgaacac cgtgaaagag    600
ttgctgccag ttctcatttc agctatgaag atttttgtaa caactaaaaa ctcaaaaaac    660
caaggcatag aggaagcttt aaaaaatcgc aattttactg tagaaaaaat gagtgctgaa    720
attaatgaga taattcgtgt gttacaactc acctcttggg atgaagatgc ctgggccagc    780
aaggacactg aagccatgaa gagagcattg gcctccatag actccaaact gaaccaggcc    840
aaaggttggc tccgtgaccc tagtgcctcc ccaggggatg ctggtgagca ggccatcaga    900
cagatcttag atgaagctgg aaaagttggt gaactctgtg caggcaaaga acgcagggag    960
attctgggaa cttgcaaaat gctagggcag atgactgatc aagtggctga cctccgtgcc   1020
agaggacaag gatcctcacc ggtggccatg cagaaagctc agcaggtatc tcagggtctg   1080
gatgtgctca cagcaaaagt ggaaaatgca gctcgcaagc tggaagccat gaccaactca   1140
aagcagagca ttgcaaagaa gatcgatgct gctcagaact ggcttgcaga tccaaatggt   1200
ggaccggaag gagaagagca gattcgaggt gctttggctg aagctcggaa aatagcagaa   1260
ttatgtgatg atcctaaaga aagagatgac attctacgtt cccttgggga aatatctgct   1320
ctgacttcta aattagcaga tctacgaaga caggggaaag gagattctcc agaggctcga   1380
gccttggcca aacaggtggc cacggccctg cagaacctgc agaccaaaac caaccgggct   1440
gtggccaaca gcagaccggc caaagcagct gtacaccttg agggcaagat tgagcaagca   1500
cagcggtgga ttgataatcc cacagtggat gaccgtggag tcggtcaggc tgccatccgg   1560
gggcttgtgg ccgaagggca tcgtctggct aatgttatga tggggcctta tcggcaagat   1620
cttctcgcca agtgtgaccg agtggaccag ctgacagccc agctggctga cctggctgcc   1680
agaggggaag gggagagtcc tcaggcacga gcacttgcat ctcagctcca agactcctta   1740
aaggatctaa aagctcggat gcaggaggcc atgactcagg aagtgtcaga tgttttcagc   1800
gataccacaa ctcccatcaa gctgttggca gtggcagcca cggcgcctcc tgatgcgcct   1860
aacagggaag aggtatttga tgagagggca gctaactttg aaaaccattc aggaaagctt   1920
ggtgctacgg ccgagaaggc ggctgcggtt ggtactgcta ataaatcaac agtggaaggc   1980
attcaggcct cagtgaagac ggcccgagaa ctcacacccc aggtggtctc ggctgctcgt   2040
atcttactta ggaaccctgg aaatcaagct gcttatgaac attttgagac catgaagaac   2100
cagtggatcg ataatgttga aaaaatgaca gggctggtgg acgaagccat tgataccaaa   2160
tctctgttgg atgcttcaga agaagcaatt aaaaaagacc tggacaagtg caaggtagct   2220
atggccaaca ttcagcctca gatgctggtt gctggggcaa ccagtattgc tcgtcgggcc   2280
aaccggatcc tgctggtggc taagagggag gtggagaatt ccgaggatcc caagttccgt   2340
gaggctgtga aagctgcctc tgatgaattg agcaaaacca tctccccrat ggtgatggat   2400
gcaaaagctg tggctggaaa catttccgac cctggactgc aaaagagctt cctggactca   2460
ggatatcgga tcctgggagc tgtggccaag gtcagagaag ccttccaacc tcaggagcct   2520
gacttcccgc cgcctccacc agaccttgaa caactccgac taacagatga gcttgctcct   2580
cccaaaccac ctctgcctga aggtgaggtc cctccaccta ggcctccacc accagaggaa   2640
aaggatgaag agttccctga gcagaaggcc ggggaggtga ttaaccagcc aatgatgatg   2700
gctgccagac agctccatga tgaagctcgc aaatggtcca gcaagggcaa tgacatcatt   2760
```

-continued

```
gcagcagcca agcgcatggc tctgctgatg gctgagatgt ctcggctggt aagagggggc   2820

agtggtacca agcgggcact cattcagtgt gccaaggaca tcgccaaggc ctcagatgag   2880

gtgactcggt tggccaagga ggttgccaag cagtgcacag ataaacggat tagaaccaac   2940

ctcttacagg tatgtgagcg aatcccaacc ataagcaccc agctcaaaat cctgtccaca   3000

gtgaaggcca ccatgctggg ccggaccaac atcagtgatg aggagtctga gcaggccaca   3060

gagatgctgg ttcacaatgc ccagaacctc atgcagtctg tgaaggagac tgtgcgggaa   3120

gctgaagctg cttcaatcaa aattcgaaca gatgctggat ttacactgcg ctgggttaga   3180

aagactccct ggtaccagta g                                              3201
```

<210> SEQ ID NO 33
<211> LENGTH: 1066
<212> TYPE: PRT
<213> ORGANISM: Homo sapiens

<400> SEQUENCE: 33

```
Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285
```

```
Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
        435                 440                 445

Arg Arg Gln Gly Lys Gly Asp Ser Pro Glu Ala Arg Ala Leu Ala Lys
    450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495

Ile Glu Gln Ala Gln Arg Trp Ile Asp Asn Pro Thr Val Asp Asp Arg
            500                 505                 510

Gly Val Gly Gln Ala Ala Ile Arg Gly Leu Val Ala Glu Gly His Arg
        515                 520                 525

Leu Ala Asn Val Met Met Gly Pro Tyr Arg Gln Asp Leu Leu Ala Lys
    530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
```

```
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765

Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860

Leu Pro Glu Gly Glu Val Pro Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Gly Asn Asp Ile Ile Ala Ala Ala Lys Arg Met Ala Leu
        915                 920                 925

Leu Met Ala Glu Met Ser Arg Leu Val Arg Gly Gly Ser Gly Thr Lys
    930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
                965                 970                 975

Ile Arg Thr Asn Leu Leu Gln Val Cys Glu Arg Ile Pro Thr Ile Ser
            980                 985                 990

Thr Gln Leu Lys Ile Leu Ser Thr  Val Lys Ala Thr Met  Leu Gly Arg
        995                 1000                1005

Thr Asn  Ile Ser Asp Glu Glu  Ser Glu Gln Ala Thr  Glu Met Leu
    1010                1015                1020

Val His  Asn Ala Gln Asn Leu  Met Gln Ser Val Lys  Glu Thr Val
    1025                1030                1035

Arg Glu  Ala Glu Ala Ala Ser  Ile Lys Ile Arg Thr  Asp Ala Gly
    1040                1045                1050

Phe Thr  Leu Arg Trp Val Arg  Lys Thr Pro Trp Tyr  Gln
    1055                1060                1065
```

<210> SEQ ID NO 34
<211> LENGTH: 984
<212> TYPE: DNA
<213> ORGANISM: Homo sapiens

<400> SEQUENCE: 34

```
atgccagtgt ttcatacgcg cacgatcgag agcatcctgg agccggtggc acagcagatc      60

tcccacctgg tgataatgca cgaggagggc gaggtggacg gcaaagccat tcctgacctc     120
```

```
accgcgcccg tggccgccgt gcaggcggcc gtcagcaacc tcgtccgggt tggaaaagag    180

actgttcaaa ccactgagga tcagattttg aagagagata tgccaccagc atttattaag    240

gttgagaatg cttgcaccaa gcttgtccag gcagctcaga tgcttcagtc agacccttac    300

tcagtgcctg ctcgagatta tctaattgat gggtcaaggg gcatcctctc tggaacatca    360

gacctgctcc ttaccttcga tgaggctgag gtccctccac ctaggcctcc accaccagag    420

gaaaaggatg aagagttccc tgagcagaag gccggggagg tgattaacca gccaatgatg    480

atggctgcca gacagctcca tgatgaagct cgcaaatggt ccagcaaggg caatgacatc    540

attgcagcag ccaagcgcat ggctctgctg atggctgaga tgtctcggct ggtaagaggg    600

ggcagtggta ccaagcgggc actcattcag tgtgccaagg acatcgccaa ggcctcagat    660

gaggtgactc ggttggccaa ggaggttgcc aagcagtgca cagataaacg gattagaacc    720

aacctcttac aggtatgtga gcgaatccca accataagca cccagctcaa aatcctgtcc    780

acagtgaagg ccaccatgct gggccggacc aacatcagtg atgaggagtc tgagcaggcc    840

acagagatgc tggttcacaa tgcccagaac ctcatgcagt ctgtgaagga gactgtgcgg    900

gaagctgaag ctgcttcaat caaaattcga acagatgctg gatttacact gcgctgggtt    960

agaaagactc cctggtacca gtag                                           984
```

<210> SEQ ID NO 35
<211> LENGTH: 327
<212> TYPE: PRT
<213> ORGANISM: Homo sapiens

<400> SEQUENCE: 35

```
Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Pro Pro Pro Arg Pro Pro Pro Pro Glu Glu Lys Asp Glu
    130                 135                 140

Glu Phe Pro Glu Gln Lys Ala Gly Glu Val Ile Asn Gln Pro Met Met
145                 150                 155                 160

Met Ala Ala Arg Gln Leu His Asp Glu Ala Arg Lys Trp Ser Ser Lys
                165                 170                 175

Gly Asn Asp Ile Ile Ala Ala Ala Lys Arg Met Ala Leu Leu Met Ala
            180                 185                 190

Glu Met Ser Arg Leu Val Arg Gly Gly Ser Gly Thr Lys Arg Ala Leu
        195                 200                 205

Ile Gln Cys Ala Lys Asp Ile Ala Lys Ala Ser Asp Glu Val Thr Arg
```

```
    210                 215                 220

Leu Ala Lys Glu Val Ala Lys Gln Cys Thr Asp Lys Arg Ile Arg Thr
225                 230                 235                 240

Asn Leu Leu Gln Val Cys Glu Arg Ile Pro Thr Ile Ser Thr Gln Leu
                245                 250                 255

Lys Ile Leu Ser Thr Val Lys Ala Thr Met Leu Gly Arg Thr Asn Ile
            260                 265                 270

Ser Asp Glu Glu Ser Glu Gln Ala Thr Glu Met Leu Val His Asn Ala
        275                 280                 285

Gln Asn Leu Met Gln Ser Val Lys Glu Thr Val Arg Glu Ala Glu Ala
    290                 295                 300

Ala Ser Ile Lys Ile Arg Thr Asp Ala Gly Phe Thr Leu Arg Trp Val
305                 310                 315                 320

Arg Lys Thr Pro Trp Tyr Gln
                325
```

<210> SEQ ID NO 36
<211> LENGTH: 2619
<212> TYPE: DNA
<213> ORGANISM: Homo sapiens

<400> SEQUENCE: 36

```
atggctgagg aaaagggtgg aaagcaagtc ctggaagaat ctgcatttga agaaatggaa     60
agagattttc agggagttct ccatgaactt tctggagaca aaagtttgga aaaatttcgg    120
attgaatatg agaggcttca tgctgtcatg aaaaagtctt atgacaatga aaagcgtctg    180
atggccaaat gcagagagct aaatgcagag attgtagtga attctgcgaa ggtcgccact    240
gcccttaagc tctctcagga tgatcagacc accattgcat ccctaaagaa ggaaattgaa    300
aaggcctgga agatggtgga ctcagcctat gacaaagagc agaaggccaa ggagacgatt    360
cttgctctga aagaggaaat agtgaacctg accaaactag tggagcaggg gtctggactg    420
tcaatggacc agcatagcaa catccgagat ttactgaggt tcaaagaaga agtgacaaag    480
gagagagacc agctcttatc agaagtggta aaattacgag aatccctagc tcagaccact    540
gaacagcagc aggaaacaga gcgatcaaaa gaggaggctg aacatgccat cagtcagttc    600
caacaagaaa tccagcaacg tcagaacgaa gcttcccggg agttccggaa gaaggaaaaa    660
ctagagaaag agctcaagca gattcaggca gacatggaca gcaggcagac agaaataaaa    720
gccctgcagc agtatgtgca gaagagcaag gaggagcttc agaagctgga gcagcagctg    780
aaggagcaga agatattgaa tgagagagct gcaaaggaac tcgagcaatt tcagatgaga    840
aatgctaaac ttcagcaaga gaatgaacag cacagtttgg tctgtgagca gctatcccag    900
gaaaaccaac agaaggcgtt ggagctcaaa gccaaagagg aagaagtcca tcaaatgcgc    960
cttgacatcg ggaagctcaa caaaatcaga gaacaaattc ataagaaatt gcaccacacc   1020
gaagatcaaa aggcagaagt cgaacagcac aaagaaaccc taaaaaatca gattgtggga   1080
ttagagagag aggtagaggc ttcaaagaaa caagcagaac ttgacagaaa ggcaatggac   1140
gagcttctaa gagaaaggga catactaaat aagaacatgc ttaaggcggt caatgcgacc   1200
cagaagcaga cagacttggt aaagctccat gaacaagcca agaggaacct ggagggagaa   1260
atccagaact acaaggatga ggctcagaag cagagaaaga tcatctttca tctggaaaag   1320
gagcgtgacc ggtacatcaa ccaagccagt gaccttacgc aaaaggtcct tatgaacatg   1380
gaagacataa aagttcgtga aacacagatt tttgactaca ggaaaaaaat agctgaatca   1440
```

```
gagattaaat taaaacagca acagaaccta tatgaagctg tgagatcaga cagaaatctg   1500

tatagcaaaa atctggttga ggctcaggat gaaataacag atatgaagag aaagttaaag   1560

attatgatcc atcaggtaga tgagctgaaa gaagacatct ctgccaaaga gtccgcactt   1620

gtgaagctgc acctggaaca gcagcgaata gaaaaggaaa aggaaacatt gaaggctgag   1680

ctgcagaagc tgagacaaca agccctggag acaaaacact ttattgaaaa gcaagaagct   1740

gaagagagaa aactcctgcg aataattgct gaggctgacg gggagaggtt gagacagaag   1800

aaggaattag accaggtcat cagtgagaga gatatcctgg ggtctcagct tgttcggcgc   1860

aatgatgagt tagctttgct ctatgagaag atcaagatcc aacagtctgt gctgaataaa   1920

ggggagagcc agtacaacca gaggttggag gacatgagaa tcctcagact tgagatcaag   1980

aagcttcgcc gggaaaaggg gattcttgcc aggagtatgg ctaatgttga agaactcaga   2040

caggagtttt ttcacatgca aagagaattg ttgaaggaga ggacacgctg ccgagccctg   2100

gaggaggagc tggagaatcc cctgaatgtg cacagatgga ggaagctcga ggccagcgac   2160

cccaatgcat atgagctgat acagaaaatt cacaccctgc agaagcgtct catcagcaag   2220

actgaagagg tggttgaaaa agagctgctc ctccaggaaa aggagaaact ctacatggaa   2280

ctaaagcacg tcttggcccg ccagcctgga cctgaggctg cggaacagct gaagctgtac   2340

cgacgcacgc tgcatgacaa gaagcagcag ctgaaagttt tgtcttcaga attgaatatg   2400

tatgaagtac agagcaaaga atataaatat gaggtagaga aacttaccaa tgagctccag   2460

aatttaaaga agaaatacct cgctcagaaa cgtaaagaac aacttcaaaa aaacaaggac   2520

acagcaccca tggataacac cttcttaatg gtcaaaccaa atggtcctgg ttttactggg   2580

ggcggatttc ctctcaggtc aaccaaaatg acgttctaa                          2619
```

<210> SEQ ID NO 37
<211> LENGTH: 872
<212> TYPE: PRT
<213> ORGANISM: Homo sapiens

<400> SEQUENCE: 37

```
Met Ala Glu Glu Lys Gly Gly Lys Gln Val Leu Glu Glu Ser Ala Phe
1               5                   10                  15

Glu Glu Met Glu Arg Asp Phe Gln Gly Val Leu His Glu Leu Ser Gly
            20                  25                  30

Asp Lys Ser Leu Glu Lys Phe Arg Ile Glu Tyr Glu Arg Leu His Ala
        35                  40                  45

Val Met Lys Lys Ser Tyr Asp Asn Glu Lys Arg Leu Met Ala Lys Cys
    50                  55                  60

Arg Glu Leu Asn Ala Glu Ile Val Val Asn Ser Ala Lys Val Ala Thr
65                  70                  75                  80

Ala Leu Lys Leu Ser Gln Asp Asp Gln Thr Thr Ile Ala Ser Leu Lys
                85                  90                  95

Lys Glu Ile Glu Lys Ala Trp Lys Met Val Asp Ser Ala Tyr Asp Lys
            100                 105                 110

Glu Gln Lys Ala Lys Glu Thr Ile Leu Ala Leu Lys Glu Glu Ile Val
        115                 120                 125

Asn Leu Thr Lys Leu Val Glu Gln Gly Ser Gly Leu Ser Met Asp Gln
    130                 135                 140

His Ser Asn Ile Arg Asp Leu Leu Arg Phe Lys Glu Glu Val Thr Lys
145                 150                 155                 160

Glu Arg Asp Gln Leu Leu Ser Glu Val Val Lys Leu Arg Glu Ser Leu
```

```
                165                 170                 175

Ala Gln Thr Thr Glu Gln Gln Gln Glu Thr Glu Arg Ser Lys Glu Glu
            180                 185                 190

Ala Glu His Ala Ile Ser Gln Phe Gln Gln Glu Ile Gln Gln Arg Gln
        195                 200                 205

Asn Glu Ala Ser Arg Glu Phe Arg Lys Lys Glu Lys Leu Glu Lys Glu
    210                 215                 220

Leu Lys Gln Ile Gln Ala Asp Met Asp Ser Arg Gln Thr Glu Ile Lys
225                 230                 235                 240

Ala Leu Gln Gln Tyr Val Gln Lys Ser Lys Glu Glu Leu Gln Lys Leu
                245                 250                 255

Glu Gln Gln Leu Lys Glu Gln Lys Ile Leu Asn Glu Arg Ala Ala Lys
            260                 265                 270

Glu Leu Glu Gln Phe Gln Met Arg Asn Ala Lys Leu Gln Gln Glu Asn
        275                 280                 285

Glu Gln His Ser Leu Val Cys Glu Gln Leu Ser Gln Glu Asn Gln Gln
    290                 295                 300

Lys Ala Leu Glu Leu Lys Ala Lys Glu Glu Glu Val His Gln Met Arg
305                 310                 315                 320

Leu Asp Ile Gly Lys Leu Asn Lys Ile Arg Glu Gln Ile His Lys Lys
                325                 330                 335

Leu His His Thr Glu Asp Gln Lys Ala Glu Val Glu Gln His Lys Glu
            340                 345                 350

Thr Leu Lys Asn Gln Ile Val Gly Leu Glu Arg Glu Val Glu Ala Ser
        355                 360                 365

Lys Lys Gln Ala Glu Leu Asp Arg Lys Ala Met Asp Glu Leu Leu Arg
    370                 375                 380

Glu Arg Asp Ile Leu Asn Lys Asn Met Leu Lys Ala Val Asn Ala Thr
385                 390                 395                 400

Gln Lys Gln Thr Asp Leu Val Lys Leu His Glu Gln Ala Lys Arg Asn
                405                 410                 415

Leu Glu Gly Glu Ile Gln Asn Tyr Lys Asp Glu Ala Gln Lys Gln Arg
            420                 425                 430

Lys Ile Ile Phe His Leu Glu Lys Glu Arg Asp Arg Tyr Ile Asn Gln
        435                 440                 445

Ala Ser Asp Leu Thr Gln Lys Val Leu Met Asn Met Glu Asp Ile Lys
    450                 455                 460

Val Arg Glu Thr Gln Ile Phe Asp Tyr Arg Lys Lys Ile Ala Glu Ser
465                 470                 475                 480

Glu Ile Lys Leu Lys Gln Gln Gln Asn Leu Tyr Glu Ala Val Arg Ser
                485                 490                 495

Asp Arg Asn Leu Tyr Ser Lys Asn Leu Val Glu Ala Gln Asp Glu Ile
            500                 505                 510

Thr Asp Met Lys Arg Lys Leu Lys Ile Met Ile His Gln Val Asp Glu
        515                 520                 525

Leu Lys Glu Asp Ile Ser Ala Lys Glu Ser Ala Leu Val Lys Leu His
    530                 535                 540

Leu Glu Gln Gln Arg Ile Glu Lys Glu Lys Glu Thr Leu Lys Ala Glu
545                 550                 555                 560

Leu Gln Lys Leu Arg Gln Gln Ala Leu Glu Thr Lys His Phe Ile Glu
                565                 570                 575

Lys Gln Glu Ala Glu Glu Arg Lys Leu Leu Arg Ile Ile Ala Glu Ala
            580                 585                 590
```

```
Asp Gly Glu Arg Leu Arg Gln Lys Lys Glu Leu Asp Gln Val Ile Ser
        595                 600                 605

Glu Arg Asp Ile Leu Gly Ser Gln Leu Val Arg Arg Asn Asp Glu Leu
    610                 615                 620

Ala Leu Leu Tyr Glu Lys Ile Lys Ile Gln Gln Ser Val Leu Asn Lys
625                 630                 635                 640

Gly Glu Ser Gln Tyr Asn Gln Arg Leu Glu Asp Met Arg Ile Leu Arg
                645                 650                 655

Leu Glu Ile Lys Lys Leu Arg Arg Glu Lys Gly Ile Leu Ala Arg Ser
            660                 665                 670

Met Ala Asn Val Glu Glu Leu Arg Gln Glu Phe Phe His Met Gln Arg
        675                 680                 685

Glu Leu Leu Lys Glu Arg Thr Arg Cys Arg Ala Leu Glu Glu Glu Leu
    690                 695                 700

Glu Asn Pro Leu Asn Val His Arg Trp Arg Lys Leu Glu Ala Ser Asp
705                 710                 715                 720

Pro Asn Ala Tyr Glu Leu Ile Gln Lys Ile His Thr Leu Gln Lys Arg
                725                 730                 735

Leu Ile Ser Lys Thr Glu Glu Val Val Glu Lys Glu Leu Leu Leu Gln
            740                 745                 750

Glu Lys Glu Lys Leu Tyr Met Glu Leu Lys His Val Leu Ala Arg Gln
        755                 760                 765

Pro Gly Pro Glu Ala Ala Glu Gln Leu Lys Leu Tyr Arg Arg Thr Leu
    770                 775                 780

His Asp Lys Lys Gln Gln Leu Lys Val Leu Ser Ser Glu Leu Asn Met
785                 790                 795                 800

Tyr Glu Val Gln Ser Lys Glu Tyr Lys Tyr Glu Val Glu Lys Leu Thr
                805                 810                 815

Asn Glu Leu Gln Asn Leu Lys Lys Lys Tyr Leu Ala Gln Lys Arg Lys
            820                 825                 830

Glu Gln Leu Gln Lys Asn Lys Asp Thr Ala Pro Met Asp Asn Thr Phe
        835                 840                 845

Leu Met Val Lys Pro Asn Gly Pro Gly Phe Thr Gly Gly Gly Phe Pro
    850                 855                 860

Leu Arg Ser Thr Lys Met Thr Phe
865                 870
```

<210> SEQ ID NO 38
<211> LENGTH: 2469
<212> TYPE: DNA
<213> ORGANISM: Homo sapiens

<400> SEQUENCE: 38

```
atggtcagct ggggtcgttt catctgcctg gtcgtggtca ccatggcaac cttgtccctg      60

gcccggccct ccttcagttt agttgaggat accacattag agccagaaga gccaccaacc     120

aaataccaaa tctctcaacc agaagtgtac gtggctgcgc caggggagtc gctagaggtg     180

cgctgcctgt tgaaagatgc cgccgtgatc agttggacta aggatggggt gcacttgggg     240

cccaacaata ggacagtgct tattggggag tacttgcaga taaagggcgc cacgcctaga     300

gactccggcc tctatgcttg tactgccagt aggactgtag acagtgaaac ttggtacttc     360

atggtgaatg tcacagatgc catctcatcc ggagatgatg aggatgacac cgatggtgcg     420

gaagattttg tcagtgagaa cagtaacaac aagagagcac catactggac caacacagaa     480
```

```
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagc actcggggat aaatagttcc    960
aatgcagaag tgctggctct gttcaatgtg accgaggcgg atgctgggga atatatatgt   1020
aaggtctcca attatatagg gcaggccaac cagtctgcct ggctcactgt cctgccaaaa   1080
cagcaagcgc ctggaagaga aaaggagatt acagcttccc cagactacct ggagatagcc   1140
atttactgca taggggtctt cttaatcgcc tgtatggtgg taacagtcat cctgtgccga   1200
atgaagaaca cgaccaagaa gccagacttc agcagccagc cggctgtgca caagctgacc   1260
aaacgtatcc ccctgcggag acaggtaaca gtttcggctg agtccagctc ctccatgaac   1320
tccaacaccc cgctggtgag gataacaaca cgcctctctt caacggcaga cacccccatg   1380
ctggcagggg tctccgagta tgaacttcca gaggacccaa aatgggagtt tccaagagat   1440
aagctgacac tgggcaagcc cctgggagaa ggttgctttg ggcaagtggt catggcggaa   1500
gcagtgggaa ttgacaaaga caagcccaag gaggcggtca ccgtggccgt gaagatgttg   1560
aaagatgatg ccacagagaa agacctttct gatctggtgt cagagatgga gatgatgaag   1620
atgattggga aacacaagaa tatcataaat cttcttggag cctgcacaca ggatgggcct   1680
ctctatgtca tagttgagta tgcctctaaa ggcaacctcc gagaatacct ccgagcccgg   1740
aggccacccg ggatggagta ctcctatgac attaaccgtg ttcctgagga gcagatgacc   1800
ttcaaggact tggtgtcatg cacctaccag ctggccagag gcatggagta cttggcttcc   1860
caaaaatgta ttcatcgaga tttagcagcc agaaatgttt tggtaacaga aaacaatgtg   1920
atgaaaatag cagactttgg actcgccaga gatatcaaca atatagacta ttacaaaaag   1980
accaccaatg ggcggcttcc agtcaagtgg atggctccag aagccctgtt tgatagagta   2040
tacactcatc agagtgatgt ctggtccttc ggggtgttaa tgtgggagat cttcacttta   2100
gggggctcgc cctacccagg gattcccgtg gaggaacttt ttaagctgct gaaggaagga   2160
cacagaatgg ataagccagc caactgcacc aacgaactgt acatgatgat gagggactgt   2220
tggcatgcag tgccctccca gagaccaacg ttcaagcagt tggtagaaga cttggatcga   2280
attctcactc tcacaaccaa tgaggaatac ttggacctca gccaacctct cgaacagtat   2340
tcacctagtt accctgacac aagaagttct tgttcttcag gagatgattc tgtttttct    2400
ccagacccca tgccttacga accatgcctt cctcagtatc cacacataaa cggcagtgtt   2460
aaaacatga                                                            2469
```

<210> SEQ ID NO 39
<211> LENGTH: 822
<212> TYPE: PRT
<213> ORGANISM: Homo sapiens

<400> SEQUENCE: 39

```
Met Val Ser Trp Gly Arg Phe Ile Cys Leu Val Val Val Thr Met Ala
1               5                   10                  15
```

```
Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
```

```
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820
```

<210> SEQ ID NO 40
<211> LENGTH: 2460
<212> TYPE: DNA
<213> ORGANISM: Homo sapiens

<400> SEQUENCE: 40

```
atggtcagct ggggtcgttt catctgcctg gtcgtggtca ccatggcaac cttgtccctg     60
gcccggccct ccttcagttt agttgaggat accacattag agccagaaga gccaccaacc    120
aaataccaaa tctctcaacc agaagtgtac gtggctgcgc caggggagtc gctagaggtg    180
cgctgcctgt tgaaagatgc cgccgtgatc agttggacta aggatggggt gcacttgggg    240
cccaacaata ggacagtgct tattggggag tacttgcaga taaagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtttcggct gagtccagct cctccatgaa ctccaacacc   1320
ccgctggtga ggataacaac acgcctctct tcaacggcag acacccccat gctggcaggg   1380
gtctccgagt atgaacttcc agaggaccca aaatgggagt ttccaagaga taagctgaca   1440
ctgggcaagc ccctgggaga aggttgcttt gggcaagtgg tcatggcgga agcagtggga   1500
attgacaaag acaagcccaa ggaggcggtc accgtggccg tgaagatgtt gaaagatgat   1560
gccacagaga aagacctttc tgatctggtg tcagagatgg agatgatgaa gatgattggg   1620
aaacacaaga atatcataaa tcttcttgga gcctgcacac aggatgggcc tctctatgtc   1680
atagttgagt atgcctctaa aggcaacctc cgagaatacc tccgagcccg gaggccaccc   1740
gggatggagt actcctatga cattaaccgt gttcctgagg agcagatgac cttcaaggac   1800
ttggtgtcat gcacctacca gctggccaga ggcatggagt acttggcttc ccaaaaatgt   1860
attcatcgag atttagcagc cagaaatgtt ttggtaacag aaaacaatgt gatgaaaata   1920
gcagactttg gactcgccag agatatcaac aatatagact attacaaaaa gaccaccaat   1980
gggcggcttc cagtcaagtg gatggctcca gaagccctgt ttgatagagt atacactcat   2040
cagagtgatg tctggtcctt cggggtgtta atgtgggaga tcttcacttt agggggctcg   2100
ccctacccag ggattcccgt ggaggaactt tttaagctgc tgaaggaagg acacagaatg   2160
gataagccag ccaactgcac caacgaactg tacatgatga tgagggactg ttggcatgca   2220
gtgccctccc agagaccaac gttcaagcag ttggtagaag acttggatcg aattctcact   2280
```

```
ctcacaacca atgaggaata cttggacctc agccaacctc tcgaacagta ttcacctagt   2340

taccctgaca caagaagttc ttgttcttca ggagatgatt ctgtttttc tccagacccc    2400

atgccttacg aaccatgcct tcctcagtat ccacacataa acggcagtgt taaaacatga   2460


<210> SEQ ID NO 41
<211> LENGTH: 819
<212> TYPE: PRT
<213> ORGANISM: Homo sapiens

<400> SEQUENCE: 41

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350
```

```
His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Ser Ala Glu Ser
            420                 425                 430

Ser Ser Ser Met Asn Ser Asn Thr Pro Leu Val Arg Ile Thr Thr Arg
        435                 440                 445

Leu Ser Ser Thr Ala Asp Thr Pro Met Leu Ala Gly Val Ser Glu Tyr
    450                 455                 460

Glu Leu Pro Glu Asp Pro Lys Trp Glu Phe Pro Arg Asp Lys Leu Thr
465                 470                 475                 480

Leu Gly Lys Pro Leu Gly Glu Gly Cys Phe Gly Gln Val Val Met Ala
                485                 490                 495

Glu Ala Val Gly Ile Asp Lys Asp Lys Pro Lys Glu Ala Val Thr Val
            500                 505                 510

Ala Val Lys Met Leu Lys Asp Asp Ala Thr Glu Lys Asp Leu Ser Asp
        515                 520                 525

Leu Val Ser Glu Met Glu Met Met Lys Met Ile Gly Lys His Lys Asn
    530                 535                 540

Ile Ile Asn Leu Leu Gly Ala Cys Thr Gln Asp Gly Pro Leu Tyr Val
545                 550                 555                 560

Ile Val Glu Tyr Ala Ser Lys Gly Asn Leu Arg Glu Tyr Leu Arg Ala
                565                 570                 575

Arg Arg Pro Pro Gly Met Glu Tyr Ser Tyr Asp Ile Asn Arg Val Pro
            580                 585                 590

Glu Glu Gln Met Thr Phe Lys Asp Leu Val Ser Cys Thr Tyr Gln Leu
        595                 600                 605

Ala Arg Gly Met Glu Tyr Leu Ala Ser Gln Lys Cys Ile His Arg Asp
    610                 615                 620

Leu Ala Ala Arg Asn Val Leu Val Thr Glu Asn Asn Val Met Lys Ile
625                 630                 635                 640

Ala Asp Phe Gly Leu Ala Arg Asp Ile Asn Asn Ile Asp Tyr Tyr Lys
                645                 650                 655

Lys Thr Thr Asn Gly Arg Leu Pro Val Lys Trp Met Ala Pro Glu Ala
            660                 665                 670

Leu Phe Asp Arg Val Tyr Thr His Gln Ser Asp Val Trp Ser Phe Gly
        675                 680                 685

Val Leu Met Trp Glu Ile Phe Thr Leu Gly Gly Ser Pro Tyr Pro Gly
    690                 695                 700

Ile Pro Val Glu Glu Leu Phe Lys Leu Leu Lys Glu Gly His Arg Met
705                 710                 715                 720

Asp Lys Pro Ala Asn Cys Thr Asn Glu Leu Tyr Met Met Met Arg Asp
                725                 730                 735

Cys Trp His Ala Val Pro Ser Gln Arg Pro Thr Phe Lys Gln Leu Val
            740                 745                 750

Glu Asp Leu Asp Arg Ile Leu Thr Leu Thr Thr Asn Glu Glu Tyr Leu
        755                 760                 765
```

```
Asp Leu Ser Gln Pro Leu Glu Gln Tyr Ser Pro Ser Tyr Pro Asp Thr
    770                 775                 780

Arg Ser Ser Cys Ser Ser Gly Asp Asp Ser Val Phe Ser Pro Asp Pro
785                 790                 795                 800

Met Pro Tyr Glu Pro Cys Leu Pro Gln Tyr Pro His Ile Asn Gly Ser
                805                 810                 815

Val Lys Thr


<210> SEQ ID NO 42
<211> LENGTH: 2310
<212> TYPE: DNA
<213> ORGANISM: Homo sapiens

<400> SEQUENCE: 42

atggtcagct ggggtcgttt catctgcctg gtcgtggtca ccatggcaac cttgtccctg     60

gcccggccct ccttcagttt agttgaggat accacattag agccagaaga gccaccaacc    120

aaataccaaa tctctcaacc agaagtgtac gtggctgcgc caggggagtc gctagaggtg    180

cgctgcctgt tgaaagatgc cgccgtgatc agttggacta aggatggggt gcacttgggg    240

cccaacaata ggacagtgct tattggggag tacttgcaga taaagggcgc cacgcctaga    300

gactccggcc tctatgcttg tactgccagt aggactgtag acagtgaaac ttggtacttc    360

atggtgaatg tcacagatgc catctcatcc ggagatgatg aggatgacac cgatggtgcg    420

gaagattttg tcagtgagaa cagtaacaac aagagagcac catactggac caacacagaa    480

aagatggaaa agcggctcca tgctgtgcct gcggccaaca ctgtcaagtt tcgctgccca    540

gccgggggga acccaatgcc aaccatgcgg tggctgaaaa acgggaagga gtttaagcag    600

gagcatcgca ttggaggcta caaggtacga aaccagcact ggagcctcat tatggaaagt    660

gtggtcccat ctgacaaggg aaattatacc tgtgtagtgg agaatgaata cgggtccatc    720

aatcacacgt accacctgga tgttgtggag cgatcgcctc accggcccat cctccaagcc    780

ggactgccgg caaatgcctc cacagtggtc ggaggagacg tagagtttgt ctgcaaggtt    840

tacagtgatg cccagcccca catccagtgg atcaagcacg tggaaaagaa cggcagtaaa    900

tacgggcccg acgggctgcc ctacctcaag gttctcaagc actcggggat aaatagttcc    960

aatgcagaag tgctggctct gttcaatgtg accgaggcgg atgctgggga atatatatgt   1020

aaggtctcca attatatagg gcaggccaac cagtctgcct ggctcactgt cctgccaaaa   1080

cagcaagcgc ctggaagaga aaaggagatt acagcttccc cagactacct ggagatagcc   1140

atttactgca taggggtctt cttaatcgcc tgtatggtgg taacagtcat cctgtgccga   1200

atgaagaaca cgaccaagaa gccagacttc agcagccagc cggctgtgca caagctgacc   1260

aaacgtatcc ccctgcggag acaggtaaca gtttcggctg agtccagctc ctccatgaac   1320

tccaacaccc cgctggtgag gataacaaca cgcctctctt caacggcaga cacccccatg   1380

ctggcagggg tctccgagta tgaacttcca gaggacccaa aatgggagtt tccaagagat   1440

aagctgacac tgggcaagcc cctgggagaa ggttgctttg ggcaagtggt catggcggaa   1500

gcagtgggaa ttgacaaaga caagcccaag gaggcggtca ccgtggccgt gaagatgttg   1560

aaagatgatg ccacagagaa agacctttct gatctggtgt cagagatgga gatgatgaag   1620

atgattggga aacacaagaa tatcataaat cttcttggag cctgcacaca ggatgggcct   1680

ctctatgtca tagttgagta tgcctctaaa ggcaacctcc gagaatacct ccgagcccgg   1740

aggccacccg ggatggagta ctcctatgac attaaccgtg ttcctgagga gcagatgacc   1800
```

```
ttcaaggact tggtgtcatg cacctaccag ctggccagag gcatggagta cttggcttcc   1860

caaaaatgta ttcatcgaga tttagcagcc agaaatgttt tggtaacaga aaacaatgtg   1920

atgaaaatag cagactttgg actcgccaga gatatcaaca atatagacta ttacaaaaag   1980

accaccaatg gcggcttcc agtcaagtgg atggctccag aagccctgtt tgatagagta    2040

tacactcatc agagtgatgt ctggtccttc ggggtgttaa tgtgggagat cttcacttta   2100

gggggctcgc cctacccagg gattcccgtg gaggaacttt ttaagctgct gaaggaagga   2160

cacagaatgg ataagccagc caactgcacc aacgaactgt acatgatgat gagggactgt   2220

tggcatgcag tgccctccca gagaccaacg ttcaagcagt tggtagaaga cttggatcga   2280

attctcactc tcacaaccaa tgagatctga                                    2310


<210> SEQ ID NO 43
<211> LENGTH: 769
<212> TYPE: PRT
<213> ORGANISM: Homo sapiens

<400> SEQUENCE: 43

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285
```

```
Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700
```

```
Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Ile


<210> SEQ ID NO 44
<211> LENGTH: 2304
<212> TYPE: DNA
<213> ORGANISM: Homo sapiens

<400> SEQUENCE: 44

atggtcagct ggggtcgttt catctgcctg gtcgtggtca ccatggcaac cttgtccctg      60

gcccggccct ccttcagttt agttgaggat accacattag agccagaaga gccaccaacc     120

aaataccaaa tctctcaacc agaagtgtac gtggctgcgc caggggagtc gctagaggtg     180

cgctgcctgt tgaaagatgc cgccgtgatc agttggacta aggatggggt gcacttgggg     240

cccaacaata ggacagtgct tattggggag tacttgcaga taaagggcgc cacgcctaga     300

gactccggcc tctatgcttg tactgccagt aggactgtag acagtgaaac ttggtacttc     360

atggtgaatg tcacagatgc catctcatcc ggagatgatg aggatgacac cgatggtgcg     420

gaagattttg tcagtgagaa cagtaacaac aagagagcac catactggac caacacagaa     480

aagatggaaa agcggctcca tgctgtgcct gcggccaaca ctgtcaagtt tcgctgccca     540

gccgggggga acccaatgcc aaccatgcgg tggctgaaaa acgggaagga gtttaagcag     600

gagcatcgca ttggaggcta caaggtacga aaccagcact ggagcctcat tatggaaagt     660

gtggtcccat ctgacaaggg aaattatacc tgtgtagtgg agaatgaata cgggtccatc     720

aatcacacgt accacctgga tgttgtggag cgatcgcctc accggcccat cctccaagcc     780

ggactgccgg caaatgcctc cacagtggtc ggaggagacg tagagtttgt ctgcaaggtt     840

tacagtgatg cccagcccca catccagtgg atcaagcacg tggaaaagaa cggcagtaaa     900

tacgggcccg acgggctgcc ctacctcaag gttctcaagc actcggggat aaatagttcc     960

aatgcagaag tgctggctct gttcaatgtg accgaggcgg atgctgggga atatatatgt    1020

aaggtctcca attatatagg gcaggccaac cagtctgcct ggctcactgt cctgccaaaa    1080

cagcaagcgc ctggaagaga aaaggagatt acagcttccc cagactacct ggagatagcc    1140

atttactgca taggggtctt cttaatcgcc tgtatggtgg taacagtcat cctgtgccga    1200

atgaagaaca cgaccaagaa gccagacttc agcagccagc cggctgtgca caagctgacc    1260

aaacgtatcc ccctgcggag acaggtaaca gtttcggctg agtccagctc ctccatgaac    1320

tccaacaccc cgctggtgag gataacaaca cgcctctctt caacggcaga cacccccatg    1380

ctggcagggg tctccgagta tgaacttcca gaggacccaa aatgggagtt tccaagagat    1440

aagctgacac tgggcaagcc cctgggagaa ggttgctttg ggcaagtggt catggcggaa    1500

gcagtgggaa ttgacaaaga caagcccaag gaggcggtca ccgtggccgt gaagatgttg    1560

aaagatgatg ccacagagaa agacctttct gatctggtgt cagagatgga gatgatgaag    1620

atgattggga aacacaagaa tatcataaat cttcttggag cctgcacaca ggatgggcct    1680

ctctatgtca tagttgagta tgcctctaaa ggcaacctcc gagaatacct ccgagcccgg    1740
```

```
aggccacccg ggatggagta ctcctatgac attaaccgtg ttcctgagga gcagatgacc   1800

ttcaaggact tggtgtcatg cacctaccag ctggccagag gcatggagta cttggcttcc   1860

caaaaatgta ttcatcgaga tttagcagcc agaaatgttt tggtaacaga aaacaatgtg   1920

atgaaaatag cagactttgg actcgccaga gatatcaaca atatagacta ttacaaaaag   1980

accaccaatg ggcggcttcc agtcaagtgg atggctccag aagccctgtt tgatagagta   2040

tacactcatc agagtgatgt ctggtccttc ggggtgttaa tgtgggagat cttcacttta   2100

gggggctcgc cctacccagg gattcccgtg gaggaacttt ttaagctgct gaaggaagga   2160

cacagaatgg ataagccagc caactgcacc aacgaactgt acatgatgat gagggactgt   2220

tggcatgcag tgccctccca gagaccaacg ttcaagcagt tggtagaaga cttggatcga   2280

attctcactc tcacaaccaa tgag                                          2304
```

<210> SEQ ID NO 45
<211> LENGTH: 768
<212> TYPE: PRT
<213> ORGANISM: Homo sapiens

<400> SEQUENCE: 45

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270
```

```
Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685
```

```
Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765


<210> SEQ ID NO 46
<211> LENGTH: 2130
<212> TYPE: DNA
<213> ORGANISM: Homo sapiens

<400> SEQUENCE: 46

atggtcagct ggggtcgttt catctgcctg gtcgtggtca ccatggcaac cttgtccctg      60

gcccggccct ccttcagttt agttgaggat accacattag agccagaaga gccaccaacc     120

aaataccaaa tctctcaacc agaagtgtac gtggctgcgc caggggagtc gctagaggtg     180

cgctgcctgt tgaaagatgc cgccgtgatc agttggacta aggatggggt gcacttgggg     240

cccaacaata ggacagtgct tattggggag tacttgcaga taaagggcgc cacgcctaga     300

gactccggcc tctatgcttg tactgccagt aggactgtag acagtgaaac ttggtacttc     360

atggtgaatg tcacagatgc catctcatcc ggagatgatg aggatgacac cgatggtgcg     420

gaagattttg tcagtgagaa cagtaacaac aagagagcac catactggac caacacagaa     480

aagatggaaa agcggctcca tgctgtgcct gcggccaaca ctgtcaagtt tcgctgccca     540

gccgggggga acccaatgcc aaccatgcgg tggctgaaaa acgggaagga gtttaagcag     600

gagcatcgca ttggaggcta caaggtacga aaccagcact ggagcctcat tatggaaagt     660

gtggtcccat ctgacaaggg aaattatacc tgtgtagtgg agaatgaata cgggtccatc     720

aatcacacgt accacctgga tgttgtggcg cctggaagag aaaaggagat tacagcttcc     780

ccagactacc tggagatagc catttactgc ataggggtct tcttaatcgc ctgtatggtg     840

gtaacagtca tcctgtgccg aatgaagaac acgaccaaga agccagactt cagcagccag     900

ccggctgtgc acaagctgac caaacgtatc cccctgcgga gacaggtaac agtttcggct     960

gagtccagct cctccatgaa ctccaacacc ccgctggtga ggataacaac acgcctctct    1020

tcaacggcag acacccccat gctggcaggg gtctccgagt atgaacttcc agaggaccca    1080

aaatgggagt ttccaagaga taagctgaca ctgggcaagc ccctgggaga aggttgcttt    1140

gggcaagtgg tcatggcgga agcagtggga attgacaaag acaagcccaa ggaggcggtc    1200

accgtggccg tgaagatgtt gaaagatgat gccacagaga aagacctttc tgatctggtg    1260

tcagagatgg agatgatgaa gatgattggg aaacacaaga atatcataaa tcttcttgga    1320

gcctgcacac aggatgggcc tctctatgtc atagttgagt atgcctctaa aggcaacctc    1380

cgagaatacc tccgagcccg gaggccaccc gggatggagt actcctatga cattaaccgt    1440

gttcctgagg agcagatgac cttcaaggac ttggtgtcat gcacctacca gctggccaga    1500

ggcatggagt acttggcttc ccaaaaatgt attcatcgag atttagcagc cagaaatgtt    1560

ttggtaacag aaaacaatgt gatgaaaata gcagactttg gactcgccag agatatcaac    1620

aatatagact attacaaaaa gaccaccaat gggcggcttc cagtcaagtg gatggctcca    1680
```

```
gaagccctgt ttgatagagt atacactcat cagagtgatg tctggtcctt cggggtgtta   1740

atgtgggaga tcttcacttt agggggctcg ccctacccag ggattcccgt ggaggaactt   1800

tttaagctgc tgaaggaagg acacagaatg gataagccag ccaactgcac caacgaactg   1860

tacatgatga tgagggactg ttggcatgca gtgccctccc agagaccaac gttcaagcag   1920

ttggtagaag acttggatcg aattctcact ctcacaacca atgaggaata cttggacctc   1980

agccaacctc tcgaacagta ttcacctagt taccctgaca caagaagttc ttgttcttca   2040

ggagatgatt ctgtttttc tccagacccc atgccttacg aaccatgcct tcctcagtat    2100

ccacacataa acggcagtgt taaaacatga                                    2130
```

<210> SEQ ID NO 47
<211> LENGTH: 709
<212> TYPE: PRT
<213> ORGANISM: Homo sapiens

<400> SEQUENCE: 47

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Ala Pro Gly Arg Glu Lys Glu
                245                 250                 255

Ile Thr Ala Ser Pro Asp Tyr Leu Glu Ile Ala Ile Tyr Cys Ile Gly
            260                 265                 270

Val Phe Leu Ile Ala Cys Met Val Val Thr Val Ile Leu Cys Arg Met
        275                 280                 285

Lys Asn Thr Thr Lys Lys Pro Asp Phe Ser Ser Gln Pro Ala Val His
```

```
    290                 295                 300

Lys Leu Thr Lys Arg Ile Pro Leu Arg Arg Gln Val Thr Val Ser Ala
305                 310                 315                 320

Glu Ser Ser Ser Ser Met Asn Ser Asn Thr Pro Leu Val Arg Ile Thr
                325                 330                 335

Thr Arg Leu Ser Ser Thr Ala Asp Thr Pro Met Leu Ala Gly Val Ser
            340                 345                 350

Glu Tyr Glu Leu Pro Glu Asp Pro Lys Trp Glu Phe Pro Arg Asp Lys
        355                 360                 365

Leu Thr Leu Gly Lys Pro Leu Gly Glu Gly Cys Phe Gly Gln Val Val
    370                 375                 380

Met Ala Glu Ala Val Gly Ile Asp Lys Asp Lys Pro Lys Glu Ala Val
385                 390                 395                 400

Thr Val Ala Val Lys Met Leu Lys Asp Asp Ala Thr Glu Lys Asp Leu
                405                 410                 415

Ser Asp Leu Val Ser Glu Met Glu Met Met Lys Met Ile Gly Lys His
            420                 425                 430

Lys Asn Ile Ile Asn Leu Leu Gly Ala Cys Thr Gln Asp Gly Pro Leu
        435                 440                 445

Tyr Val Ile Val Glu Tyr Ala Ser Lys Gly Asn Leu Arg Glu Tyr Leu
    450                 455                 460

Arg Ala Arg Arg Pro Pro Gly Met Glu Tyr Ser Tyr Asp Ile Asn Arg
465                 470                 475                 480

Val Pro Glu Glu Gln Met Thr Phe Lys Asp Leu Val Ser Cys Thr Tyr
                485                 490                 495

Gln Leu Ala Arg Gly Met Glu Tyr Leu Ala Ser Gln Lys Cys Ile His
            500                 505                 510

Arg Asp Leu Ala Ala Arg Asn Val Leu Val Thr Glu Asn Asn Val Met
        515                 520                 525

Lys Ile Ala Asp Phe Gly Leu Ala Arg Asp Ile Asn Asn Ile Asp Tyr
    530                 535                 540

Tyr Lys Lys Thr Thr Asn Gly Arg Leu Pro Val Lys Trp Met Ala Pro
545                 550                 555                 560

Glu Ala Leu Phe Asp Arg Val Tyr Thr His Gln Ser Asp Val Trp Ser
                565                 570                 575

Phe Gly Val Leu Met Trp Glu Ile Phe Thr Leu Gly Gly Ser Pro Tyr
            580                 585                 590

Pro Gly Ile Pro Val Glu Glu Leu Phe Lys Leu Leu Lys Glu Gly His
        595                 600                 605

Arg Met Asp Lys Pro Ala Asn Cys Thr Asn Glu Leu Tyr Met Met Met
    610                 615                 620

Arg Asp Cys Trp His Ala Val Pro Ser Gln Arg Pro Thr Phe Lys Gln
625                 630                 635                 640

Leu Val Glu Asp Leu Asp Arg Ile Leu Thr Leu Thr Thr Asn Glu Glu
                645                 650                 655

Tyr Leu Asp Leu Ser Gln Pro Leu Glu Gln Tyr Ser Pro Ser Tyr Pro
            660                 665                 670

Asp Thr Arg Ser Ser Cys Ser Ser Gly Asp Asp Ser Val Phe Ser Pro
        675                 680                 685

Asp Pro Met Pro Tyr Glu Pro Cys Leu Pro Gln Tyr Pro His Ile Asn
    690                 695                 700

Gly Ser Val Lys Thr
705
```

<210> SEQ ID NO 48
<211> LENGTH: 2124
<212> TYPE: DNA
<213> ORGANISM: Homo sapiens

<400> SEQUENCE: 48

```
atggtcagct ggggtcgttt catctgcctg gtcgtggtca ccatggcaac cttgtccctg     60
gcccggccct ccttcagttt agttgaggat accacattag agccagaagg agcaccatac    120
tggaccaaca cagaaaagat ggaaaagcgg ctccatgctg tgcctgcggc caacactgtc    180
aagtttcgct gcccagccgg ggggaaccca atgccaacca tgcggtggct gaaaaacggg    240
aaggagttta agcaggagca tcgcattgga ggctacaagg tacgaaacca gcactggagc    300
ctcattatgg aaagtgtggt cccatctgac aagggaaatt atacctgtgt agtggagaat    360
gaatacgggt ccatcaatca cacgtaccac ctggatgttg tggagcgatc gcctcaccgg    420
cccatcctcc aagccggact gccggcaaat gcctccacag tggtcggagg agacgtagag    480
tttgtctgca aggtttacag tgatgcccag ccccacatcc agtggatcaa gcacgtggaa    540
aagaacggca gtaaatacgg gcccgacggg ctgccctacc tcaaggttct caagcactcg    600
gggataaata gttccaatgc agaagtgctg gctctgttca atgtgaccga ggcggatgct    660
ggggaatata tatgtaaggt ctccaattat atagggcagg ccaaccagtc tgcctggctc    720
actgtcctgc caaaacagca agcgcctgga agagaaaagg agattacagc ttccccagac    780
tacctggaga tagccattta ctgcataggg gtcttcttaa tcgcctgtat ggtggtaaca    840
gtcatcctgt gccgaatgaa gaacacgacc aagaagccag acttcagcag ccagccggct    900
gtgcacaagc tgaccaaacg tatccccctg cggagacagg taacagtttc ggctgagtcc    960
agctcctcca tgaactccaa caccccgctg gtgaggataa caacacgcct ctcttcaacg   1020
gcagacaccc ccatgctggc aggggtctcc gagtatgaac ttccagagga cccaaaatgg   1080
gagtttccaa gagataagct gacactgggc aagcccctgg gagaaggttg ctttgggcaa   1140
gtggtcatgg cggaagcagt gggaattgac aaagacaagc ccaaggaggc ggtcaccgtg   1200
gccgtgaaga tgttgaaaga tgatgccaca gagaaagacc tttctgatct ggtgtcagag   1260
atggagatga tgaagatgat tgggaaacac aagaatatca taaatcttct tggagcctgc   1320
acacaggatg ggcctctcta tgtcatagtt gagtatgcct ctaaaggcaa cctccgagaa   1380
tacctccgag cccggaggcc acccgggatg gagtactcct atgacattaa ccgtgttcct   1440
gaggagcaga tgaccttcaa ggacttggtg tcatgcacct accagctggc cagaggcatg   1500
gagtacttgg cttcccaaaa atgtattcat cgagatttag cagccagaaa tgttttggta   1560
acagaaaaca atgtgatgaa aatagcagac tttggactcg ccagagatat caacaatata   1620
gactattaca aaaagaccac caatgggcgg cttccagtca agtggatggc tccagaagcc   1680
ctgtttgata gagtatacac tcatcagagt gatgtctggt ccttcggggt gttaatgtgg   1740
gagatcttca ctttaggggg ctcgccctac ccagggattc ccgtggagga actttttaag   1800
ctgctgaagg aaggacacag aatggataag ccagccaact gcaccaacga actgtacatg   1860
atgatgaggg actgttggca tgcagtgccc tcccagagac caacgttcaa gcagttggta   1920
gaagacttgg atcgaattct cactctcaca accaatgagg aatacttgga cctcagccaa   1980
cctctcgaac agtattcacc tagttaccct gacacaagaa gttcttgttc ttcaggagat   2040
gattctgttt tttctccaga ccccatgcct tacgaaccat gccttcctca gtatccacac   2100
```

ataaacggca gtgttaaaac atga 2124

<210> SEQ ID NO 49
<211> LENGTH: 707
<212> TYPE: PRT
<213> ORGANISM: Homo sapiens

<400> SEQUENCE: 49

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys His Ser Gly Ile Asn Ser Ser Asn Ala Glu
        195                 200                 205

Val Leu Ala Leu Phe Asn Val Thr Glu Ala Asp Ala Gly Glu Tyr Ile
    210                 215                 220

Cys Lys Val Ser Asn Tyr Ile Gly Gln Ala Asn Gln Ser Ala Trp Leu
225                 230                 235                 240

Thr Val Leu Pro Lys Gln Gln Ala Pro Gly Arg Glu Lys Glu Ile Thr
                245                 250                 255

Ala Ser Pro Asp Tyr Leu Glu Ile Ala Ile Tyr Cys Ile Gly Val Phe
            260                 265                 270

Leu Ile Ala Cys Met Val Val Thr Val Ile Leu Cys Arg Met Lys Asn
        275                 280                 285

Thr Thr Lys Lys Pro Asp Phe Ser Ser Gln Pro Ala Val His Lys Leu
    290                 295                 300

Thr Lys Arg Ile Pro Leu Arg Arg Gln Val Thr Val Ser Ala Glu Ser
305                 310                 315                 320

Ser Ser Ser Met Asn Ser Asn Thr Pro Leu Val Arg Ile Thr Thr Arg
                325                 330                 335

Leu Ser Ser Thr Ala Asp Thr Pro Met Leu Ala Gly Val Ser Glu Tyr
            340                 345                 350

Glu Leu Pro Glu Asp Pro Lys Trp Glu Phe Pro Arg Asp Lys Leu Thr
        355                 360                 365
```

```
Leu Gly Lys Pro Leu Gly Glu Gly Cys Phe Gly Gln Val Val Met Ala
    370                 375                 380

Glu Ala Val Gly Ile Asp Lys Asp Lys Pro Lys Glu Ala Val Thr Val
385                 390                 395                 400

Ala Val Lys Met Leu Lys Asp Asp Ala Thr Glu Lys Asp Leu Ser Asp
                405                 410                 415

Leu Val Ser Glu Met Glu Met Met Lys Met Ile Gly Lys His Lys Asn
            420                 425                 430

Ile Ile Asn Leu Leu Gly Ala Cys Thr Gln Asp Gly Pro Leu Tyr Val
        435                 440                 445

Ile Val Glu Tyr Ala Ser Lys Gly Asn Leu Arg Glu Tyr Leu Arg Ala
    450                 455                 460

Arg Arg Pro Pro Gly Met Glu Tyr Ser Tyr Asp Ile Asn Arg Val Pro
465                 470                 475                 480

Glu Glu Gln Met Thr Phe Lys Asp Leu Val Ser Cys Thr Tyr Gln Leu
                485                 490                 495

Ala Arg Gly Met Glu Tyr Leu Ala Ser Gln Lys Cys Ile His Arg Asp
            500                 505                 510

Leu Ala Ala Arg Asn Val Leu Val Thr Glu Asn Asn Val Met Lys Ile
        515                 520                 525

Ala Asp Phe Gly Leu Ala Arg Asp Ile Asn Asn Ile Asp Tyr Tyr Lys
    530                 535                 540

Lys Thr Thr Asn Gly Arg Leu Pro Val Lys Trp Met Ala Pro Glu Ala
545                 550                 555                 560

Leu Phe Asp Arg Val Tyr Thr His Gln Ser Asp Val Trp Ser Phe Gly
                565                 570                 575

Val Leu Met Trp Glu Ile Phe Thr Leu Gly Gly Ser Pro Tyr Pro Gly
            580                 585                 590

Ile Pro Val Glu Glu Leu Phe Lys Leu Leu Lys Glu Gly His Arg Met
        595                 600                 605

Asp Lys Pro Ala Asn Cys Thr Asn Glu Leu Tyr Met Met Met Arg Asp
    610                 615                 620

Cys Trp His Ala Val Pro Ser Gln Arg Pro Thr Phe Lys Gln Leu Val
625                 630                 635                 640

Glu Asp Leu Asp Arg Ile Leu Thr Leu Thr Thr Asn Glu Glu Tyr Leu
                645                 650                 655

Asp Leu Ser Gln Pro Leu Glu Gln Tyr Ser Pro Ser Tyr Pro Asp Thr
            660                 665                 670

Arg Ser Ser Cys Ser Ser Gly Asp Asp Ser Val Phe Ser Pro Asp Pro
        675                 680                 685

Met Pro Tyr Glu Pro Cys Leu Pro Gln Tyr Pro His Ile Asn Gly Ser
    690                 695                 700

Val Lys Thr
705
```

<210> SEQ ID NO 50
<211> LENGTH: 2118
<212> TYPE: DNA
<213> ORGANISM: Homo sapiens

<400> SEQUENCE: 50

```
atggtcagct ggggtcgttt catctgcctg gtcgtggtca ccatggcaac cttgtccctg      60

gcccggccct ccttcagttt agttgaggat accacattag agccagaaga gccaccaacc     120

aaataccaaa tctctcaacc agaagtgtac gtggctgcgc caggggagtc gctagaggtg     180
```

```
cgctgcctgt tgaaagatgc cgccgtgatc agttggacta aggatggggt gcacttgggg    240
cccaacaata ggacagtgct tattggggag tacttgcaga taaagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg tttcggctga gtccagctcc    960
tccatgaact ccaacacccc gctggtgagg ataacaacac gcctctcttc aacggcagac   1020
acccccatgc tggcaggggt ctccgagtat gaacttccag aggacccaaa atgggagttt   1080
ccaagagata agctgacact gggcaagccc ctgggagaag gttgctttgg gcaagtggtc   1140
atggcggaag cagtgggaat tgacaaagac aagcccaagg aggcggtcac cgtggccgtg   1200
aagatgttga aagatgatgc cacagagaaa gacctttctg atctggtgtc agagatggag   1260
atgatgaaga tgattgggaa acacaagaat atcataaatc ttcttggagc ctgcacacag   1320
gatgggcctc tctatgtcat agttgagtat gcctctaaag gcaacctccg agaatacctc   1380
cgagcccgga ggccacccgg gatggagtac tcctatgaca ttaaccgtgt tcctgaggag   1440
cagatgacct tcaaggactt ggtgtcatgc acctaccagc tggccagagg catggagtac   1500
ttggcttccc aaaaatgtat tcatcgagat ttagcagcca gaaatgtttt ggtaacagaa   1560
aacaatgtga tgaaaatagc agactttgga ctcgccagag atatcaacaa tatagactat   1620
tacaaaaaga ccaccaatgg gcggcttcca gtcaagtgga tggctccaga agccctgttt   1680
gatagagtat acactcatca gagtgatgtc tggtccttcg gggtgttaat gtgggagatc   1740
ttcactttag gggctcgccc ctacccaggg attcccgtgg aggaactttt taagctgctg   1800
aaggaaggac acagaatgga taagccagcc aactgcacca acgaactgta catgatgatg   1860
agggactgtt ggcatgcagt gccctcccag agaccaacgt tcaagcagtt ggtagaagac   1920
ttggatcgaa ttctcactct cacaaccaat gaggaatact tggacctcag ccaacctctc   1980
gaacagtatt cacctagtta ccctgacaca agaagttctt gttcttcagg agatgattct   2040
gttttttctc cagaccccat gccttacgaa ccatgccttc ctcagtatcc acacataaac   2100
ggcagtgtta aaacatga                                                  2118
```

<210> SEQ ID NO 51
<211> LENGTH: 705
<212> TYPE: PRT
<213> ORGANISM: Homo sapiens

<400> SEQUENCE: 51

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
```

```
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Ser Ala Glu Ser Ser Ser
305                 310                 315                 320

Ser Met Asn Ser Asn Thr Pro Leu Val Arg Ile Thr Thr Arg Leu Ser
                325                 330                 335

Ser Thr Ala Asp Thr Pro Met Leu Ala Gly Val Ser Glu Tyr Glu Leu
            340                 345                 350

Pro Glu Asp Pro Lys Trp Glu Phe Pro Arg Asp Lys Leu Thr Leu Gly
        355                 360                 365

Lys Pro Leu Gly Glu Gly Cys Phe Gly Gln Val Val Met Ala Glu Ala
    370                 375                 380

Val Gly Ile Asp Lys Asp Lys Pro Lys Glu Ala Val Thr Val Ala Val
385                 390                 395                 400

Lys Met Leu Lys Asp Asp Ala Thr Glu Lys Asp Leu Ser Asp Leu Val
                405                 410                 415

Ser Glu Met Glu Met Met Lys Met Ile Gly Lys His Lys Asn Ile Ile
            420                 425                 430

Asn Leu Leu Gly Ala Cys Thr Gln Asp Gly Pro Leu Tyr Val Ile Val
        435                 440                 445
```

```
Glu Tyr Ala Ser Lys Gly Asn Leu Arg Glu Tyr Leu Arg Ala Arg Arg
    450                 455                 460

Pro Pro Gly Met Glu Tyr Ser Tyr Asp Ile Asn Arg Val Pro Glu Glu
465                 470                 475                 480

Gln Met Thr Phe Lys Asp Leu Val Ser Cys Thr Tyr Gln Leu Ala Arg
                485                 490                 495

Gly Met Glu Tyr Leu Ala Ser Gln Lys Cys Ile His Arg Asp Leu Ala
            500                 505                 510

Ala Arg Asn Val Leu Val Thr Glu Asn Asn Val Met Lys Ile Ala Asp
        515                 520                 525

Phe Gly Leu Ala Arg Asp Ile Asn Asn Ile Asp Tyr Tyr Lys Lys Thr
    530                 535                 540

Thr Asn Gly Arg Leu Pro Val Lys Trp Met Ala Pro Glu Ala Leu Phe
545                 550                 555                 560

Asp Arg Val Tyr Thr His Gln Ser Asp Val Trp Ser Phe Gly Val Leu
                565                 570                 575

Met Trp Glu Ile Phe Thr Leu Gly Gly Ser Pro Tyr Pro Gly Ile Pro
            580                 585                 590

Val Glu Glu Leu Phe Lys Leu Leu Lys Glu Gly His Arg Met Asp Lys
        595                 600                 605

Pro Ala Asn Cys Thr Asn Glu Leu Tyr Met Met Met Arg Asp Cys Trp
    610                 615                 620

His Ala Val Pro Ser Gln Arg Pro Thr Phe Lys Gln Leu Val Glu Asp
625                 630                 635                 640

Leu Asp Arg Ile Leu Thr Leu Thr Thr Asn Glu Glu Tyr Leu Asp Leu
                645                 650                 655

Ser Gln Pro Leu Glu Gln Tyr Ser Pro Ser Tyr Pro Asp Thr Arg Ser
            660                 665                 670

Ser Cys Ser Ser Gly Asp Asp Ser Val Phe Ser Pro Asp Pro Met Pro
        675                 680                 685

Tyr Glu Pro Cys Leu Pro Gln Tyr Pro His Ile Asn Gly Ser Val Lys
    690                 695                 700

Thr
705
```

<210> SEQ ID NO 52
<211> LENGTH: 2115
<212> TYPE: DNA
<213> ORGANISM: Homo sapiens

<400> SEQUENCE: 52

```
atggtcagct ggggtcgttt catctgcctg gtcgtggtca ccatggcaac cttgtccctg      60

gcccggccct ccttcagttt agttgaggat accacattag agccagaagg agcaccatac     120

tggaccaaca cagaaaagat ggaaaagcgg ctccatgctg tgcctgcggc caacactgtc     180

aagtttcgct gcccagccgg ggggaaccca atgccaacca tgcggtggct gaaaaacggg     240

aaggagttta agcaggagca tcgcattgga ggctacaagg tacgaaacca gcactggagc     300

ctcattatgg aaagtgtggt cccatctgac aagggaaatt atacctgtgt agtggagaat     360

gaatacgggt ccatcaatca cacgtaccac ctggatgttg tggagcgatc gcctcaccgg     420

cccatcctcc aagccggact gccggcaaat gcctccacag tggtcggagg agacgtagag     480

tttgtctgca aggtttacag tgatgcccag ccccacatcc agtggatcaa gcacgtggaa     540

aagaacggca gtaaatacgg gcccgacggg ctgccctacc tcaaggttct caaggccgcc     600
```

```
ggtgttaaca ccacggacaa agagattgag gttctctata ttcggaatgt aacttttgag    660

gacgctgggg aatatacgtg cttggcgggt aattctattg ggatatcctt tcactctgca    720

tggttgacag ttctgccagc gcctggaaga gaaaaggaga ttacagcttc cccagactac    780

ctggagatag ccatttactg catagggtc ttcttaatcg cctgtatggt ggtaacagtc    840

atcctgtgcc gaatgaagaa cacgaccaag aagccagact tcagcagcca gccggctgtg    900

cacaagctga ccaaacgtat cccccctgcgg agacaggttt cggctgagtc cagctcctcc    960

atgaactcca acaccccgct ggtgaggata acaacacgcc tctcttcaac ggcagacacc   1020

cccatgctgg caggggtctc cgagtatgaa cttccagagg acccaaaatg ggagtttcca   1080

agagataagc tgacactggg caagcccctg ggagaaggtt gctttgggca agtggtcatg   1140

gcggaagcag tgggaattga caaagacaag cccaaggagg cggtcaccgt ggccgtgaag   1200

atgttgaaag atgatgccac agagaaagac ctttctgatc tggtgtcaga gatggagatg   1260

atgaagatga ttgggaaaca caagaatatc ataaatcttc ttggagcctg cacacaggat   1320

gggcctctct atgtcatagt tgagtatgcc tctaaaggca acctccgaga atacctccga   1380

gcccggaggc cacccgggat ggagtactcc tatgacatta accgtgttcc tgaggagcag   1440

atgaccttca aggacttggt gtcatgcacc taccagctgg ccagaggcat ggagtacttg   1500

gcttcccaaa aatgtattca tcgagattta gcagccagaa atgttttggt aacagaaaac   1560

aatgtgatga aaatagcaga ctttggactc gccagagata tcaacaatat agactattac   1620

aaaaagacca ccaatgggcg gcttccagtc aagtggatgg ctccagaagc cctgtttgat   1680

agagtataca ctcatcagag tgatgtctgg tccttcgggg tgttaatgtg ggagatcttc   1740

actttagggg gctcgcccta cccagggatt cccgtggagg aactttttaa gctgctgaag   1800

gaaggacaca gaatggataa gccagccaac tgcaccaacg aactgtacat gatgatgagg   1860

gactgttggc atgcagtgcc ctcccagaga ccaacgttca agcagttggt agaagacttg   1920

gatcgaattc tcactctcac aaccaatgag gaatacttgg acctcagcca acctctcgaa   1980

cagtattcac ctagttaccc tgacacaaga agttcttgtt cttcaggaga tgattctgtt   2040

ttttctccag accccatgcc ttacgaacca tgccttcctc agtatccaca cataaacggc   2100

agtgttaaaa catga                                                    2115
```

```
<210> SEQ ID NO 53
<211> LENGTH: 704
<212> TYPE: PRT
<213> ORGANISM: Homo sapiens

<400> SEQUENCE: 53

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95
```

```
Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
            260                 265                 270

Ile Ala Cys Met Val Val Thr Val Ile Leu Cys Arg Met Lys Asn Thr
        275                 280                 285

Thr Lys Lys Pro Asp Phe Ser Ser Gln Pro Ala Val His Lys Leu Thr
    290                 295                 300

Lys Arg Ile Pro Leu Arg Arg Gln Val Ser Ala Glu Ser Ser Ser Ser
305                 310                 315                 320

Met Asn Ser Asn Thr Pro Leu Val Arg Ile Thr Thr Arg Leu Ser Ser
                325                 330                 335

Thr Ala Asp Thr Pro Met Leu Ala Gly Val Ser Glu Tyr Glu Leu Pro
            340                 345                 350

Glu Asp Pro Lys Trp Glu Phe Pro Arg Asp Lys Leu Thr Leu Gly Lys
        355                 360                 365

Pro Leu Gly Glu Gly Cys Phe Gly Gln Val Val Met Ala Glu Ala Val
    370                 375                 380

Gly Ile Asp Lys Asp Lys Pro Lys Glu Ala Val Thr Val Ala Val Lys
385                 390                 395                 400

Met Leu Lys Asp Asp Ala Thr Glu Lys Asp Leu Ser Asp Leu Val Ser
                405                 410                 415

Glu Met Glu Met Met Lys Met Ile Gly Lys His Lys Asn Ile Ile Asn
            420                 425                 430

Leu Leu Gly Ala Cys Thr Gln Asp Gly Pro Leu Tyr Val Ile Val Glu
        435                 440                 445

Tyr Ala Ser Lys Gly Asn Leu Arg Glu Tyr Leu Arg Ala Arg Arg Pro
    450                 455                 460

Pro Gly Met Glu Tyr Ser Tyr Asp Ile Asn Arg Val Pro Glu Glu Gln
465                 470                 475                 480

Met Thr Phe Lys Asp Leu Val Ser Cys Thr Tyr Gln Leu Ala Arg Gly
                485                 490                 495

Met Glu Tyr Leu Ala Ser Gln Lys Cys Ile His Arg Asp Leu Ala Ala
            500                 505                 510

Arg Asn Val Leu Val Thr Glu Asn Asn Val Met Lys Ile Ala Asp Phe
```

```
        515                 520                 525

Gly Leu Ala Arg Asp Ile Asn Asn Ile Asp Tyr Tyr Lys Lys Thr Thr
    530                 535                 540

Asn Gly Arg Leu Pro Val Lys Trp Met Ala Pro Glu Ala Leu Phe Asp
545                 550                 555                 560

Arg Val Tyr Thr His Gln Ser Asp Val Trp Ser Phe Gly Val Leu Met
                565                 570                 575

Trp Glu Ile Phe Thr Leu Gly Gly Ser Pro Tyr Pro Gly Ile Pro Val
            580                 585                 590

Glu Glu Leu Phe Lys Leu Leu Lys Glu Gly His Arg Met Asp Lys Pro
        595                 600                 605

Ala Asn Cys Thr Asn Glu Leu Tyr Met Met Met Arg Asp Cys Trp His
    610                 615                 620

Ala Val Pro Ser Gln Arg Pro Thr Phe Lys Gln Leu Val Glu Asp Leu
625                 630                 635                 640

Asp Arg Ile Leu Thr Leu Thr Thr Asn Glu Glu Tyr Leu Asp Leu Ser
                645                 650                 655

Gln Pro Leu Glu Gln Tyr Ser Pro Ser Tyr Pro Asp Thr Arg Ser Ser
            660                 665                 670

Cys Ser Ser Gly Asp Asp Ser Val Phe Ser Pro Asp Pro Met Pro Tyr
        675                 680                 685

Glu Pro Cys Leu Pro Gln Tyr Pro His Ile Asn Gly Ser Val Lys Thr
    690                 695                 700


<210> SEQ ID NO 54
<211> LENGTH: 2008
<212> TYPE: DNA
<213> ORGANISM: Homo sapiens

<400> SEQUENCE: 54

atggtcagct ggggtcgttt catctgcctg gtcgtggtca ccatggcaac cttgtccctg      60

gcccggccct ccttcagttt agttgaggat accacattag agccagaaga tgccatctca     120

tccggagatg atgaggatga caccgatggt gcggaagatt ttgtcagtga gaacagtaac     180

aacaagagag caccatactg gaccaacaca gaaaagatgg aaaagcggct ccatgctgtg     240

cctgcggcca acactgtcaa gtttcgctgc ccagccgggg ggaacccaat gccaaccatg     300

cggtggctga aaaacgggaa ggagtttaag caggagcatc gcattggagg ctacaaggta     360

cgaaaccagc actggagcct cattatggaa agtgtggtcc catctgacaa gggaaattat     420

acctgtgtag tggagaatga atacgggtcc atcaatcaca cgtaccacct ggatgttgtg     480

gagcgatcgc ctcaccggcc catcctccaa gccggactgc cggcaaatgc ctccacagtg     540

gtcggaggag acgtagagtt tgtctgcaag gtttacagtg atgcccagcc ccacatccag     600

tggatcaagc acgtggaaaa gaacggcagt aaatacgggc ccgacgggct gccctacctc     660

aaggttctca aggccgccgg tgttaacacc acggacaaag agattgaggt tctctatatt     720

cggaatgtaa cttttgagga cgctggggaa tatacgtgct tggcgggtaa ttctattggg     780

atatcctttc actctgcatg gttgacagtt ctgccagcgc ctggaagaga aaaggagatt     840

acagcttccc cagactacct ggagatagcc atttactgca taggggtctt cttaatcgcc     900

tgtatggtgg taacagtcat cctgtgccga atgaagaaca cgaccaagaa gccagacttc     960

agcagccagc cggctgtgca caagctgacc aaacgtatcc ccctgcggag acaggtttcg    1020

gctgagtcca gctcctccat gaactccaac accccgctgg tgaggataac aacacgcctc    1080
```

```
tcttcaacgg cagacacccc catgctggca ggggtctccg agtatgaact tccagaggac   1140

ccaaaatggg agtttccaag agataagctg acactgggca agcccctggg agaaggttgc   1200

tttgggcaag tggtcatggc ggaagcagtg ggaattgaca aagacaagcc caaggaggcg   1260

gtcaccgtgg ccgtgaagat gttgaaagat gatgccacag agaaagacct ttctgatctg   1320

gtgtcagaga tggagatgat gaagatgatt gggaaacaca agaatatcat aaatcttctt   1380

ggagcctgca cacaggatgg gcctctctat gtcatagttg agtatgcctc taaaggcaac   1440

ctccgagaat acctccgagc ccggaggcca cccgggatgg agtactccta tgacattaac   1500

cgtgttcctg aggagcagat gaccttcaag gacttggtgt catgcaccta ccagctggcc   1560

agaggcatgg agtacttggc ttcccaaaaa tgtattcatc gagatttagc agccagaaat   1620

gttttggtaa cagaaaacaa tgtgatgaaa atagcagact ttggactcgc cagagatatc   1680

aacaatatag actattacaa aaagaccacc aatgggcggc ttccagtcaa gtggatggct   1740

ccagaagccc tgtttgatag agtatacact catcagagtg atgtctggtc cttcggggtg   1800

ttaatgtggg agatcttcac tttagggggc tcgccctacc cagggattcc cgtggaggaa   1860

ctttttaagc tgctgaagga aggacacaga atggataagc cagccaactg caccaacgaa   1920

ctgtacatga tgatgaggga ctgttggcat gcagtgccct cccagagacc aacgttcaag   1980

cagttggtag aagacttgga tcgaattc                                       2008
```

```
<210> SEQ ID NO 55
<211> LENGTH: 669
<212> TYPE: PRT
<213> ORGANISM: Homo sapiens

<400> SEQUENCE: 55

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205
```

```
Gly Ser Lys Tyr Gly Pro Asp Gly Leu Pro Tyr Leu Lys Val Leu Lys
    210                 215                 220

Ala Ala Gly Val Asn Thr Thr Asp Lys Glu Ile Glu Val Leu Tyr Ile
225                 230                 235                 240

Arg Asn Val Thr Phe Glu Asp Ala Gly Glu Tyr Thr Cys Leu Ala Gly
                245                 250                 255

Asn Ser Ile Gly Ile Ser Phe His Ser Ala Trp Leu Thr Val Leu Pro
            260                 265                 270

Ala Pro Gly Arg Glu Lys Glu Ile Thr Ala Ser Pro Asp Tyr Leu Glu
        275                 280                 285

Ile Ala Ile Tyr Cys Ile Gly Val Phe Leu Ile Ala Cys Met Val Val
    290                 295                 300

Thr Val Ile Leu Cys Arg Met Lys Asn Thr Thr Lys Lys Pro Asp Phe
305                 310                 315                 320

Ser Ser Gln Pro Ala Val His Lys Leu Thr Lys Arg Ile Pro Leu Arg
                325                 330                 335

Arg Gln Val Ser Ala Glu Ser Ser Ser Ser Met Asn Ser Asn Thr Pro
            340                 345                 350

Leu Val Arg Ile Thr Thr Arg Leu Ser Ser Thr Ala Asp Thr Pro Met
        355                 360                 365

Leu Ala Gly Val Ser Glu Tyr Glu Leu Pro Glu Asp Pro Lys Trp Glu
    370                 375                 380

Phe Pro Arg Asp Lys Leu Thr Leu Gly Lys Pro Leu Gly Glu Gly Cys
385                 390                 395                 400

Phe Gly Gln Val Val Met Ala Glu Ala Val Gly Ile Asp Lys Asp Lys
                405                 410                 415

Pro Lys Glu Ala Val Thr Val Ala Val Lys Met Leu Lys Asp Asp Ala
            420                 425                 430

Thr Glu Lys Asp Leu Ser Asp Leu Val Ser Glu Met Glu Met Met Lys
        435                 440                 445

Met Ile Gly Lys His Lys Asn Ile Ile Asn Leu Leu Gly Ala Cys Thr
    450                 455                 460

Gln Asp Gly Pro Leu Tyr Val Ile Val Glu Tyr Ala Ser Lys Gly Asn
465                 470                 475                 480

Leu Arg Glu Tyr Leu Arg Ala Arg Arg Pro Pro Gly Met Glu Tyr Ser
                485                 490                 495

Tyr Asp Ile Asn Arg Val Pro Glu Glu Gln Met Thr Phe Lys Asp Leu
            500                 505                 510

Val Ser Cys Thr Tyr Gln Leu Ala Arg Gly Met Glu Tyr Leu Ala Ser
        515                 520                 525

Gln Lys Cys Ile His Arg Asp Leu Ala Ala Arg Asn Val Leu Val Thr
    530                 535                 540

Glu Asn Asn Val Met Lys Ile Ala Asp Phe Gly Leu Ala Arg Asp Ile
545                 550                 555                 560

Asn Asn Ile Asp Tyr Tyr Lys Lys Thr Thr Asn Gly Arg Leu Pro Val
                565                 570                 575

Lys Trp Met Ala Pro Glu Ala Leu Phe Asp Arg Val Tyr Thr His Gln
            580                 585                 590

Ser Asp Val Trp Ser Phe Gly Val Leu Met Trp Glu Ile Phe Thr Leu
        595                 600                 605

Gly Gly Ser Pro Tyr Pro Gly Ile Pro Val Glu Glu Leu Phe Lys Leu
    610                 615                 620

Leu Lys Glu Gly His Arg Met Asp Lys Pro Ala Asn Cys Thr Asn Glu
```

625 630 635 640

Leu Tyr Met Met Met Arg Asp Cys Trp His Ala Val Pro Ser Gln Arg
645 650 655

Pro Thr Phe Lys Gln Leu Val Glu Asp Leu Asp Arg Ile
660 665

<210> SEQ ID NO 56
<211> LENGTH: 1782
<212> TYPE: DNA
<213> ORGANISM: Homo sapiens

<400> SEQUENCE: 56
atgtgtttaa acaaaaacaa acagctcttt ggcgttgcta agagactgcc attttggagg 60
aaagagcgat cgcctcaccg gcccatcctc caagccggac tgccggcaaa tgcctccaca 120
gtggtcggag gagacgtaga gtttgtctgc aaggtttaca gtgatgccca gccccacatc 180
cagtggatca agcacgtgga aaagaacggc agtaaatacg ggcccgacgg gctgccctac 240
ctcaaggttc tcaaggccgc cggtgttaac accacggaca aagagattga ggttctctat 300
attcggaatg taacttttga ggacgctggg gaatatacgt gcttggcggg taattctatt 360
gggatatcct ttcactctgc atggttgaca gttctgccag cgcctggaag agaaaaggag 420
attacagctt ccccagacta cctggagata gccatttact gcataggggt cttcttaatc 480
gcctgtatgg tggtaacagt catcctgtgc cgaatgaaga acacgaccaa gaagccagac 540
ttcagcagcc agccggctgt gcacaagctg accaaacgta tcccccctgcg gagacaggta 600 acagtttcgg ctgagtccag ctcctccatg aactccaaca ccccgctggt gaggataaca 660
acacgcctct cttcaacggc agacaccccc atgctggcag gggtctccga gtatgaactt 720
ccagaggacc caaaatggga gtttccaaga gataagctga cactgggcaa gcccctggga 780
gaaggttgct ttgggcaagt ggtcatggcg gaagcagtgg gaattgacaa agacaagccc 840
aaggaggcgg tcaccgtggc cgtgaagatg ttgaaagatg atgccacaga gaaagacctt 900
tctgatctgg tgtcagagat ggagatgatg aagatgattg ggaaacacaa gaatatcata 960
aatcttcttg gagcctgcac acaggatggg cctctctatg tcatagttga gtatgcctct 1020
aaaggcaacc tccgagaata cctccgagcc cggaggccac ccgggatgga gtactcctat 1080
gacattaacc gtgttcctga ggagcagatg accttcaagg acttggtgtc atgcacctac 1140
cagctggcca gaggcatgga gtacttggct tcccaaaaat gtattcatcg agatttagca 1200
gccagaaatg ttttggtaac agaaaacaat gtgatgaaaa tagcagactt tggactcgcc 1260
agagatatca acaatataga ctattacaaa aagaccacca atgggcggct tccagtcaag 1320
tggatggctc cagaagccct gtttgataga gtatacactc atcagagtga tgtctggtcc 1380
ttcggggtgt taatgtggga gatcttcact ttagggggct cgccctaccc agggattccc 1440
gtggaggaac tttttaagct gctgaaggaa ggacacagaa tggataagcc agccaactgc 1500
accaacgaac tgtacatgat gatgagggac tgttggcatg cagtgccctc ccagagacca 1560
acgttcaagc agttggtaga agacttggat cgaattctca ctctcacaac caatgaggaa 1620
tacttggacc tcagccaacc tctcgaacag tattcaccta gttaccctga cacaagaagt 1680
tcttgttctt caggagatga ttctgttttt tctccagacc ccatgcctta cgaaccatgc 1740
cttcctcagt atccacacat aaacggcagt gttaaaacat ga 1782

<210> SEQ ID NO 57
<211> LENGTH: 593

```
<212> TYPE: PRT
<213> ORGANISM: Homo sapiens

<400> SEQUENCE: 57

Met Cys Leu Asn Lys Thr Lys Gln Leu Phe Gly Val Ala Lys Arg Leu
1               5                   10                  15

Pro Phe Trp Arg Lys Glu Arg Ser Pro His Arg Pro Ile Leu Gln Ala
            20                  25                  30

Gly Leu Pro Ala Asn Ala Ser Thr Val Val Gly Gly Asp Val Glu Phe
        35                  40                  45

Val Cys Lys Val Tyr Ser Asp Ala Gln Pro His Ile Gln Trp Ile Lys
    50                  55                  60

His Val Glu Lys Asn Gly Ser Lys Tyr Gly Pro Asp Gly Leu Pro Tyr
65                  70                  75                  80

Leu Lys Val Leu Lys Ala Ala Gly Val Asn Thr Thr Asp Lys Glu Ile
                85                  90                  95

Glu Val Leu Tyr Ile Arg Asn Val Thr Phe Glu Asp Ala Gly Glu Tyr
            100                 105                 110

Thr Cys Leu Ala Gly Asn Ser Ile Gly Ile Ser Phe His Ser Ala Trp
        115                 120                 125

Leu Thr Val Leu Pro Ala Pro Gly Arg Glu Lys Glu Ile Thr Ala Ser
    130                 135                 140

Pro Asp Tyr Leu Glu Ile Ala Ile Tyr Cys Ile Gly Val Phe Leu Ile
145                 150                 155                 160

Ala Cys Met Val Val Thr Val Ile Leu Cys Arg Met Lys Asn Thr Thr
                165                 170                 175

Lys Lys Pro Asp Phe Ser Ser Gln Pro Ala Val His Lys Leu Thr Lys
            180                 185                 190

Arg Ile Pro Leu Arg Arg Gln Val Thr Val Ser Ala Glu Ser Ser Ser
        195                 200                 205

Ser Met Asn Ser Asn Thr Pro Leu Val Arg Ile Thr Thr Arg Leu Ser
    210                 215                 220

Ser Thr Ala Asp Thr Pro Met Leu Ala Gly Val Ser Glu Tyr Glu Leu
225                 230                 235                 240

Pro Glu Asp Pro Lys Trp Glu Phe Pro Arg Asp Lys Leu Thr Leu Gly
                245                 250                 255

Lys Pro Leu Gly Glu Gly Cys Phe Gly Gln Val Val Met Ala Glu Ala
            260                 265                 270

Val Gly Ile Asp Lys Asp Lys Pro Lys Glu Ala Val Thr Val Ala Val
        275                 280                 285

Lys Met Leu Lys Asp Asp Ala Thr Glu Lys Asp Leu Ser Asp Leu Val
    290                 295                 300

Ser Glu Met Glu Met Met Lys Met Ile Gly Lys His Lys Asn Ile Ile
305                 310                 315                 320

Asn Leu Leu Gly Ala Cys Thr Gln Asp Gly Pro Leu Tyr Val Ile Val
                325                 330                 335

Glu Tyr Ala Ser Lys Gly Asn Leu Arg Glu Tyr Leu Arg Ala Arg Arg
            340                 345                 350

Pro Pro Gly Met Glu Tyr Ser Tyr Asp Ile Asn Arg Val Pro Glu Glu
        355                 360                 365

Gln Met Thr Phe Lys Asp Leu Val Ser Cys Thr Tyr Gln Leu Ala Arg
    370                 375                 380

Gly Met Glu Tyr Leu Ala Ser Gln Lys Cys Ile His Arg Asp Leu Ala
385                 390                 395                 400
```

```
Ala Arg Asn Val Leu Val Thr Glu Asn Asn Val Met Lys Ile Ala Asp
                405                 410                 415

Phe Gly Leu Ala Arg Asp Ile Asn Asn Ile Asp Tyr Tyr Lys Lys Thr
            420                 425                 430

Thr Asn Gly Arg Leu Pro Val Lys Trp Met Ala Pro Glu Ala Leu Phe
        435                 440                 445

Asp Arg Val Tyr Thr His Gln Ser Asp Val Trp Ser Phe Gly Val Leu
    450                 455                 460

Met Trp Glu Ile Phe Thr Leu Gly Gly Ser Pro Tyr Pro Gly Ile Pro
465                 470                 475                 480

Val Glu Glu Leu Phe Lys Leu Leu Lys Glu Gly His Arg Met Asp Lys
                485                 490                 495

Pro Ala Asn Cys Thr Asn Glu Leu Tyr Met Met Met Arg Asp Cys Trp
            500                 505                 510

His Ala Val Pro Ser Gln Arg Pro Thr Phe Lys Gln Leu Val Glu Asp
        515                 520                 525

Leu Asp Arg Ile Leu Thr Leu Thr Thr Asn Glu Glu Tyr Leu Asp Leu
    530                 535                 540

Ser Gln Pro Leu Glu Gln Tyr Ser Pro Ser Tyr Pro Asp Thr Arg Ser
545                 550                 555                 560

Ser Cys Ser Ser Gly Asp Asp Ser Val Phe Ser Pro Asp Pro Met Pro
                565                 570                 575

Tyr Glu Pro Cys Leu Pro Gln Tyr Pro His Ile Asn Gly Ser Val Lys
            580                 585                 590

Thr


<210> SEQ ID NO 58
<211> LENGTH: 1116
<212> TYPE: DNA
<213> ORGANISM: Homo sapiens

<400> SEQUENCE: 58

ttcagcagcc agccggctgt gcacaagctg accaaacgta tccccctgcg gagacaggta      60

acagtttcgg ctgagtccag ctcctccatg aactccaaca ccccgctggt gaggataaca     120

acacgcctct cttcaacggc agacaccccc atgctggcag gggtctccga gtatgaactt     180

ccagaggacc caaaatggga gtttccaaga gataagctga cactgggcaa gcccctggga     240

gaaggttgct ttgggcaagt ggtcatggcg gaagcagtgg gaattgacaa agacaagccc     300

aaggaggcgg tcaccgtggc cgtgaagatg ttgaaagatg atgccacaga gaaagacctt     360

tctgatctgg tgtcagagat ggagatgatg aagatgattg ggaaacacaa gaatatcata     420

aatcttcttg gagcctgcac acaggatggg cctctctatg tcatagttga gtatgcctct     480

aaaggcaacc tccgagaata cctccgagcc cggaggccac ccgggatgga gtactcctat     540

gacattaacc gtgttcctga ggagcagatg accttcaagg acttggtgtc atgcacctac     600

cagctggcca gaggcatgga gtacttggct tcccaaaaat gtattcatcg agatttagca     660

gccagaaatg ttttggtaac agaaaacaat gtgatgaaaa tagcagactt tggactcgcc     720

agagatatca acaatataga ctattacaaa aagaccacca atgggcggct tccagtcaag     780

tggatggctc cagaagccct gtttgataga gtatacactc atcagagtga tgtctggtcc     840

ttcggggtgt taatgtggga gatcttcact ttagggggct cgccctaccc agggattccc     900

gtggaggaac tttttaagct gctgaaggaa ggacacagaa tggataagcc agccaactgc     960
```

```
accaacgaac tgaatacttg gacctcagcc aacctctcga acagtattca cctagttacc   1020

ctgacacaag aagttcttgt tcttcaggag atgattctgt tttttctcca gaccccatgc   1080

cttacgaacc atgccttcct cagtatccac acataa                             1116


<210> SEQ ID NO 59
<211> LENGTH: 371
<212> TYPE: PRT
<213> ORGANISM: Homo sapiens

<400> SEQUENCE: 59

Phe Ser Ser Gln Pro Ala Val His Lys Leu Thr Lys Arg Ile Pro Leu
1               5                   10                  15

Arg Arg Gln Val Thr Val Ser Ala Glu Ser Ser Ser Ser Met Asn Ser
            20                  25                  30

Asn Thr Pro Leu Val Arg Ile Thr Thr Arg Leu Ser Ser Thr Ala Asp
        35                  40                  45

Thr Pro Met Leu Ala Gly Val Ser Glu Tyr Glu Leu Pro Glu Asp Pro
    50                  55                  60

Lys Trp Glu Phe Pro Arg Asp Lys Leu Thr Leu Gly Lys Pro Leu Gly
65                  70                  75                  80

Glu Gly Cys Phe Gly Gln Val Val Met Ala Glu Ala Val Gly Ile Asp
                85                  90                  95

Lys Asp Lys Pro Lys Glu Ala Val Thr Val Ala Val Lys Met Leu Lys
            100                 105                 110

Asp Asp Ala Thr Glu Lys Asp Leu Ser Asp Leu Val Ser Glu Met Glu
        115                 120                 125

Met Met Lys Met Ile Gly Lys His Lys Asn Ile Ile Asn Leu Leu Gly
    130                 135                 140

Ala Cys Thr Gln Asp Gly Pro Leu Tyr Val Ile Val Glu Tyr Ala Ser
145                 150                 155                 160

Lys Gly Asn Leu Arg Glu Tyr Leu Arg Ala Arg Arg Pro Pro Gly Met
                165                 170                 175

Glu Tyr Ser Tyr Asp Ile Asn Arg Val Pro Glu Glu Gln Met Thr Phe
            180                 185                 190

Lys Asp Leu Val Ser Cys Thr Tyr Gln Leu Ala Arg Gly Met Glu Tyr
        195                 200                 205

Leu Ala Ser Gln Lys Cys Ile His Arg Asp Leu Ala Ala Arg Asn Val
    210                 215                 220

Leu Val Thr Glu Asn Asn Val Met Lys Ile Ala Asp Phe Gly Leu Ala
225                 230                 235                 240

Arg Asp Ile Asn Asn Ile Asp Tyr Tyr Lys Lys Thr Thr Asn Gly Arg
                245                 250                 255

Leu Pro Val Lys Trp Met Ala Pro Glu Ala Leu Phe Asp Arg Val Tyr
            260                 265                 270

Thr His Gln Ser Asp Val Trp Ser Phe Gly Val Leu Met Trp Glu Ile
        275                 280                 285

Phe Thr Leu Gly Gly Ser Pro Tyr Pro Gly Ile Pro Val Glu Glu Leu
    290                 295                 300

Phe Lys Leu Leu Lys Glu Gly His Arg Met Asp Lys Pro Ala Asn Cys
305                 310                 315                 320

Thr Asn Glu Leu Asn Thr Trp Thr Ser Ala Asn Leu Ser Asn Ser Ile
                325                 330                 335

His Leu Val Thr Leu Thr Gln Glu Val Leu Val Leu Gln Glu Met Ile
            340                 345                 350
```

```
Leu Phe Phe Leu Gln Thr Pro Cys Leu Thr Asn His Ala Phe Leu Ser
        355                 360                 365

Ile His Thr
    370


<210> SEQ ID NO 60
<211> LENGTH: 2421
<212> TYPE: DNA
<213> ORGANISM: Homo sapiens
<220> FEATURE:
<221> NAME/KEY: variation
<222> LOCATION: (1404)..(1404)
<223> OTHER INFORMATION: R = A or G (dbSNP entry rs767809)
<220> FEATURE:
<221> NAME/KEY: variation
<222> LOCATION: (1830)..(1830)
<223> OTHER INFORMATION: S = C or G (dbSNP entry rs2131956)

<400> SEQUENCE: 60

gggcagatga ctgatcaagt ggctgacctc cgtgccagag gacaaggatc ctcaccggtg     60

gccatgcaga aagctcagca ggtatctcag ggtctggatg tgctcacagc aaaagtggaa    120

aatgcagctc gcaagctgga agccatgacc aactcaaagc agagcattgc aaagaagatc    180

gatgctgctc agaactggct tgcagatcca aatggtggac cggaaggaga agagcagatt    240

cgaggtgctt tggctgaagc tcggaaaata gcagaattat gtgatgatcc taaagaaaga    300

gatgacattc tacgttccct tggggaaata tctgctctga cttctaaatt agcagatcta    360

cgaagacagg ggaaaggaga ttctccagag gctcgagcct tggccaaaca ggtggccacg    420

gccctgcaga acctgcagac caaaaccaac cgggctgtgg ccaacagcag accggccaaa    480

gcagctgtac accttgaggg caagattgag caagcacagc ggtggattga taatcccaca    540

gtggatgacc gtggagtcgg tcaggctgcc atccgggggc ttgtggccga agggcatcgt    600

ctggctaatg ttatgatggg gccttatcgg caagatcttc tcgccaagtg tgaccgagtg    660

gaccagctga cagcccagct ggctgacctg gctgccagag gggaaggggga gagtcctcag   720

gcacgagcac ttgcatctca gctccaagac tccttaaagg atctaaaagc tcggatgcag    780

gaggccatga ctcaggaagt gtcagatgtt ttcagcgata ccacaactcc catcaagctg    840

ttggcagtgg cagccacggc gcctcctgat gcgcctaaca gggaagaggt atttgatgag    900

agggcagcta actttgaaaa ccattcagga aagcttggtg ctacggccga gaaggcggct    960

gcggttggta ctgctaataa atcaacagtg gaaggcattc aggcctcagt gaagacggcc   1020

cgagaactca caccccaggt ggtctcggct gctcgtatct tacttaggaa ccctggaaat   1080

caagctgctt atgaacattt tgagaccatg aagaaccagt ggatcgataa tgttgaaaaa   1140

atgacagggc tggtggacga agccattgat accaaatctc tgttggatgc ttcagaagaa   1200

gcaattaaaa aagacctgga caagtgcaag gtagctatgg ccaacattca gcctcagatg   1260

ctggttgctg ggggcaaccag tattgctcgt cgggccaacc ggatcctgct ggtggctaag  1320

agggaggtgg agaattccga ggatcccaag ttccgtgagg ctgtgaaagc tgcctctgat   1380

gaattgagca aaaccatctc cccratggtg atggatgcaa aagctgtggc tggaaacatt   1440

tccgaccctg gactgcaaaa gagcttcctg gactcaggat atcggatcct gggagctgtg   1500

gccaaggtca gagaagcctt ccaacctcag gagcctgact tcccgccgcc tccaccagac   1560

cttgaacaac tccgactaac agatgagctt gctcctccca aaccacctct gcctgaaggt   1620

gaggtccctc cacctaggcc tccaccacca gaggaaaagg atgaagagtt ccctgagcag   1680
```

```
aaggccgggg aggtgattaa ccagccaatg atgatggctg ccagacagct ccatgatgaa   1740

gctcgcaaat ggtccagcaa gccgggcatc ccagccgctg aggtgggtat aggtgttgta   1800

gctgaggcag atgcggccga tgctgctggs ttccctgtcc cccctgacat ggaagacgat   1860

tacgaacctg agctgctgtt aatgccatcc aatcagccgg tcaaccagcc cattctggcc   1920

gcggctcagt ccttgcatcg ggaagctacc aagtggtcta gtaagggcaa tgacatcatt   1980

gcagcagcca agcgcatggc tctgctgatg gctgagatgt ctcggctggt aagagggggc   2040

agtggtacca agcgggcact cattcagtgt gccaaggaca tcgccaaggc ctcagatgag   2100

gtgactcggt tggccaagga ggttgccaag cagtgcacag ataaacggat tagaaccaac   2160

ctcttacagg tatgtgagcg aatcccaacc ataagcaccc agctcaaaat cctgtccaca   2220

gtgaaggcca ccatgctggg ccggaccaac atcagtgatg aggagtctga gcaggccaca   2280

gagatgctgg ttcacaatgc ccagaacctc atgcagtctg tgaaggagac tgtgcgggaa   2340

gctgaagctg cttcaatcaa aattcgaaca gatgctggat ttacactgcg ctgggttaga   2400

aagactccct ggtaccagta g                                             2421
```

```
<210> SEQ ID NO 61
<211> LENGTH: 806
<212> TYPE: PRT
<213> ORGANISM: Homo sapiens

<400> SEQUENCE: 61

Gly Gln Met Thr Asp Gln Val Ala Asp Leu Arg Ala Arg Gly Gln Gly
1               5                   10                  15

Ser Ser Pro Val Ala Met Gln Lys Ala Gln Gln Val Ser Gln Gly Leu
            20                  25                  30

Asp Val Leu Thr Ala Lys Val Glu Asn Ala Ala Arg Lys Leu Glu Ala
        35                  40                  45

Met Thr Asn Ser Lys Gln Ser Ile Ala Lys Lys Ile Asp Ala Ala Gln
    50                  55                  60

Asn Trp Leu Ala Asp Pro Asn Gly Gly Pro Glu Gly Glu Glu Gln Ile
65                  70                  75                  80

Arg Gly Ala Leu Ala Glu Ala Arg Lys Ile Ala Glu Leu Cys Asp Asp
                85                  90                  95

Pro Lys Glu Arg Asp Asp Ile Leu Arg Ser Leu Gly Glu Ile Ser Ala
            100                 105                 110

Leu Thr Ser Lys Leu Ala Asp Leu Arg Arg Gln Gly Lys Gly Asp Ser
        115                 120                 125

Pro Glu Ala Arg Ala Leu Ala Lys Gln Val Ala Thr Ala Leu Gln Asn
    130                 135                 140

Leu Gln Thr Lys Thr Asn Arg Ala Val Ala Asn Ser Arg Pro Ala Lys
145                 150                 155                 160

Ala Ala Val His Leu Glu Gly Lys Ile Glu Gln Ala Gln Arg Trp Ile
                165                 170                 175

Asp Asn Pro Thr Val Asp Asp Arg Gly Val Gly Gln Ala Ala Ile Arg
            180                 185                 190

Gly Leu Val Ala Glu Gly His Arg Leu Ala Asn Val Met Met Gly Pro
        195                 200                 205

Tyr Arg Gln Asp Leu Leu Ala Lys Cys Asp Arg Val Asp Gln Leu Thr
    210                 215                 220

Ala Gln Leu Ala Asp Leu Ala Ala Arg Gly Glu Gly Glu Ser Pro Gln
225                 230                 235                 240
```

```
Ala Arg Ala Leu Ala Ser Gln Leu Gln Asp Ser Leu Lys Asp Leu Lys
                245                 250                 255

Ala Arg Met Gln Glu Ala Met Thr Gln Glu Val Ser Asp Val Phe Ser
            260                 265                 270

Asp Thr Thr Thr Pro Ile Lys Leu Leu Ala Val Ala Ala Thr Ala Pro
        275                 280                 285

Pro Asp Ala Pro Asn Arg Glu Glu Val Phe Asp Glu Arg Ala Ala Asn
    290                 295                 300

Phe Glu Asn His Ser Gly Lys Leu Gly Ala Thr Ala Glu Lys Ala Ala
305                 310                 315                 320

Ala Val Gly Thr Ala Asn Lys Ser Thr Val Glu Gly Ile Gln Ala Ser
                325                 330                 335

Val Lys Thr Ala Arg Glu Leu Thr Pro Gln Val Val Ser Ala Ala Arg
            340                 345                 350

Ile Leu Leu Arg Asn Pro Gly Asn Gln Ala Ala Tyr Glu His Phe Glu
        355                 360                 365

Thr Met Lys Asn Gln Trp Ile Asp Asn Val Glu Lys Met Thr Gly Leu
    370                 375                 380

Val Asp Glu Ala Ile Asp Thr Lys Ser Leu Leu Asp Ala Ser Glu Glu
385                 390                 395                 400

Ala Ile Lys Lys Asp Leu Asp Lys Cys Lys Val Ala Met Ala Asn Ile
                405                 410                 415

Gln Pro Gln Met Leu Val Ala Gly Ala Thr Ser Ile Ala Arg Arg Ala
            420                 425                 430

Asn Arg Ile Leu Leu Val Ala Lys Arg Glu Val Glu Asn Ser Glu Asp
        435                 440                 445

Pro Lys Phe Arg Glu Ala Val Lys Ala Ala Ser Asp Glu Leu Ser Lys
    450                 455                 460

Thr Ile Ser Pro Met Val Met Asp Ala Lys Ala Val Ala Gly Asn Ile
465                 470                 475                 480

Ser Asp Pro Gly Leu Gln Lys Ser Phe Leu Asp Ser Gly Tyr Arg Ile
                485                 490                 495

Leu Gly Ala Val Ala Lys Val Arg Glu Ala Phe Gln Pro Gln Glu Pro
            500                 505                 510

Asp Phe Pro Pro Pro Pro Pro Asp Leu Glu Gln Leu Arg Leu Thr Asp
        515                 520                 525

Glu Leu Ala Pro Pro Lys Pro Pro Leu Pro Glu Gly Glu Val Pro Pro
    530                 535                 540

Pro Arg Pro Pro Pro Pro Glu Glu Lys Asp Glu Glu Phe Pro Glu Gln
545                 550                 555                 560

Lys Ala Gly Glu Val Ile Asn Gln Pro Met Met Met Ala Ala Arg Gln
                565                 570                 575

Leu His Asp Glu Ala Arg Lys Trp Ser Ser Lys Pro Gly Ile Pro Ala
            580                 585                 590

Ala Glu Val Gly Ile Gly Val Val Ala Glu Ala Asp Ala Ala Asp Ala
        595                 600                 605

Ala Gly Phe Pro Val Pro Pro Asp Met Glu Asp Asp Tyr Glu Pro Glu
    610                 615                 620

Leu Leu Leu Met Pro Ser Asn Gln Pro Val Asn Gln Pro Ile Leu Ala
625                 630                 635                 640

Ala Ala Gln Ser Leu His Arg Glu Ala Thr Lys Trp Ser Ser Lys Gly
                645                 650                 655

Asn Asp Ile Ile Ala Ala Ala Lys Arg Met Ala Leu Leu Met Ala Glu
```

```
            660                 665                 670

Met Ser Arg Leu Val Arg Gly Gly Ser Gly Thr Lys Arg Ala Leu Ile
        675                 680                 685

Gln Cys Ala Lys Asp Ile Ala Lys Ala Ser Asp Glu Val Thr Arg Leu
    690                 695                 700

Ala Lys Glu Val Ala Lys Gln Cys Thr Asp Lys Arg Ile Arg Thr Asn
705                 710                 715                 720

Leu Leu Gln Val Cys Glu Arg Ile Pro Thr Ile Ser Thr Gln Leu Lys
                725                 730                 735

Ile Leu Ser Thr Val Lys Ala Thr Met Leu Gly Arg Thr Asn Ile Ser
            740                 745                 750

Asp Glu Glu Ser Glu Gln Ala Thr Glu Met Leu Val His Asn Ala Gln
        755                 760                 765

Asn Leu Met Gln Ser Val Lys Glu Thr Val Arg Glu Ala Glu Ala Ala
    770                 775                 780

Ser Ile Lys Ile Arg Thr Asp Ala Gly Phe Thr Leu Arg Trp Val Arg
785                 790                 795                 800

Lys Thr Pro Trp Tyr Gln
                805


<210> SEQ ID NO 62
<211> LENGTH: 279
<212> TYPE: DNA
<213> ORGANISM: Homo sapiens

<400> SEQUENCE: 62

atggacgagc ttctaagaga aagggacata ctaaataaga acatgcttaa ggcggtcaat      60

gcgacccaga agcagacaga cttggtaaag ctccatgaac aagccaagag gaacctggag     120

ggagaaatcc agaactacaa ggatgaggct cagaagcaga gaaagatcat ctttcatctg     180

gaaaaggagc gtgaccggta catcaaccaa gccagtgacc ttacgcaaaa ggctgactct     240

gtcaggatgc cctggcctct ggacaaaggg aaatggtga                            279


<210> SEQ ID NO 63
<211> LENGTH: 92
<212> TYPE: PRT
<213> ORGANISM: Homo sapiens

<400> SEQUENCE: 63

Met Asp Glu Leu Leu Arg Glu Arg Asp Ile Leu Asn Lys Asn Met Leu
1               5                   10                  15

Lys Ala Val Asn Ala Thr Gln Lys Gln Thr Asp Leu Val Lys Leu His
            20                  25                  30

Glu Gln Ala Lys Arg Asn Leu Glu Gly Glu Ile Gln Asn Tyr Lys Asp
        35                  40                  45

Glu Ala Gln Lys Gln Arg Lys Ile Ile Phe His Leu Glu Lys Glu Arg
    50                  55                  60

Asp Arg Tyr Ile Asn Gln Ala Ser Asp Leu Thr Gln Lys Ala Asp Ser
65                  70                  75                  80

Val Arg Met Pro Trp Pro Leu Asp Lys Gly Lys Trp
                85                  90


<210> SEQ ID NO 64
<211> LENGTH: 187
<212> TYPE: DNA
<213> ORGANISM: Homo sapiens
```

<400> SEQUENCE: 64

```
tctcactctc acaaccaatg aggaatactt ggacctcagc caacctctcg aacagtattc     60

acctagttac cctgacacaa gaagttcttg ttcttcagga gatgattctg tttttctcc    120

agaccccatg ccttacgaac catgccttcc tcagtatcca cacataaacg gcagtgttaa    180

aacatga                                                              187
```

<210> SEQ ID NO 65
<211> LENGTH: 139
<212> TYPE: DNA
<213> ORGANISM: Homo sapiens
<220> FEATURE:
<221> NAME/KEY: variation
<222> LOCATION: (112)..(112)
<223> OTHER INFORMATION: Y = C or T (dbSNP entry rs1047057)

<400> SEQUENCE: 65

```
gcagttggta gaagacttgg atcgaattct cactctcaca accaatgagg aggagaagaa     60

ggtttctgga gcagtggact gccacaagcc accatgtaac ccctctcacc tgccgtgcgt    120

aytggctgtg gaccagtag                                                 139
```

<210> SEQ ID NO 66
<211> LENGTH: 85
<212> TYPE: DNA
<213> ORGANISM: Homo sapiens

<400> SEQUENCE: 66

```
tctcactctc acaaccaatg aggaatactt ggacctcagt cagcctctcg aaccgtattc     60

accttgttat cctgacccaa gatga                                           85
```

<210> SEQ ID NO 67
<211> LENGTH: 55
<212> TYPE: DNA
<213> ORGANISM: Homo sapiens

<400> SEQUENCE: 67

```
gcagttggta gaagacttgg atcgaattct cactctcaca accaatgaga tctga          55
```

<210> SEQ ID NO 68
<211> LENGTH: 3304
<212> TYPE: DNA
<213> ORGANISM: Homo sapiens
<220> FEATURE:
<221> NAME/KEY: variation
<222> LOCATION: (2388)..(2388)
<223> OTHER INFORMATION: R = G or A (dbSNP entry rs767809)
<220> FEATURE:
<221> NAME/KEY: variation
<222> LOCATION: (2814)..(2814)
<223> OTHER INFORMATION: S = C or G (dbSNP entry rs2131956)

<400> SEQUENCE: 68

```
atgccagtgt ttcatacgcg cacgatcgag agcatcctgg agccggtggc acagcagatc     60

tcccacctgg tgataatgca cgaggagggc gaggtggacg gcaaagccat tcctgacctc    120

accgcgcccg tggccgccgt gcaggcggcc gtcagcaacc tcgtccgggt tggaaaagag    180

actgttcaaa ccactgagga tcagattttg aagagagata tgccaccagc atttattaag    240

gttgagaatg cttgcaccaa gcttgtccag gcagctcaga tgcttcagtc agacccttac    300

tcagtgcctg ctcgagatta tctaattgat gggtcaaggg gcatcctctc tggaacatca    360

gacctgctcc ttaccttcga tgaggctgag gtccgtaaaa ttattagagt ttgcaaagga    420
```

-continued

```
attttggaat atcttacagt ggcagaggtg gtggagacta tggaagattt ggtcacttac    480
acaaagaatc ttgggccagg aatgactaag atggccaaga tgattgacga gagacagcag    540
gagctcactc accaggagca ccgagtgatg ttggtgaact cgatgaacac cgtgaaagag    600
ttgctgccag ttctcatttc agctatgaag atttttgtaa caactaaaaa ctcaaaaaac    660
caaggcatag aggaagcttt aaaaaatcgc aattttactg tagaaaaaat gagtgctgaa    720
attaatgaga taattcgtgt gttacaactc acctcttggg atgaagatgc ctgggccagc    780
aaggacactg aagccatgaa gagagcattg gcctccatag actccaaact gaaccaggcc    840
aaaggttggc tccgtgaccc tagtgcctcc ccaggggatg ctggtgagca ggccatcaga    900
cagatcttag atgaagctgg aaaagttggt gaactctgtg caggcaaaga acgcagggag    960
attctgggaa cttgcaaaat gctagggcag atgactgatc aagtggctga cctccgtgcc   1020
agaggacaag gatcctcacc ggtggccatg cagaaagctc agcaggtatc tcagggtctg   1080
gatgtgctca cagcaaaagt ggaaaatgca gctcgcaagc tggaagccat gaccaactca   1140
aagcagagca ttgcaaagaa gatcgatgct gctcagaact ggcttgcaga tccaaatggt   1200
ggaccggaag gagaagagca gattcgaggt gctttggctg aagctcggaa aatagcagaa   1260
ttatgtgatg atcctaaaga aagagatgac attctacgtt cccttgggga aatatctgct   1320
ctgacttcta aattagcaga tctacgaaga caggggaaag gagattctcc agaggctcga   1380
gccttggcca aacaggtggc cacggccctg cagaacctgc agaccaaaac caaccgggct   1440
gtggccaaca gcagaccggc caaagcagct gtacaccttg agggcaagat tgagcaagca   1500
cagcggtgga ttgataatcc cacagtggat gaccgtggag tcggtcaggc tgccatccgg   1560
gggcttgtgg ccgaagggca tcgtctggct aatgttatga tggggcctta tcggcaagat   1620
cttctcgcca agtgtgaccg agtggaccag ctgacagccc agctggctga cctggctgcc   1680
agaggggaag gggagagtcc tcaggcacga gcacttgcat ctcagctcca agactcctta   1740
aaggatctaa aagctcggat gcaggaggcc atgactcagg aagtgtcaga tgttttcagc   1800
gataccacaa ctcccatcaa gctgttggca gtggcagcca cggcgcctcc tgatgcgcct   1860
aacagggaag aggtatttga tgagagggca gctaactttg aaaaccattc aggaaagctt   1920
ggtgctacgg ccgagaaggc ggctgcggtt ggtactgcta ataaatcaac agtggaaggc   1980
attcaggcct cagtgaagac ggcccgagaa ctcacacccc aggtggtctc ggctgctcgt   2040
atcttactta ggaaccctgg aaatcaagct gcttatgaac attttgagac catgaagaac   2100
cagtggatcg ataatgttga aaaaatgaca gggctggtgg acgaagccat tgataccaaa   2160
tctctgttgg atgcttcaga agaagcaatt aaaaaagacc tggacaagtg caaggtagct   2220
atggccaaca ttcagcctca gatgctggtt gctggggcaa ccagtattgc tcgtcgggcc   2280
aaccggatcc tgctggtggc taagagggag gtggagaatt ccgaggatcc caagttccgt   2340
gaggctgtga aagctgcctc tgatgaattg agcaaaacca tctccccrat ggtgatggat   2400
gcaaaagctg tggctggaaa catttccgac cctggactgc aaaagagctt cctggactca   2460
ggatatcgga tcctgggagc tgtggccaag gtcagagaag ccttccaacc tcaggagcct   2520
gacttcccgc cgcctccacc agaccttgaa caactccgac taacagatga gcttgctcct   2580
cccaaaccac ctctgcctga aggtgaggtc cctccaccta ggcctccacc accagaggaa   2640
aaggatgaag agttccctga gcagaaggcc ggggaggtga ttaaccagcc aatgatgatg   2700
gctgccagac agctccatga tgaagctcgc aaatggtcca gcaagccggg catcccagcc   2760
```

```
gctgaggtgg gtataggtgt tgtagctgag gcagatgcgg ccgatgctgc tggsttccct   2820

gtccccccctg acatggaaga cgattacgaa cctgagctgc tgttaatgcc atccaatcag   2880

ccggtcaacc agcccattct ggccgcggct cagtccttgc atcgggaagc taccaagtgg   2940

tctagtaagg gcaatgacat cattgcagca gccaagcgca tggctctgct gatggctgag   3000

atgtctcggc tggtaagagg gggcagtggt accaagcggg cactcattca gtgtgccaag   3060

gacatcgcca aggcctcaga tgaggtgact cggttggcca aggaggttgc caagcagtgc   3120

acagataaac ggattagaac caacctctta caggtatgtg agcgaatccc aaccataagc   3180

acccagctca aaatcctgtc cacagtgaag gccaccatgc tgggccggac caacatcagt   3240

gatgaggagt ctgagcaggc cacagagatg ctggttcaca atgcccagaa cctcatgcag   3300

tctg                                                                3304
```

```
<210> SEQ ID NO 69
<211> LENGTH: 3100
<212> TYPE: DNA
<213> ORGANISM: Homo sapiens
<220> FEATURE:
<221> NAME/KEY: variation
<222> LOCATION: (2388)..(2388)
<223> OTHER INFORMATION: R = A or G (dbSNP entry rs767809)

<400> SEQUENCE: 69

atgccagtgt ttcatacgcg cacgatcgag agcatcctgg agccggtggc acagcagatc     60

tcccacctgg tgataatgca cgaggagggc gaggtggacg gcaaagccat tcctgacctc    120

accgcgcccg tggccgccgt gcaggcggcc gtcagcaacc tcgtccgggt tggaaaagag    180

actgttcaaa ccactgagga tcagattttg aagagagata tgccaccagc atttattaag    240

gttgagaatg cttgcaccaa gcttgtccag gcagctcaga tgcttcagtc agacccttac    300

tcagtgcctg ctcgagatta tctaattgat gggtcaaggg gcatcctctc tggaacatca    360

gacctgctcc ttaccttcga tgaggctgag gtccgtaaaa ttattagagt ttgcaaagga    420

attttggaat atcttacagt ggcagaggtg gtggagacta tggaagattt ggtcacttac    480

acaaagaatc ttgggccagg aatgactaag atggccaaga tgattgacga gagacagcag    540

gagctcactc accaggagca ccgagtgatg ttggtgaact cgatgaacac cgtgaaagag    600

ttgctgccag ttctcatttc agctatgaag atttttgtaa caactaaaaa ctcaaaaaac    660

caaggcatag aggaagcttt aaaaaatcgc aattttactg tagaaaaaat gagtgctgaa    720

attaatgaga taattcgtgt gttacaactc acctcttggg atgaagatgc ctgggccagc    780

aaggacactg aagccatgaa gagagcattg gcctccatag actccaaact gaaccaggcc    840

aaaggttggc tccgtgaccc tagtgcctcc ccaggggatg ctggtgagca ggccatcaga    900

cagatcttag atgaagctgg aaaagttggt gaactctgtg caggcaaaga acgcagggag    960

attctgggaa cttgcaaaat gctagggcag atgactgatc aagtggctga cctccgtgcc   1020

agaggacaag gatcctcacc ggtggccatg cagaaagctc agcaggtatc tcagggtctg   1080

gatgtgctca cagcaaaagt ggaaaatgca gctcgcaagc tggaagccat gaccaactca   1140

aagcagagca ttgcaaagaa gatcgatgct gctcagaact ggcttgcaga tccaaatggt   1200

ggaccggaag gagaagagca gattcgaggt gctttggctg aagctcggaa aatagcagaa   1260

ttatgtgatg atcctaaaga aagagatgac attctacgtt cccttgggga aatatctgct   1320

ctgacttcta aattagcaga tctacgaaga caggggaaag gagattctcc agaggctcga   1380

gccttggcca aacaggtggc cacggccctg cagaacctgc agaccaaaac caaccgggct   1440
```

```
gtggccaaca gcagaccggc caaagcagct gtacaccttg agggcaagat tgagcaagca   1500
cagcggtgga ttgataatcc cacagtggat gaccgtggag tcggtcaggc tgccatccgg   1560
gggcttgtgg ccgaagggca tcgtctggct aatgttatga tggggcctta tcggcaagat   1620
cttctcgcca agtgtgaccg agtggaccag ctgacagccc agctggctga cctggctgcc   1680
agaggggaag gggagagtcc tcaggcacga gcacttgcat ctcagctcca agactcctta   1740
aaggatctaa aagctcggat gcaggaggcc atgactcagg aagtgtcaga tgtttttcagc  1800
gataccacaa ctcccatcaa gctgttggca gtggcagcca cggcgcctcc tgatgcgcct   1860
aacagggaag aggtatttga tgagagggca gctaactttg aaaaccattc aggaaagctt   1920
ggtgctacgg ccgagaaggc ggctgcggtt ggtactgcta ataaatcaac agtggaaggc   1980
attcaggcct cagtgaagac ggcccgagaa ctcacacccc aggtggtctc ggctgctcgt   2040
atcttactta ggaaccctgg aaatcaagct gcttatgaac attttgagac catgaagaac   2100
cagtggatcg ataatgttga aaaaatgaca gggctggtgg acgaagccat tgataccaaa   2160
tctctgttgg atgcttcaga agaagcaatt aaaaaagacc tggacaagtg caaggtagct   2220
atggccaaca ttcagcctca gatgctggtt gctggggcaa ccagtattgc tcgtcgggcc   2280
aaccggatcc tgctggtggc taagagggag gtggagaatt ccgaggatcc caagttccgt   2340
gaggctgtga aagctgcctc tgatgaattg agcaaaacca tctccccrat ggtgatggat   2400
gcaaaagctg tggctggaaa catttccgac cctggactgc aaaagagctt cctggactca   2460
ggatatcgga tcctgggagc tgtggccaag gtcagagaag ccttccaacc tcaggagcct   2520
gacttcccgc cgcctccacc agaccttgaa caactccgac taacagatga gcttgctcct   2580
cccaaaccac ctctgcctga aggtgaggtc cctccaccta ggcctccacc accagaggaa   2640
aaggatgaag agttccctga gcagaaggcc ggggaggtga ttaaccagcc aatgatgatg   2700
gctgccagac agctccatga tgaagctcgc aaatggtcca gcaagggcaa tgacatcatt   2760
gcagcagcca agcgcatggc tctgctgatg gctgagatgt ctcggctggt aagagggggc   2820
agtggtacca agcgggcact cattcagtgt gccaaggaca tcgccaaggc ctcagatgag   2880
gtgactcggt tggccaagga ggttgccaag cagtgcacag ataaacggat tagaaccaac   2940
ctcttacagg tatgtgagcg aatcccaacc ataagcaccc agctcaaaat cctgtccaca   3000
gtgaaggcca ccatgctggg ccggaccaac atcagtgatg aggagtctga gcaggccaca   3060
gagatgctgg ttcacaatgc ccagaacctc atgcagtctg                         3100
```

<210> SEQ ID NO 70
<211> LENGTH: 883
<212> TYPE: DNA
<213> ORGANISM: Homo sapiens

<400> SEQUENCE: 70

```
atgccagtgt ttcatacgcg cacgatcgag agcatcctgg agccggtggc acagcagatc     60
tcccacctgg tgataatgca cgaggagggc gaggtggacg gcaaagccat tcctgacctc    120
accgcgcccg tggccgccgt gcaggcggcc gtcagcaacc tcgtccgggt tggaaaagag    180
actgttcaaa ccactgagga tcagattttg aagagagata tgccaccagc atttattaag    240
gttgagaatg cttgcaccaa gcttgtccag gcagctcaga tgcttcagtc agacccttac    300
tcagtgcctg ctcgagatta tctaattgat gggtcaaggg gcatcctctc tggaacatca    360
gacctgctcc ttaccttcga tgaggctgag gtccctccac ctaggcctcc accaccagag    420
```

```
gaaaaggatg aagagttccc tgagcagaag gccggggagg tgattaacca gccaatgatg    480

atggctgcca gacagctcca tgatgaagct cgcaaatggt ccagcaaggg caatgacatc    540

attgcagcag ccaagcgcat ggctctgctg atggctgaga tgtctcggct ggtaagaggg    600

ggcagtggta ccaagcgggc actcattcag tgtgccaagg acatcgccaa ggcctcagat    660

gaggtgactc ggttggccaa ggaggttgcc aagcagtgca cagataaacg gattagaacc    720

aacctcttac aggtatgtga gcgaatccca accataagca cccagctcaa aatcctgtcc    780

acagtgaagg ccaccatgct gggccggacc aacatcagtg atgaggagtc tgagcaggcc    840

acagagatgc tggttcacaa tgcccagaac ctcatgcagt ctg                     883
```

<210> SEQ ID NO 71
<211> LENGTH: 2359
<212> TYPE: DNA
<213> ORGANISM: Homo sapiens

<400> SEQUENCE: 71

```
atggctgagg aaaagggtgg aaagcaagtc ctggaagaat ctgcatttga agaaatggaa     60

agagattttc agggagttct ccatgaactt tctggagaca aaagtttgga aaaatttcgg    120

attgaatatg agaggcttca tgctgtcatg aaaaagtctt atgacaatga aaagcgtctg    180

atggccaaat gcagagagct aaatgcagag attgtagtga attctgcgaa ggtcgccact    240

gcccttaagc tctctcagga tgatcagacc accattgcat ccctaaagaa ggaaattgaa    300

aaggcctgga agatggtgga ctcagcctat gacaaagagc agaaggccaa ggagacgatt    360

cttgctctga aagaggaaat agtgaacctg accaaactag tggagcaggg gtctggactg    420

tcaatggacc agcatagcaa catccgagat ttactgaggt tcaaagaaga agtgacaaag    480

gagagagacc agctcttatc agaagtggta aaattacgag aatccctagc tcagaccact    540

gaacagcagc aggaaacaga gcgatcaaaa gaggaggctg aacatgccat cagtcagttc    600

caacaagaaa tccagcaacg tcagaacgaa gcttcccggg agttccggaa gaaggaaaaa    660

ctagagaaag agctcaagca gattcaggca gacatggaca gcaggcagac agaaataaaa    720

gccctgcagc agtatgtgca gaagagcaag gaggagcttc agaagctgga gcagcagctg    780

aaggagcaga agatattgaa tgagagagct gcaaaggaac tcgagcaatt tcagatgaga    840

aatgctaaac ttcagcaaga gaatgaacag cacagtttgg tctgtgagca gctatcccag    900

gaaaaccaac agaaggcgtt ggagctcaaa gccaaagagg aagaagtcca tcaaatgcgc    960

cttgacatcg ggaagctcaa caaaatcaga gaacaaattc ataagaaatt gcaccacacc   1020

gaagatcaaa aggcagaagt cgaacagcac aaagaaaccc taaaaaatca gattgtggga   1080

ttagagagag aggtagaggc ttcaaagaaa caagcagaac ttgacagaaa ggcaatggac   1140

gagcttctaa gagaaaggga catactaaat aagaacatgc ttaaggcggt caatgcgacc   1200

cagaagcaga cagacttggt aaagctccat gaacaagcca agaggaacct ggagggagaa   1260

atccagaact acaaggatga ggctcagaag cagagaaaga tcatctttca tctggaaaag   1320

gagcgtgacc ggtacatcaa ccaagccagt gaccttacgc aaaaggtcct tatgaacatg   1380

gaagacataa aagttcgtga aacacagatt tttgactaca ggaaaaaaat agctgaatca   1440

gagattaaat taaaacagca acagaaccta tatgaagctg tgagatcaga cagaaatctg   1500

tatagcaaaa atctggttga ggctcaggat gaaataacag atatgaagag aaagttaaag   1560

attatgatcc atcaggtaga tgagctgaaa gaagacatct ctgccaaaga gtccgcactt   1620

gtgaagctgc acctggaaca gcagcgaata gaaaaggaaa aggaaacatt gaaggctgag   1680
```

```
ctgcagaagc tgagacaaca agccctggag acaaaacact ttattgaaaa gcaagaagct   1740

gaagagagaa aactcctgcg aataattgct gaggctgacg gggagaggtt gagacagaag   1800

aaggaattag accaggtcat cagtgagaga gatatcctgg ggtctcagct tgttcggcgc   1860

aatgatgagt tagctttgct ctatgagaag atcaagatcc aacagtctgt gctgaataaa   1920

ggggagagcc agtacaacca gaggttggag gacatgagaa tcctcagact tgagatcaag   1980

aagcttcgcc gggaaaaggg gattcttgcc aggagtatgg ctaatgttga agaactcaga   2040

caggagtttt ttcacatgca aagagaattg ttgaaggaga ggacacgctg ccgagccctg   2100

gaggaggagc tggagaatcc cctgaatgtg cacagatgga ggaagctcga ggccagcgac   2160

cccaatgcat atgagctgat acagaaaatt cacaccctgc agaagcgtct catcagcaag   2220

actgaagagg tggttgaaaa agagctgctc ctccaggaaa aggagaaact ctacatggaa   2280

ctaaagcacg tcttggcccg ccagcctgga cctgaggctg cggaacagct gaagctgtac   2340

cgacgcacgc tgcatgaca                                                2359
```

```
<210> SEQ ID NO 72
<211> LENGTH: 32
<212> TYPE: DNA
<213> ORGANISM: Homo sapiens

<400> SEQUENCE: 72

caagcagttg gtagaagact tggatcgaat tc                                   32
```

```
<210> SEQ ID NO 73
<211> LENGTH: 61
<212> TYPE: DNA
<213> ORGANISM: Homo sapiens

<400> SEQUENCE: 73

caaccaatga ggtggtctcg gctgctcgta tcttacttag gaaccctgga aatcaagctg     60

a                                                                     61
```

```
<210> SEQ ID NO 74
<211> LENGTH: 67
<212> TYPE: DNA
<213> ORGANISM: Homo sapiens
<220> FEATURE:
<221> NAME/KEY: Unsure
<222> LOCATION: (66)..(66)
<223> OTHER INFORMATION: n is a, t, c, or g

<400> SEQUENCE: 74

ttggttgtga gagtgagaat tcgatccaag tcttctacca actgcttgaa cgttggtctc     60

tgaagnc                                                               67
```

```
<210> SEQ ID NO 75
<211> LENGTH: 78
<212> TYPE: DNA
<213> ORGANISM: Homo sapiens

<400> SEQUENCE: 75

ccaatgagga aaagggtgga aagcaagtcc tggaagaatc tgcatttgaa gaaatggaaa     60

gagattttca gggaaact                                                   78
```

```
<210> SEQ ID NO 76
<211> LENGTH: 60
<212> TYPE: DNA
```

-continued

```
<213> ORGANISM: Homo sapiens
<220> FEATURE:
<221> NAME/KEY: Unsure
<222> LOCATION: (13)..(13)
<223> OTHER INFORMATION: n is a, t, c, or g

<400> SEQUENCE: 76

gtgagagtga ganttcgatc caagtcttct accaactgct tgaacgttgg tctctgaagt     60


<210> SEQ ID NO 77
<211> LENGTH: 71
<212> TYPE: DNA
<213> ORGANISM: Homo sapiens
<220> FEATURE:
<221> NAME/KEY: Unsure
<222> LOCATION: (71)..(71)
<223> OTHER INFORMATION: n is a, t, c, or g

<400> SEQUENCE: 77

aatgaggaat acttggacct cagccaacct ctcgaacagt attcacctag ttaccctgac     60

acaagaagaa n                                                          71


<210> SEQ ID NO 78
<211> LENGTH: 73
<212> TYPE: DNA
<213> ORGANISM: Homo sapiens

<400> SEQUENCE: 78

ttcctcattg gttgtgagag tgagaattcg atccaagtct tctaccaact gcttgaacgt     60

tggtctctga aca                                                        73


<210> SEQ ID NO 79
<211> LENGTH: 100
<212> TYPE: DNA
<213> ORGANISM: Homo sapiens

<400> SEQUENCE: 79

agcagttggt agaagacttg gatcgaattc tcactctcac aaccaatgag gtggtctcgg     60

ctgctcgtat cttacttagg aaccctggaa atcaagctgc                          100


<210> SEQ ID NO 80
<211> LENGTH: 100
<212> TYPE: DNA
<213> ORGANISM: Homo sapiens

<400> SEQUENCE: 80

agcagttggt agaagacttg gatcgaattc tcactctcac aaccaatgag gaaaagggtg     60

gaaagcaagt cctggaagaa tctgcatttg aagaaatgga                          100
```